US010194905B2

(12) United States Patent
Bolduc et al.

(10) Patent No.: US 10,194,905 B2
(45) Date of Patent: Feb. 5, 2019

(54) DEVICES, SYSTEMS, AND METHODS FOR ENDOVASCULAR STAPLE AND/OR PROSTHESIS DELIVERY AND IMPLANTATION

(71) Applicant: Medtronic Vascular, Inc., Minneapolis, MN (US)

(72) Inventors: Lee Bolduc, Redwood City, CA (US); Jimmy Jen, Saratoga, CA (US)

(73) Assignee: MEDTRONIC VASCULAR, INC., Minneapolis, MN (US)

( * ) Notice: Subject to any disclaimer, the term of this patent is extended or adjusted under 35 U.S.C. 154(b) by 132 days.

(21) Appl. No.: 15/246,271

(22) Filed: Aug. 24, 2016

(65) Prior Publication Data

US 2016/0361058 A1   Dec. 15, 2016

Related U.S. Application Data

(60) Division of application No. 12/288,031, filed on Oct. 16, 2008, now abandoned, which is a
(Continued)

(51) Int. Cl.
*A61B 17/068* (2006.01)
*A61B 17/064* (2006.01)
(Continued)

(52) U.S. Cl.
CPC .......... *A61B 17/068* (2013.01); *A61B 6/481* (2013.01); *A61B 17/064* (2013.01); *A61B 50/30* (2016.02);
(Continued)

(58) Field of Classification Search
CPC ....... A61B 17/068; A61B 6/481; A61B 50/30; A61B 50/3001; A61B 17/064;
(Continued)

(56) References Cited

U.S. PATENT DOCUMENTS 2,033,039 A   3/1936   Limpert
3,499,222 A   3/1970   Linkow et al.
(Continued)

FOREIGN PATENT DOCUMENTS

AU   2002353807 B2   6/2003
AU   2004277897 B2   4/2005
(Continued)

OTHER PUBLICATIONS

"U.S. Appl. No. 10/307,226, 312 Amendment filed Oct. 24, 2011", 3 pgs.
(Continued)

*Primary Examiner* — Richard G Louis

(57) ABSTRACT

Devices, systems, and methods for implanting expandable prostheses in the body lumens rely on stapling or anchoring the prostheses with separately introduced fasteners. The prostheses may be self-expanding or balloon expandable, and may include a single lumen or more than one lumen. After initial placement, a stapling system is introduced within the expanded prosthesis to deploy a plurality of fasteners to at least one prosthesis end. The stapling system may apply a force to the prosthesis to modify the shape of the prosthesis to conform to the shape of the vessel wall. The stapling system can be deflected in one or more distinct steerable segments. A lumen extension or lumens may be coupled to the prosthesis to extend the reach of the prosthesis within the implantation site. Fasteners may also be applied to the lumen extensions.

7 Claims, 37 Drawing Sheets

Related U.S. Application Data continuation-in-part of application No. 11/488,305, filed on Jul. 18, 2006, now abandoned, and a continuation-in-part of application No. 11/255,116, filed on Oct. 20, 2005, now Pat. No. 7,637,932, and a continuation-in-part of application No. 11/254,619, filed on Oct. 20, 2005, now Pat. No. 9,320,503, and a continuation-in-part of application No. 11/633,724, filed on Dec. 5, 2006, now Pat. No. 8,080,050, which is a division of application No. 10/692,283, filed on Oct. 23, 2003, now Pat. No. 7,147,657, and a continuation-in-part of application No. 10/786,465, filed on Feb. 25, 2004, now Pat. No. 8,231,639, and a continuation-in-part of application No. 11/166,428, filed on Jun. 24, 2005, now abandoned, which is a division of application No. 10/693,255, filed on Oct. 24, 2003, now Pat. No. 8,929,661, and a continuation-in-part of application No. 10/307,226, filed on Nov. 29, 2002, now Pat. No. 8,075,570, and a continuation-in-part of application No. 10/669,881, filed on Sep. 24, 2003, now Pat. No. 7,491,232, and a continuation-in-part of application No. 11/166,411, filed on Jun. 24, 2005, now Pat. No. 8,092,519, which is a division of application No. 10/271,334, filed on Oct. 15, 2002, now Pat. No. 6,960,217.

(60) Provisional application No. 60/488,753, filed on Jul. 21, 2003, provisional application No. 60/489,011, filed on Jul. 21, 2003, provisional application No. 60/333,937, filed on Nov. 28, 2001.

(51) Int. Cl.

| *A61F 2/00* | (2006.01) |
|---|---|
| *A61F 2/07* | (2013.01) |
| *A61F 2/954* | (2013.01) |
| *A61F 2/966* | (2013.01) |
| *A61F 2/89* | (2013.01) |
| *A61B 50/30* | (2016.01) |
| *A61B 6/00* | (2006.01) |
| *A61M 25/01* | (2006.01) |
| *A61M 25/09* | (2006.01) |
| *A61B 17/00* | (2006.01) |
| *A61F 2/06* | (2013.01) |
| *A61F 2/852* | (2013.01) |
| *A61F 2/30* | (2006.01) |
| *A61F 2/848* | (2013.01) |
| *A61F 2/95* | (2013.01) |

(52) U.S. Cl.
CPC ........ *A61B 50/3001* (2016.02); *A61F 2/0095* (2013.01); *A61F 2/07* (2013.01); *A61F 2/89* (2013.01); *A61F 2/954* (2013.01); *A61F 2/966* (2013.01); *A61M 25/0108* (2013.01); *A61M 25/0147* (2013.01); *A61M 25/09* (2013.01); *A61B 2017/00296* (2013.01); *A61B 2017/00336* (2013.01); *A61B 2017/00398* (2013.01); *A61B 2017/00734* (2013.01); *A61B 2017/0649* (2013.01); *A61B 2017/0688* (2013.01); *A61F 2/064* (2013.01); *A61F 2/852* (2013.01); *A61F 2002/061* (2013.01); *A61F 2002/067* (2013.01); *A61F 2002/075* (2013.01); *A61F 2002/30617* (2013.01); *A61F 2002/8486* (2013.01); *A61F 2002/9511* (2013.01); *A61F 2002/9517* (2013.01); *A61F 2220/0066* (2013.01); *A61F 2220/0075* (2013.01); *A61F 2250/0063* (2013.01); *A61F 2250/0097* (2013.01)

(58) Field of Classification Search
CPC ..... A61M 25/09; A61M 25/0147; A61F 2/89; A61F 2/966; A61F 2/07; A61F 2/0095
See application file for complete search history.

(56) References Cited

U.S. PATENT DOCUMENTS

| 3,686,740 A | 8/1972 | Shiley |
|---|---|---|
| 3,799,172 A | 3/1974 | Szpur |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,694,827 A | 9/1987 | Weiner et al. |
| 4,781,682 A | 11/1988 | Patel |
| 4,822,345 A | 4/1989 | Danforth |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski |
| 5,192,314 A | 3/1993 | Daskalakis |
| 5,195,968 A | 3/1993 | Lundquist et al. |
| 5,199,950 A | 4/1993 | Schmitt et al. |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,352,197 A | 10/1994 | Hammersmark et al. |
| 5,364,351 A | 11/1994 | Heinzelman et al. |
| 5,383,880 A | 1/1995 | Hooven |
| 5,387,235 A | 2/1995 | Chuter |
| 5,409,498 A | 4/1995 | Braddock et al. |
| 5,456,713 A | 10/1995 | Chutter |
| 5,456,714 A | 10/1995 | Owen |
| 5,470,337 A | 11/1995 | Moss |
| 5,474,568 A | 12/1995 | Scott |
| 5,480,382 A | 1/1996 | Hammerslag et al. |
| 5,480,423 A | 1/1996 | Ravenscroft et al. |
| 5,489,295 A | 2/1996 | Piolani et al. |
| 5,522,881 A | 6/1996 | Lentz |
| 5,531,686 A | 7/1996 | Lundquist et al. |
| 5,534,007 A | 7/1996 | St Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,591,195 A | 1/1997 | Taheri et al. |
| 5,609,627 A | 3/1997 | Goicechea et al. |
| 5,626,613 A | 5/1997 | Schmieding |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dercume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicechea et al. |
| 5,693,084 A | 12/1997 | Chuter |
| 5,693,086 A | 12/1997 | Goicechea et al. |
| 5,700,269 A | 12/1997 | Pinchuk et al. |
| 5,702,343 A | 12/1997 | Alferness |

(56) References Cited

U.S. PATENT DOCUMENTS

| | | |
|---|---|---|
| 5,702,365 A | 12/1997 | King |
| 5,702,408 A | 12/1997 | Wales et al. |
| 5,707,376 A | 1/1998 | Kavteledze et al. |
| 5,713,907 A | 2/1998 | Bogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,779,731 A | 7/1998 | Leavitt |
| 5,782,844 A | 7/1998 | Yoon et al. |
| 5,797,933 A | 8/1998 | Snow et al. |
| 5,800,528 A | 9/1998 | Lederman et al. |
| 5,810,882 A | 9/1998 | Bolduc et al. |
| 5,814,016 A | 9/1998 | Valley et al. |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A | 11/1998 | Stein et al. |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A | 2/1999 | Whayne |
| 5,873,906 A | 2/1999 | Lau et al. |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thomson et al. |
| 5,916,263 A | 6/1999 | Goicechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,129,685 A | 10/2000 | Howard, III |
| 6,145,509 A | 11/2000 | Tanner |
| 6,146,339 A | 11/2000 | Biagtan et al. |
| 6,152,144 A | 11/2000 | Lesh et al. |
| 6,162,168 A | 12/2000 | Schweich, Jr. et al. |
| 6,168,610 B1 | 1/2001 | Marin et al. |
| 6,174,323 B1 | 1/2001 | Biggs et al. |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 | 3/2001 | Chin et al. |
| 6,217,597 B1 | 4/2001 | Tanner |
| 6,224,540 B1 | 5/2001 | Lederman et al. |
| 6,231,561 B1 | 5/2001 | Frazier et al. |
| 6,248,118 B1 | 6/2001 | Tanner et al. |
| 6,250,974 B1 | 6/2001 | Kerek |
| 6,251,132 B1 | 6/2001 | Ravenscroft et al. |
| 6,258,021 B1 | 7/2001 | Wilk |
| 6,258,119 B1 | 7/2001 | Hussein et al. |
| 6,270,516 B1 | 8/2001 | Tanner et al. |
| 6,273,858 B1 | 8/2001 | Fox et al. |
| 6,286,514 B1 | 9/2001 | Lemelson |
| 6,287,315 B1 | 9/2001 | Wijeratne et al. |
| 6,287,335 B1 | 9/2001 | Drasler et al. |
| 6,293,906 B1 | 9/2001 | Vanden Hoek et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,343,605 B1 | 2/2002 | Lafontaine |
| 6,346,118 B1 | 2/2002 | Baker et al. |
| 6,352,561 B1 | 3/2002 | Leopold et al. |
| 6,361,556 B1 | 3/2002 | Chuter |
| 6,368,345 B1 | 4/2002 | Dehdashtian et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson, IV et al. |
| 6,406,420 B1 | 6/2002 | McCarthy et al. |
| 6,409,757 B1 | 6/2002 | Trout, III et al. |
| 6,416,365 B1 | 7/2002 | Iwahori |
| 6,416,522 B1 | 7/2002 | Strecker |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,461,365 B2 | 10/2002 | Bolduc et al. |
| 6,468,260 B1 | 10/2002 | Bumbalough et al. |
| 6,482,224 B1 | 11/2002 | Michler et al. |
| 6,520,974 B2 | 2/2003 | Tanner et al. |
| 6,544,253 B1 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenberg et al. |
| 6,592,593 B1 | 7/2003 | Parodi et al. |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,639,278 B2 | 10/2003 | Sumida et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B1 | 3/2004 | Lazarus |
| 6,709,442 B2 | 3/2004 | Miller et al. |
| 6,719,174 B1 | 4/2004 | Swift |
| 6,730,119 B1 | 5/2004 | Smalling |
| 6,746,460 B2 | 6/2004 | Gannoe et al. |
| 6,800,081 B2 | 10/2004 | Parodi |
| 6,929,661 B2 | 8/2005 | Bolduc et al. |
| 6,960,217 B2 | 11/2005 | Bolduc |
| 6,878,164 B2 | 12/2005 | Kujawski et al. |
| 6,984,241 B2 | 1/2006 | Lubbers et al. |
| 6,986,775 B2 | 1/2006 | Morales et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,021 B1 | 6/2006 | Wilk |
| 7,060,023 B2 | 6/2006 | French et al. |
| 7,081,086 B2 | 7/2006 | Lau et al. |
| 7,081,129 B2 | 7/2006 | Chobotov |
| 7,128,754 B2 | 10/2006 | Bolduc |
| 7,147,657 B2 | 12/2006 | Chiang et al. |
| 7,155,295 B2 | 12/2006 | Lau et al. |
| 7,179,225 B2 | 2/2007 | Shluzas et al. |
| 7,306,623 B2 | 12/2007 | Watson |
| 7,335,213 B1 | 2/2008 | Hyde et al. |
| 7,361,137 B2 | 4/2008 | Taylor et al. |
| 7,404,824 B1 | 7/2008 | Webler et al. |
| 7,422,558 B2 | 9/2008 | Lau et al. |
| 7,491,232 B2 | 2/2009 | Bolduc et al. |
| 7,544,198 B2 | 6/2009 | Parodi |

(56) References Cited

U.S. PATENT DOCUMENTS

| | | |
|---|---|---|
| 7,563,267 B2 | 7/2009 | Goldfarb et al. |
| 7,591,842 B2 | 9/2009 | Parodi |
| 7,637,932 B2 | 12/2009 | Bolduc et al. |
| 7,704,269 B2 | 4/2010 | St. Goar et al. |
| 7,727,189 B2 | 6/2010 | Vantassel et al. |
| 7,753,922 B2 | 7/2010 | Starksen |
| 7,811,295 B2 | 10/2010 | Kortenbach |
| 7,823,267 B2 | 11/2010 | Bolduc |
| 7,828,267 B2 | 11/2010 | Iwabuchi et al. |
| 7,828,838 B2 | 11/2010 | Bolduc et al. |
| 7,959,663 B2 | 6/2011 | Bolduc |
| 7,959,670 B2 | 6/2011 | Bolduc |
| 8,075,570 B2 | 12/2011 | Bolduc et al. |
| 8,080,050 B2 | 12/2011 | Chiang et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,685,044 B2 | 4/2014 | Bolduc et al. |
| 8,690,897 B2 | 4/2014 | Bolduc |
| 9,023,065 B2 | 5/2015 | Bolduc et al. |
| 2001/0041821 A1 | 11/2001 | Wilk |
| 2001/0047199 A1 | 11/2001 | Wijay |
| 2002/0026144 A1 | 2/2002 | Patterson |
| 2002/0029077 A1 | 3/2002 | Leopold et al. |
| 2002/0058855 A1 | 5/2002 | Schweich, Jr. et al. |
| 2002/0065485 A1 | 5/2002 | DuBois et al. |
| 2002/0087169 A1 | 7/2002 | Brock et al. |
| 2002/0099432 A1 | 7/2002 | Yee |
| 2002/0133054 A1 | 9/2002 | Murphy et al. |
| 2002/0156365 A1 | 10/2002 | Tsekos |
| 2002/0156521 A1 | 10/2002 | Ryan et al. |
| 2002/0183827 A1 | 12/2002 | Derus et al. |
| 2003/0004560 A1 | 1/2003 | Chobotov et al. |
| 2003/0018358 A1 | 1/2003 | Saadat |
| 2003/0060674 A1 | 3/2003 | Gifford, III et al. |
| 2003/0078465 A1 | 4/2003 | Pai et al. |
| 2003/0100943 A1 | 5/2003 | Bolduc |
| 2003/0105384 A1 | 6/2003 | Sharkey et al. |
| 2003/0105519 A1 | 6/2003 | Fasol et al. |
| 2003/0130731 A1 | 7/2003 | Vidlund et al. |
| 2003/0149463 A1 | 8/2003 | Solymar et al. |
| 2003/0158570 A1 | 8/2003 | Ferrazzi |
| 2003/0163085 A1 | 8/2003 | Tanner et al. |
| 2003/0204249 A1 | 10/2003 | Letort |
| 2003/0233140 A1 | 12/2003 | Hartley et al. |
| 2004/0002731 A1 | 1/2004 | Aganon et al. |
| 2004/0039405 A1 | 2/2004 | Petrovic et al. |
| 2004/0044364 A1 | 3/2004 | Devries et al. |
| 2004/0049207 A1* | 3/2004 | Goldfarb ............ A61M 25/0136 606/139 |
| 2004/0054352 A1 | 3/2004 | Adams et al. |
| 2004/0093057 A1 | 5/2004 | Bolduc et al. |
| 2004/0127916 A1 | 7/2004 | Bolduc et al. |
| 2004/0138734 A1 | 7/2004 | Chobotov et al. |
| 2004/0153143 A1 | 8/2004 | Quiachon et al. |
| 2004/0186566 A1 | 9/2004 | Hindrichs et al. |
| 2004/0206363 A1 | 10/2004 | Mccarthy et al. |
| 2004/0210304 A1 | 10/2004 | Seguin et al. |
| 2004/0243170 A1 | 12/2004 | Suresh et al. |
| 2004/0254594 A1 | 12/2004 | Alfaro |
| 2004/0260322 A1 | 12/2004 | Rudko et al. |
| 2004/0260383 A1 | 12/2004 | Stelter et al. |
| 2005/0038506 A1 | 2/2005 | Webler et al. |
| 2005/0043790 A1 | 2/2005 | Seguin |
| 2005/0070992 A1 | 3/2005 | Bolduc et al. |
| 2005/0113906 A9 | 5/2005 | Bolduc et al. |
| 2005/0154401 A1 | 7/2005 | Weldon et al. |
| 2005/0177180 A1 | 8/2005 | Kaganov et al. |
| 2005/0187613 A1 | 8/2005 | Bolduc |
| 2005/0197716 A1 | 9/2005 | Sharkey et al. |
| 2005/0215874 A1 | 9/2005 | Wang et al. |
| 2005/0240258 A1 | 10/2005 | Bolduc et al. |
| 2005/0240260 A1 | 10/2005 | Bolduc |
| 2006/0100640 A1* | 5/2006 | Bolduc ............ A61B 17/00234 606/108 |
| 2006/0111692 A1 | 5/2006 | Hlavka et al. |
| 2006/0184224 A1 | 8/2006 | Angel |
| 2006/0253186 A1 | 11/2006 | Bates |
| 2006/0259125 A1 | 12/2006 | Peacock, III |
| 2006/0287661 A1 | 12/2006 | Bolduc et al. |
| 2007/0021753 A1 | 1/2007 | Bolduc et al. |
| 2007/0021829 A1 | 1/2007 | Bolduc et al. |
| 2007/0032860 A1 | 2/2007 | Brooks et al. |
| 2007/0073389 A1 | 3/2007 | Bolduc et al. |
| 2007/0083255 A1 | 4/2007 | Chiang et al. |
| 2008/0065117 A1 | 3/2008 | Bolduc et al. |
| 2008/0065189 A1 | 3/2008 | Bolduc |
| 2008/0065191 A1 | 3/2008 | Bolduc et al. |
| 2008/0097489 A1 | 4/2008 | Goldfarb et al. |
| 2008/0139886 A1* | 6/2008 | Tatsuyama ............ A61B 1/0055 600/146 |
| 2008/0132996 A1 | 7/2008 | Drasler et al. |
| 2009/0082852 A1 | 3/2009 | Bolduc et al. |
| 2009/0112302 A1 | 4/2009 | Stafford |
| 2009/0112303 A1 | 4/2009 | Bolduc |
| 2009/0138072 A1 | 5/2009 | Gendreau |
| 2009/0177041 A1* | 7/2009 | Stefanchik ......... A61B 1/00073 600/146 |
| 2010/0094400 A1 | 4/2010 | Bolduc et al. |
| 2011/0087320 A1 | 4/2011 | Bolduc et al. |
| 2011/0238088 A1 | 9/2011 | Bolduc et al. |
| 2011/0276062 A1 | 11/2011 | Bolduc |
| 2012/0059450 A1 | 3/2012 | Chiang et al. |
| 2012/0065661 A1 | 3/2012 | Bolduc |
| 2012/0316578 A1 | 12/2012 | Bolduc et al. |
| 2014/0194902 A1 | 7/2014 | Bolduc et al. |
| 2014/0214051 A1 | 7/2014 | Bolduc |
| 2015/0127015 A1 | 5/2015 | Bolduc et al. |

FOREIGN PATENT DOCUMENTS

| | | |
|---|---|---|
| AU | 2008243229 A1 | 12/2008 |
| AU | 2004287355 B2 | 6/2011 |
| AU | 2006305688 B2 | 12/2012 |
| AU | 2011253682 B9 | 1/2014 |
| AU | 2011224089 B2 | 7/2014 |
| CA | 2265131 | 9/1999 |
| CA | 2344252 A1 | 3/2000 |
| CA | 2729464 A1 | 6/2003 |
| CA | 2539265 A1 | 5/2005 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2554022 A1 | 11/2012 |
| CA | 2546721 C | 9/2013 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1870951 A | 11/2006 |
| CN | 1997318 A | 7/2007 |
| CN | 101151002 A | 3/2008 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |
| CN | 101466316 B | 6/2012 |
| DE | 3333427 C2 | 5/1991 |
| DE | 69228184 T2 | 9/1999 |
| DE | 10034105 C1 | 4/2002 |
| DE | 10297483 T5 | 12/2004 |
| EP | 0321912 A1 | 6/1989 |
| EP | 0663184 A1 | 7/1995 |
| EP | 0835642 B1 | 8/2002 |
| EP | 1369098 A1 | 12/2003 |

(56) References Cited

FOREIGN PATENT DOCUMENTS

| | | |
|---|---|---|
| EP | 1440673 A1 | 7/2004 |
| EP | 1448117 A1 | 8/2004 |
| EP | 1675528 A2 | 7/2006 |
| EP | 1725172 A2 | 11/2006 |
| EP | 1734872 A1 | 12/2006 |
| EP | 1948080 A2 | 7/2008 |
| EP | 2119416 A1 | 11/2009 |
| EP | 2349086 A1 | 8/2011 |
| EP | 2349087 A1 | 8/2011 |
| FR | 2299548 A1 | 8/1976 |
| FR | 2865926 A1 | 8/2005 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2001526574 A | 12/2001 |
| JP | 2002526193 A | 8/2002 |
| JP | 2005046648 | 2/2005 |
| JP | 2005510293 A | 4/2005 |
| JP | 2005510303 | 4/2005 |
| JP | 2007508894 A | 4/2007 |
| JP | 2007508895 A | 4/2007 |
| JP | 2007523694 A | 8/2007 |
| JP | 2007535339 A | 12/2007 |
| JP | 2009512497 A | 3/2009 |
| JP | 2009512498 A | 3/2009 |
| JP | 2009512499 A | 3/2009 |
| JP | 2009078172 A | 4/2009 |
| JP | 2009095684 A | 5/2009 |
| JP | 2009106763 A | 5/2009 |
| JP | 2009106768 A | 5/2009 |
| JP | 2009106775 A | 5/2009 |
| JP | 2009112827 A | 5/2009 |
| JP | 2009519046 A | 5/2009 |
| JP | 4405262 B2 | 1/2010 |
| JP | 10506026 A | 2/2010 |
| JP | 2010051786 A | 3/2010 |
| JP | 4465359 B2 | 5/2010 |
| JP | 2011062570 A | 3/2011 |
| JP | 4699445 B2 | 6/2011 |
| WO | WO-93/00868 A1 | 1/1993 |
| WO | WO-95/21592 A1 | 8/1995 |
| WO | WO-96/03925 A1 | 2/1996 |
| WO | WO-97/03616 A1 | 2/1997 |
| WO | WO 1997003616 A1 | 2/1997 |
| WO | WO-97/12562 A1 | 4/1997 |
| WO | WO-97/17039 A1 | 5/1997 |
| WO | WO-97/17913 A1 | 5/1997 |
| WO | WO-98/11814 A2 | 3/1998 |
| WO | WO-98/53761 A1 | 12/1998 |
| WO | WO-99/30637 A1 | 6/1999 |
| WO | WO-99/33402 A1 | 7/1999 |
| WO | WO-99/33402 A9 | 9/1999 |
| WO | WO-99/53845 A1 | 10/1999 |
| WO | WO-1999/053845 A1 | 10/1999 |
| WO | WO-00/16701 A1 | 3/2000 |
| WO | WO-00/35350 A1 | 6/2000 |
| WO | WO-00/64357 A1 | 11/2000 |
| WO | WO-01/60432 A1 | 8/2001 |
| WO | WO-03/032870 A1 | 4/2003 |
| WO | WO-03/045283 A1 | 6/2003 |
| WO | WO-03/045467 A2 | 6/2003 |
| WO | WO-03/045467 A3 | 6/2003 |
| WO | WO-03/079935 A1 | 10/2003 |
| WO | WO-2004/008975 A1 | 1/2004 |
| WO | WO-2004/021872 A2 | 3/2004 |
| WO | WO-2005/032333 A2 | 4/2005 |
| WO | WO-2005/032333 A3 | 4/2005 |
| WO | WO-2005/037076 A2 | 4/2005 |
| WO | WO-2005/044073 A2 | 5/2005 |
| WO | WO-2005/044073 A3 | 5/2005 |
| WO | WO-2005/044147 A1 | 5/2005 |
| WO | WO-2005/044148 A1 | 5/2005 |
| WO | WO-2005/067660 A2 | 7/2005 |
| WO | WO-2005/081936 A2 | 9/2005 |
| WO | WO-2005/081936 A3 | 9/2005 |
| WO | WO-2005/102181 A1 | 11/2005 |
| WO | WO-2005/067660 A3 | 4/2007 |
| WO | WO-2007/046953 A2 | 4/2007 |
| WO | WO-2007/046953 A3 | 4/2007 |
| WO | WO-2007/046954 A2 | 4/2007 |
| WO | WO-2007/046954 A3 | 4/2007 |
| WO | WO-2007/046955 A2 | 4/2007 |
| WO | WO-2007/046955 A3 | 4/2007 |
| WO | WO-2007/047023 A2 | 4/2007 |
| WO | WO-2007/047023 A3 | 4/2007 |
| WO | WO-2007/053233 A2 | 5/2007 |
| WO | WO-2007/053233 A3 | 1/2008 |
| WO | WO-2010/004856 A1 | 1/2010 |
| WO | WO-2010/044851 A1 | 4/2010 |
| WO | WO-2010/044854 A1 | 4/2010 |
| WO | WO-2010/044855 A1 | 4/2010 |
| WO | WO-2010/044856 A1 | 4/2010 |

OTHER PUBLICATIONS

"U.S. Appl. No. 10/307,226, Appeal Brief filed Oct. 14, 2010", 15 pgs.

"U.S. Appl. No. 10/307,226, Final Office Action dated Jun. 27, 2008", 6 pgs.

"U.S. Appl. No. 10/307,226, Final Office Action dated Dec. 12, 2006", 5 pgs.

"U.S. Appl. No. 10/307,226, Non Final Office Action dated Mar. 13, 2006", 6 pgs.

"U.S. Appl. No. 10/307,226, Non Final Office Action dated Jun. 12, 2007", 5 pgs.

"U.S. Appl. No. 10/307,226, Non Final Office Action dated Sep. 9, 2009", 16 pgs.

"U.S. Appl. No. 10/307,226, Notice of Allowance dated Jul. 22, 2011", 8 pgs.

"U.S. Appl. No. 10/307,226, Preliminary Amendment filed Jul. 22, 2005", 3 pgs.

"U.S. Appl. No. 10/307,226, PTO Response to 312 Amendment dated Nov. 10, 2011", 3 pgs.

"U.S. Appl. No. 10/307,226, Response filed Apr. 9, 2007 to Final Office Action dated Dec. 12, 2006", 7 pgs.

"U.S. Appl. No. 10/307,226, Response filed Jun. 23, 2009 to Final Office Action dated Jun. 27, 2008", 10 pgs.

"U.S. Appl. No. 10/307,226, Response filed Sep. 15, 2006 to Non Final Office Action dated Mar. 13, 2006", 6 pgs.

"U.S. Appl. No. 10/307,226, Response filed Dec. 14, 2007 to Non Final Office Action dated Jun. 12, 2007", 7 pgs.

"U.S. Appl. No. 10/669,881, Final Office Action dated Jan. 25, 2008", 7 pgs.

"U.S. Appl. No. 10/669,881, Non Final Office Action dated Jan. 27, 2006", 5 pgs.

"U.S. Appl. No. 10/669,881, Notice of Allowance dated Oct. 8, 2008", 16 pgs.

"U.S. Appl. No. 10/669,881, Preliminary Amendment dated May 6, 2005", 3 pgs.

"U.S. Appl. No. 10/669,881, Response filed Mar. 11, 2008 to Final Office Action dated Jan. 25, 2008", 8 pgs.

"U.S. Appl. No. 10/669,881, Response filed May 15, 2006 to Non Final Office Action dated Jan. 27, 2006", 9 pgs.

"U.S. Appl. No. 10/669,881, Response filed Sep. 7, 2007 to Restriction Requirement dated Jun. 19, 2007", 4 pgs.

"U.S. Appl. No. 10/669,881, Response filed Oct. 2, 2006 to Restriction Requirement dated Jul. 27, 2006", 6 pgs.

"U.S. Appl. No. 10/669,881, Restriction Requirement dated Jul. 27, 2006", 5 pgs.

"U.S. Appl. No. 10/669,881, Restriction Requirement dated Jun. 19, 2007", 5 pgs.

"U.S. Appl. No. 10/692,282, Non Final Office Action dated Aug. 30, 2005", 6 pgs.

"U.S. Appl. No. 10/692,282, Notice of Allowance dated Jun. 13, 2006", 6 pgs.

"U.S. Appl. No. 10/692,282, Response filed Feb. 28, 2006 to Non Final Office Action dated Aug. 30, 2005", 5 pgs.

(56) References Cited

OTHER PUBLICATIONS

"U.S. Appl. No. 10/693,255, Examiner Interview Summary dated Feb. 17, 2005", 3 pgs.
"U.S. Appl. No. 10/693,255, Non Final Office Action dated Dec. 9, 2004", 6 pgs.
"U.S. Appl. No. 10/693,255, Notice of Allowance dated Mar. 9, 2005", 9 pgs.
"U.S. Appl. No. 10/693,255, Response filed Feb. 17, 2005 to Non Final Office Action dated Dec. 9, 2004", 6 pgs.
"U.S. Appl. No. 10/752,435, Final Office Action dated May 14, 2010", 8 pgs.
"U.S. Appl. No. 10/752,435, Final Office Action dated Jul. 12, 2007", 8 pgs.
"U.S. Appl. No. 10/752,435, Final Office Action dated Dec. 8, 2008", 8 pgs.
"U.S. Appl. No. 10/752,435, Non Final Office Action dated Mar. 18, 2008", 7 pgs.
"U.S. Appl. No. 10/752,435, Non Final Office Action dated Jul. 21, 2009", 7 pgs.
"U.S. Appl. No. 10/752,435, Non Final Office Action dated Oct. 19, 2006", 17 pgs.
"U.S. Appl. No. 10/752,435, Response filed Jan. 9, 2008 to Final Office Action dated Jul. 12, 2007", 10 pgs.
"U.S. Appl. No. 10/752,435, Response filed Jan. 25, 2010 to Non Final Office Action dated Jul. 21, 2009", 9 pgs.
"U.S. Appl. No. 10/752,435, Response filed Apr. 9, 2007 to Non Final Office Action dated Oct. 19, 2006", 13 pgs.
"U.S. Appl. No. 10/752,435, Response filed May 12, 2009 to Final Office Action dated Dec. 8, 2008", 9 pgs.
"U.S. Appl. No. 10/752,435, Response filed Sep. 19, 2008 to Non Final Office Action dated Mar. 18, 2008", 7 pgs.
"U.S. Appl. No. 10/786,465, Supplemental Amendment filed Mar. 18, 2008", 8 pgs.
"Application U.S. Appl. No. 10/808,216, Preliminary Amendment filed Jun. 15, 2005", 3 pgs.
"U.S. Appl. No. 11/166,428, Final Office Action dated Jan. 12, 2009", 10 pgs.
"U.S. Appl. No. 11/166,428, Final Office Action dated Mar. 16, 2010", 8 pgs.
"U.S. Appl. No. 11/166,428, Non Final Office Action dated May 14, 2008", 6 pgs.
"U.S. Appl. No. 11/166,428, Non Final Office Action dated Jun. 16, 2009", 10 pgs.
"U.S. Appl. No. 11/166,428, Response filed May 12, 2009 to Final Office Action dated Jan. 12, 2009", 6 pgs.
"U.S. Appl. No. 11/166,428, Response filed Nov. 17, 2008 to Non Final Office Action dated May 14, 2008", 6 pgs.
"U.S. Appl. No. 11/166,428, Response filed Dec. 22, 2009 to Non Final Office Action dated Dec. 16, 2009", 8 pgs.
"U.S. Appl. No. 11/254,619, Advisory Action dated Sep. 24, 2014", 3 pgs.
"U.S. Appl. No. 11/254,619, Examiner Interview Summary dated Sep. 18, 2014", 3 pgs.
"U.S. Appl. No. 11/254,619, Final Office Action dated Jun. 19, 2014", 17 pgs.
"U.S. Appl. No. 11/254,619, Final Office Action dated May 30, 2010", 10 pgs.
"U.S. Appl. No. 11/254,619, Final Office Action dated Oct. 20, 2011", 11 pgs.
"U.S. Appl. No. 11/254,619, Non Final Office Action dated Jan. 6, 2014", 19 pgs.
"U.S. Appl. No. 11/254,619, Non Final Office Action dated Feb. 3, 2011", 8 pgs.
"U.S. Appl. No. 11/254,619, Non Final Office Action dated Oct. 1, 2009", 5 pgs.
"U.S. Appl. No. 11/254,619, Response filed Apr. 1, 2010 to Non Final Office Action dated Oct. 1, 2009", 5 pgs.
"U.S. Appl. No. 11/254,619, Response filed Apr. 20, 2012 to Final Office Action dated Oct. 20, 2011", 11 pgs.
"U.S. Appl. No. 11/254,619, Response filed May 6, 2014 to Non Final Office Action dated Jan. 6, 2014", 10 pgs.
"U.S. Appl. No. 11/254,619, Response filed Aug. 3, 2011 to Non Final Office Action dated Feb. 3, 2011 ", 13 pgs.
"U.S. Appl. No. 11/254,619, Response filed Sep. 15, 2014 to Final Office Action dated Jun. 19, 2014", 12 pgs.
"U.S. Appl. No. 11/254,619, Response filed Dec. 29, 2010 to Final Office Action dated Jun. 30, 2010", 12 pgs.
"U.S. Appl. No. 11/365,056, Final Office Action dated Dec. 9, 2010", 13 pgs.
"U.S. Appl. No. 11/365,056, Non Final Office Action dated Mar. 23, 2010", 11 pgs.
"U.S. Appl. No. 11/365,056, Response filed Sep. 28, 2010 to Non Final Office Action dated Mar. 23, 2010", 5 pgs.
"U.S. Appl. No. 11/365,056, Response filed Dec. 10, 2009 to Restriction Requirement dated Jun. 10, 2009", 44 pgs.
"U.S. Appl. No. 11/365,056, Restriction Requirement dated Jun. 10, 2009", 5 pgs.
"U.S. Appl. No. 11/488,305, Final Office Action dated Aug. 14, 2014", 11 pgs.
"U.S. Appl. No. 11/488,305, Non Final Office Action dated Jan. 29, 2014", 10 pgs.
"U.S. Appl. No. 11/488,305, Response filed Apr. 29, 2014 to Non Final Office Action dated Jan. 29, 2014", 9 pgs.
"U.S. Appl. No. 11/540,428, Response filed May 12, 2011 to Non Final Office Action dated Nov. 12, 2010", 12 pgs.
"U.S. Appl. No. 11/540,428, Response filed Oct. 1, 2010 to Restriction Requirement dated Mar. 29, 2010", 6 pgs.
"U.S. Appl. No. 11/540,428, Restriction Requirement dated Mar. 29, 2010", 9 pgs.
"U.S. Appl. No. 11/580,584, Appeal Brief filed Nov. 15, 2010", 11 pgs.
"U.S. Appl. No. 11/580,584, Final Office Action dated Jan. 22, 2009", 9 pgs.
"U.S. Appl. No. 11/580,584, Final Office Action dated Oct. 16, 2009", 8 pgs.
"U.S. Appl. No. 11/580,584, Non Final Office Action dated Apr. 18, 2008", 6 pgs.
"U.S. Appl. No. 11/580,584, Notice of Allowance dated Feb. 4, 2011 ", 7 pgs.
"U.S. Appl. No. 11/580,584, Response filed Jul. 22, 2009 to Final Office Action dated Jan. 22, 2009", 6 pgs.
"U.S. Appl. No. 11/580,584, Response filed Oct. 20, 2008 to Non Final Office Action dated Apr. 18, 2008", 5 pgs.
"U.S. Appl. No. 11/633,724, Final Office Action dated Jun. 22, 2010", 6 pgs.
"U.S. Appl. No. 11/633,724, Response filed Jun. 8, 2010 to Final Office Action dated Dec. 8, 2009", 4 pgs.
"U.S. Appl. No. 11/978,753, Response filed Mar. 3, 2011 to Non Final Office Action dated Sep. 3, 2010", 9 pgs.
"U.S. Appl. No. 11/981,112, Advisory Action dated Jan. 31, 2014", 3 pgs.
"U.S. Appl. No. 11/981,112, Final Office Action dated Apr. 29, 2010", 9 pgs.
"U.S. Appl. No. 11/981,112, Final Office Action dated Oct. 8, 2013", 9 pgs.
"U.S. Appl. No. 11/981,112, Final Office Action dated Oct. 24, 2014", 7 pgs.
"U.S. Appl. No. 11/981,112, Non Final Office Action dated Jul. 8, 2009", 11 pgs.
"U.S. Appl. No. 11/981,112, Response file dJan. 18, 2014 to Final Office Action dated Oct. 8, 2013", 11 pgs.
"U.S. Appl. No. 11/981,112, Response filed Jan. 6, 2010 to Non Final Office Action dated Jul. 8, 2009", 7 pgs.
"U.S. Appl. No. 11/981,112, Response filed Jan. 12, 2014 to Final Office Action dated Oct. 24, 2014", 9 pgs.
"U.S. Appl. No. 11/981,112, Response filed Nov. 1, 2010 to Final Office Action dated Apr. 29, 2010", 7 pgs.
"U.S. Appl. No. 11/981,112, Examiner Interview Summary dated Jul. 3, 2014", 3 pgs.
"U.S. Appl. No. 11/981,112, Non Final Office Action dated Feb. 28, 2014", 9 pgs.

(56) References Cited

OTHER PUBLICATIONS

"U.S. Appl. No. 11/981,112, Response filed Jun. 27, 2014 to Non Final Office Action dated Feb. 28, 2014", 11 pgs.
"U.S. Appl. No. 12/288,032, Restriction Requirement dated Nov. 4, 2011", 9 pgs.
"U.S. Appl. No. 12/288,034, Advisory Action dated Feb. 25, 2014", 3 pgs.
"U.S. Appl. No. 12/288,034, Final Office Action dated Nov. 4, 2013", 8 pgs.
"U.S. Appl. No. 12/288,034, Final Office Action dated Dec. 1, 2014", 8 pgs.
"U.S. Appl. No. 12/288,034, Non Final Office Action dated May 8, 2014", 8 pgs.
"U.S. Appl. No. 12/288,034, Response filed Feb. 4, 2014 to Final Office Action dated Nov. 4, 2013", 12 pgs.
"U.S. Appl. No. 12/288,034, Response filed May 1, 2012 to Restriction Requirement dated Nov. 4, 2011", 4 pgs.
"U.S. Appl. No. 12/288,034, Response filed Aug. 1, 2014 to Non Final Office Action dated May 8, 2014", 11 pgs.
"U.S. Appl. No. 12/288,034, Response filed Dec. 21, 2012 to Non Final Office Action dated Jun. 22, 2012", 12 pgs.
"U.S. Appl. No. 12/288,034, Restriction Requirement dated Nov. 3, 2011", 9 pgs.
"U.S. Appl. No. 12/288,045, Restriction Requirement dated Nov. 16, 2011", 9 pgs.
"U.S. Appl. No. 12/315,015, Advisory Action dated Apr. 7, 2014", 3 pgs.
"U.S. Appl. No. 12/315,015, Advisory Action dated Sep. 12, 2012", 3 pgs.
"U.S. Appl. No. 12/315,015, Examiner Interview Summary dated Nov. 28, 2014", 3 pgs.
"U.S. Appl. No. 12/315,015, Final Office Action dated Jan. 28, 2014", 8 pgs.
"U.S. Appl. No. 12/315,015, Final Office Action dated Dec. 5, 2014", 9 pgs.
"U.S. Appl. No. 12/315,015, Non Final Office Action dated Mar. 30, 2015", 10 pgs.
"U.S. Appl. No. 12/315,015, Non Final Office Action dated Aug. 4, 2014", 7 pgs.
"U.S. Appl. No. 12/315,015, Non Final Office Action dated Sep. 27, 2013", 7 pgs.
"U.S. Appl. No. 12/315,015, Preliminary Amendment filed Mar. 10, 2009", 3 pgs.
"U.S. Appl. No. 12/315,015, Response filed Mar. 5, 2015 to Final Office Action dated Dec. 5, 2014", 13 pgs.
"U.S. Appl. No. 12/315,015, Response filed Mar. 28, 2014 to Final Office Action dated Jan. 24, 2014", 5 pgs.
"U.S. Appl. No. 12/315,015, Response filed Apr. 6, 2012 to Non Final Office Action dated Oct. 6, 2011", 12 pgs.
"U.S. Appl. No. 12/315,015, Response filed Jun. 17, 2014 to Final Office Action dated Jan. 28, 2014", 7 pgs.
"U.S. Appl. No. 12/315,015, Response filed Aug. 27, 2012 to Final Office Action dated Apr. 26, 2012", 6 pgs.
"U.S. Appl. No. 12/315,015, Response filed Nov. 4, 2014 to Non-Final Office Action dated Aug. 4, 2014", 7 pgs.
"U.S. Appl. No. 12/315,015, Response filed Dec. 27, 2013 to Non Final Office Action dated Sep. 27, 2013", 7 pgs.
"U.S. Appl. No. 12/653,219, Non Final Office Action dated May 30, 2012", 16 pgs.
"U.S. Appl. No. 12/917,842, Notice of Allowance dated Aug. 27, 2013", 6 pgs.
"U.S. Appl. No. 12/917,842, Notice of Allowance dated Dec. 2, 2013", 7 pgs.
"U.S. Appl. No. 12/942,232, Advisory Action dated Aug. 7, 2014", 3 pgs.
"U.S. Appl. No. 12/942,232, Final Office Action dated May 22, 2014", 17 pgs.
"U.S. Appl. No. 12/942,232, Non Final Office Action dated Oct. 9, 2013", 13 pgs.
"U.S. Appl. No. 12/942,232, Response filed Jan. 9, 2014 to Non Final Office Action dated Oct. 9, 2013", 11 pgs.
"U.S. Appl. No. 12/942,232, Response filed Jul. 21, 2014 to Final Office Action dated May 22, 2014", 11 pgs.
"U.S. Appl. No. 13/157,242, Non Final Office Action dated Oct. 31, 2013", 6 pgs.
"U.S. Appl. No. 13/157,242, Notice of Allowance dated Jan. 14, 2015", 8 pgs.
"U.S. Appl. No. 13/157,242, Notice of Allowance dated Feb. 26, 2014", 8 pgs.
"U.S. Appl. No. 13/157,242, Notice of Allowance dated May 9, 2014", 8 pgs.
"U.S. Appl. No. 13/157,242, Notice of Allowance dated Aug. 21, 2014", 8 pgs.
"U.S. Appl. No. 13/157,242, Response filed Jan. 28, 2014 to Non Final Office Action dated Oct. 31, 2013", 11 pgs.
"U.S. Appl. No. 13/162,384, Advisory Action dated Nov. 15, 2013", 3 pgs.
"U.S. Appl. No. 13/162,384, Examiner Interview Summary dated Oct. 22, 2014", 3 pgs.
"U.S. Appl. No. 13/162,384, Examiner Interview Summary dated Feb. 24, 2015", 1 pg.
"U.S. Appl. No. 13/162,384, Final Office Action dated Aug. 27, 2013", 14 pgs.
"U.S. Appl. No. 13/162,384, Non Final Office Action dated Feb. 24, 2015", 14 pgs.
"U.S. Appl. No. 13/162,384, Non Final Office Action dated Jul. 21, 2014", 15 pgs.
"U.S. Appl. No. 13/162,384, Response filed Oct. 18, 2013 to Final Office Action dated Aug. 27, 2013", 5 pgs.
"U.S. Appl. No. 13/162,384, Response filed Oct. 20, 2014 to Non Final Office Action dated Jul. 21, 2014", 12 pgs.
"U.S. Appl. No. 13/291,942, Advisory Action dated Mar. 21, 2014", 3 pgs.
"U.S. Appl. No. 13/291,942, Final Office Action dated Jan. 3, 2014", 10 pgs.
"U.S. Appl. No. 13/291,942, Final Office Action dated Feb. 26, 2015", 10 pgs.
"U.S. Appl. No. 13/291,942, Non Final Office Action dated Oct. 21, 2014", 10 pgs.
"U.S. Appl. No. 13/291,942, Preliminary Amendment filed Nov. 8, 2011", 3 pgs.
"U.S. Appl. No. 13/291,942, Response filed Jan. 20, 2015 to Non Final Office Action dated Oct. 21, 2014", 11 pgs.
"U.S. Appl. No. 13/291,942, Response filed Mar. 4, 2014 to Final Office Action dated Jan. 3, 2014", 10 pgs.
"U.S. Appl. No. 13/495,836, Notice of Allowance dated Dec. 4, 2013", 9 pgs.
"U.S. Appl. No. 13/495,836, Preliminary Amendment filed Jun. 13, 2012", 8 pgs.
"U.S. Appl. No. 13/495,836, Response filed Mar. 25, 2013 to Non Final Office Action dated Dec. 26, 2012", 9 pgs.
"U.S. Appl. No. 13/495,836, Response filed Nov. 5, 2013 to Non Final Office Action dated Aug. 5, 2013", 8 pgs.
"U.S. Appl. No. 14/210,683, Preliminary Amendment dated Mar. 24, 2014", 7 pgs.
"U.S. Appl. No. 14/230,469, Non Final Office Action dated May 7, 2015", 8 pgs.
"U.S. Appl. No. 14/595,928, Preliminary Amendment filed Jan. 14, 2015", 8 pgs.
"Australian Application Serial No. 2002351188, Office Action dated Mar. 30, 2007", 1 pg.
"Australian Application Serial No. 2002351188, Office Action dated Dec. 8, 2008", 3 pgs.
"Australian Application Serial No. 2004287354, Office Action dated Oct. 13, 2009", 2 pgs.
"Australian Application Serial No. 2004287355, European Search Report dated Oct. 14, 2009", 6 pgs.
"Australian Application Serial No. 2004287355, Office Action dated May 11, 2009", 2 pgs.
"Australian Application Serial No. 2005204615, Office Action dated Jan. 20, 2010", 4 pgs.

(56) References Cited

OTHER PUBLICATIONS

"Australian Application Serial No. 2005235108, Office Action dated Feb. 26, 2010", 3 pgs.
"Australian Application Serial No. 2006302908, Office Action dated Mar. 4, 2011", 8 pgs.
"Australian Application Serial No. 2006305688, First Examiner Report dated Mar. 10, 2011", 3 pgs.
"Australian Application Serial No. 2006305688, Response filed Oct. 22, 2012 to First Examiner Report dated Mar. 10, 2011", 16 pgs.
"Australian Application Serial No. 2006305689, Office Action dated Sep. 5, 2011", 3 pgs.
"Australian Application Serial No. 2006309241, Office Action dated Mar. 4, 2011", 6 pgs.
"Australian Application Serial No. 2008243229, First Examiner Report dated Apr. 13, 2010", 2 pgs.
"Australian Application Serial No. 2008243229, Response filed May 13, 2011 to Office Action dated Apr. 13, 2010", 15 pgs.
"Australian Application Serial No. 2011224089, Response filed Mar. 21, 2014 to First Examiners Report dated Mar. 27, 2013", 74pgs.
"Canadian Application Serial No. 2,464,900, Office Action dated Sep. 29, 2009", 3 pgs.
"Canadian Application Serial No. 2,539,585, Office Action dated Aug. 31, 2010", 2 pgs.
"Canadian Application Serial No. 2,539,585, Office Action dated Sep. 19, 2012", 2 pgs.
"Canadian Application Serial No. 2,546,681, Office Action dated Feb. 25, 2011", 3 pgs.
"Canadian Application Serial No. 2,546,721, Office Action dated Feb. 25, 2011", 3 pgs.
"Canadian Application Serial No. 2,546,721, Office Action dated Aug. 31, 2010", 2 pgs.
"Canadian Application Serial No. 2,546,721, Response filed Aug. 1, 2012 to Office Action dated Feb. 25, 2011 ", 9 pgs.
"Canadian Application Serial No. 2,551,685, Office Action dated Jan. 17, 2011", 3 pgs.
"Canadian Application Serial No. 2,554,022, Office Action dated Jun. 22, 2011", 3 pgs.
"Canadian Application Serial No. 2,554,022, Office Action dated Aug. 31, 2010", 2 pgs.
"Canadian Application Serial No. 2,558,317, Office Action dated Aug. 31, 2010", 2 pgs.
"Canadian Application Serial No. 2,558,317, Office Action dated Sep. 28, 2011", 3 pgs.
"Canadian Application Serial No. 2,626,403, Response filed Feb. 12, 2014 to Office Action dated Apr. 2, 2013", 20 pgs.
"Chinese Application Serial No. 02823581. 9, Response filed May 19, 2008 to Office Action dated Apr. 18, 2008", (W/ English Translation), 38 pgs.
"Chinese Application Serial No. 02823581.9, Office Action dated Mar. 1, 2006", 7 pgs.
"Chinese Application Serial No. 02823581.9, Office Action dated Apr. 18, 2008", 6 pgs.
"Chinese Application Serial No. 02823581.9, Office Action dated Aug. 8, 2007", 4 pgs.
"Chinese Application Serial No. 02823581.9, Office Action dated Nov. 17, 2006", 7 pgs.
"Chinese Application Serial No. 02823581.9, Response filed Jan. 31, 2007 to Office Action dated Nov. 17, 2006", 8 pgs.
"Chinese Application Serial No. 02823581.9, Response filed Apr. 7, 2006 to Office Action dated Mar. 1, 2006", 4 pgs.
"Chinese Application Serial No. 02823581.9, Response filed Dec. 3, 2007 to Office Action dated Aug. 8, 2007", 6 pgs.
"Chinese Application Serial No. 200480027649.7, Office Action dated Jun. 23, 2008", w/English translation, 5 pgs.
"Chinese Application Serial No. 200480027649.7, Office Action dated Sep. 4, 2009", w/English translation, 18 pgs.
"Chinese Application Serial No. 200480027649.7, Office Action dated Dec. 24, 2010", w/English translation, 6 pgs.
"Chinese Application Serial No. 200480027649.7, Response filed Jan. 19, 2010 to Office Action dated Sep. 4, 2009", 5 pgs.
"Chinese Application Serial No. 200480027649.7, Response filed Mar. 8, 2011 to Office Action dated Dec. 24, 2010", w/English translation, 7 pgs.
"Chinese Application Serial No. 200480031226.2, Office Action dated Jan. 23, 2009", w/English translation, 9 pgs.
"Chinese Application Serial No. 200480031226.2, Office Action dated Apr. 27, 2010", (W/ English Translation), 7 pgs.
"Chinese Application Serial No. 200480031226.2, Office Action dated Dec. 21, 2010", (W/ English Translation), 10 pgs.
"Chinese Application Serial No. 200480031226.2, Response filed Feb. 25, 2011 to Office Action dated Dec. 21, 2010", (Wi English Translation), 18 pgs.
"Chinese Application Serial No. 200480031226.2, Response filed May 22, 2009 to Office Action dated Jan. 23, 2009", 5 pgs.
"Chinese Application Serial No. 200480031226.2, Response filed Jul. 12, 2010 to Office Action dated Apr. 27, 2010", 5 pgs.
"Chinese Application Serial No. 200580002026.9, Office Action dated Jun. 19, 2009", (W/ English Translation), 12 pgs.
"Chinese Application Serial No. 200580002026.9, Response filed Jan. 4, 2010 to Office Action dated Jun. 19, 2009", 10 pgs.
"Chinese Application Serial No. 200580006169.7, Office Action dated Mar. 1, 2010", w/English translation, 12 pgs.
"Chinese Application Serial No. 200580006169.7, Response filed Jul. 14, 2010 to Office Action dated Mar. 1, 2010", w/English translation, 32 pgs.
"Chinese Application Serial No. 200680038882.4, Office Action dated May 11, 2010", (W/ English Translation), 18 pgs.
"Chinese Application Serial No. 200680046854.7, Office Action dated Apr. 14, 2010", (W/ English Translation), 18 pgs.
"Chinese Application Serial No. 200680046854.7, Response filed Sep. 26, 2010 to Office Action dated Apr. 14, 2010", 10 pgs.
"Chinese Application Serial No. 200680047552.1, Office Action dated Jun. 4, 2010", (W/ English Translation), 7 pgs.
"Chinese Application Serial No. 200680047552.1, Response filed Dec. 20, 2010 to Office Action dated Jun. 4, 2010", 10 pgs.
"Chinese Application Serial No. 200810210922.X, Office Action dated Jan. 19, 2012", (W/ English Translation), 6 pgs.
"Chinese Application Serial No. 200810210922.X, Office Action dated Apr. 2, 2010", (W/ English Translation), 4 pgs.
"Chinese Application Serial No. 200810210922.X, Office Action dated Aug. 23, 2011 ", 6 pgs.
"Chinese Application Serial No. 200810210922.X, Response filed Jun. 1, 2012 to Office Action dated Jan. 19, 2012", 5 pgs.
"Chinese Application Serial No. 200810210922.X, Response filed Aug. 12, 2010 to Office Action dated Apr. 2, 2010", 10 pgs.
"Chinese Application Serial No. 200910139527.1, Office Action dated Jul. 12, 2010", w/English translation, 9 pgs.
"Chinese Application Serial No. 200910139527.1, Response filed Nov. 28, 2011 to Office Action dated Jul. 12, 2010", 9 pgs.
"European Application Serial No. 02789196.9, European Search Report dated Aug. 14, 2009", 5 pgs.
"European Application Serial No. 02789196.9, Office Action dated Feb. 6, 2012", 4 pgs.
"European Application Serial No. 02789196.9, Office Action dated Mar. 7, 2012", 3 pgs.
"European Application Serial No. 02789196.9, Office Action dated Apr. 19, 2010", 4 pgs.
"European Application Serial No. 02789196.9, Office Action dated Jul. 14, 2011", 3 pgs.
"European Application Serial No. 02789196.9, Response filed Jan. 18, 2012 to Office Action dated Jul. 14, 2011", 19 pgs.
"European Application Serial No. 02789196.9, Response filed Feb. 16, 2012 to Office Action dated Feb. 6, 2012", 9 pgs.
"European Application Serial No. 02789196.9, Response filed Apr. 5, 2012 to Office Action dated Mar. 7, 2012", 5 pgs.
"European Application Serial No. 02789196.9, Response filed Oct. 25, 2010 to Office Action dated Apr. 19, 2010", 16 pgs.
"European Application Serial No. 04788653.6, European Search Report dated Aug. 6, 2014", 3 pgs.
"European Application Serial No. 04788653.6, Examination Notification Art. 94(3) dated Mar. 3, 2015", 4 pgs.

(56) References Cited

OTHER PUBLICATIONS

"European Application Serial No. 04788653.6, Office Action dated May 19, 2006", 2 pgs.
"European Application Serial No. 04788653.6, Response filed Oct. 21, 2014 to European Search Report dated Aug. 6, 2014", 4 pgs.
"European Application Serial No. 05704902.5, European Search Report dated Aug. 29, 2011", 3 pgs.
"European Application Serial No. 05713941.2, European Search Report dated Apr. 10, 2014", 6 pgs.
"European Application Serial No. 05713941.2, Examination Notification Art. 94(3) dated Jun. 5, 201414", 7 pgs.
"European Application Serial No. 05713941.2, Office Action dated Dec. 13, 2007", 2 pgs.
"European Application Serial No. 05713941.2, Response filed Dec. 22, 2014 to Examination Notification Art. 94(3) dated Jun. 5, 2014", 15 pgs.
"European Application Serial No. 05723408.0, Examination Notification Art. 94(3) dated Jul. 10, 2014", 6 pgs.
"European Application Serial No. 05723408.0, Response filed Jan. 19, 2015 to Examination Notification Art. 94(3) dated Jul. 10, 2014", 16 pgs.
"European Application Serial No. 06802578.2, European Search Report dated Mar. 7, 2013", 10 pgs.
"European Application Serial No. 06802580.8, Extended European Search Report dated Sep. 24, 2013", 8 pgs.
"European Application Serial No. 06802580.8, Response filed Apr. 17, 2014 to Extended European Search Report dated Sep. 24, 2013", 2 pgs.
"European Application Serial No. 090753195, Extended European Search Report dated Oct. 14, 2009", 6 pgs.
"European Application Serial No. 09075319.5, Office Action dated Jan. 14, 2010", 1 pgs.
"European Application Serial No. 09075319.5, Office Action dated Oct. 14, 2010", 4 pgs.
"European Application Serial No. 09820886.1, Extended European Search Report dated Mar. 27, 2015", 8 pgs.
"European Application Serial No. 09075319.5, Response filed Feb. 21, 2011 to Office Action dated Oct. 14, 2010", 5 pgs.
"European Application Serial No. 09075319.5, Response filed Jul. 20, 2010 to Office Action dated Jan. 14, 2010", 13 pgs.
"German Application Serial No. 10297483.7, Office Action dated Jan. 9, 2006", 4 pgs.
"German Application Serial No. 10297483.7, Office Action dated Jul. 8, 2006", 2 pgs.
"German Application Serial No. 10297483.7, Office Action mailed and Response filed Oct. 30, 2006", 8 pgs.
"German Application Serial No. 10297483.7, Response filed Jul. 7, 2006 to Office Action dated Jan. 9, 2006", 14 pgs.
"German Application Serial No. 10297483.7, Response filed Oct. 26, 2006 to Office Action dated Jul. 8, 2006", 3 pgs.
"Great Britain Application Serial No. 0411107 .6, Office Action dated Feb. 28, 2005", 3 pgs.
"Great Britain Application Serial No. 0411107 .6, Office Action dated Sep. 29, 2005", 1 pg.
"Great Britain Application Serial No. 0411107 .6, Response filed Aug. 23, 2005 to Office Action dated Feb. 28, 2005", 3 pgs.
"Great Britain Application Serial No. 0411107 .6, Response filed Oct. 31, 2005 to Office Action dated Sep. 29, 2005", 4 pgs.
"Great Britain Application Serial No. 0522152.8, Office Action dated Dec. 5, 2005", 5 pgs.
"Great Britain Application Serial No. 0522152.8, Response filed Apr. 26, 2006 to Office Action dated Dec. 5, 2005", 48 pgs.
"International Application Serial No. PCT/US2002/032753, International Preliminary Examination Report dated Aug. 16, 2004", 3 pgs.
"International Application Serial No. PCT/US2002/032753, International Search Report dated Mar. 6, 2003", 1 pg.
"International Application Serial No. PCT/US2004/027589, International Preliminary Report on Patentability dated Apr. 6, 2005", 4 pgs.
"International Application Serial No. PCT/US2004/027589, International Search Report dated Apr. 6, 2005", 1 pg.
"International Application Serial No. PCT/US2004/027589, Written Opinion dated Apr. 6, 2005", 3 pgs.
"International Application Serial No. PCT/US2004/027590, International Preliminary Examination Report dated Feb. 16, 2006", 3 pgs.
"International Application Serial No. PCT/US2004/027590, International Search Report dated Jan. 12, 2005", 1 pg.
"International Application Serial No. PCT/US2004/027590, Written Opinion dated Jan. 12, 2005", 3 pgs.
"International Application Serial No. PCT/U52005/00059, International Preliminary Report on Patentability dated May 18, 2007", 8 pgs.
"International Application Serial No. PCT/US2005/00059, International Search Report dated Jan. 5, 2007", 3 pgs.
"International Application Serial No. PCT/US2005/00059, Written Opinion dated Jan. 5, 2007", 8 pgs.
"International Application Serial No. PCT/US2005/005453, International Preliminary Report on Patentability dated Feb. 16, 2006", 3 pgs.
"International Application Serial No. PCT/US2005/005453, International Search Report dated Aug. 30, 2005", 1 pg.
"International Application Serial No. PCT/US2005/005453, International Written Opinion dated Aug. 30, 2005", 3 pgs.
"International Application Serial No. PCT/US2006/033747, International Preliminary Report on Patentability dated Mar. 1, 2011", 4 pgs.
"International Application Serial No. PCT/US2009/005604, International Preliminary Report on Patentability dated Jan. 13, 2011", 10 pgs.
"International Application Serial No. PCT/US2009/005607, International Preliminary Report on Patentability dated Jan. 9, 2011", 9 pgs.
"International Application Serial No. PCT/US2009/005607, International Search Report dated Dec. 11, 2009", 2 pgs.
"International Application Serial No. PCT/US2009/005607, Written Opinion dated Dec. 11, 2009", 6 pgs.
"International Application Serial No. PCT/US2009/005609, International Preliminary Report on Patentability dated Jan. 9, 2011",9 pgs.
"Japanese Application Serial No. 2006-528036, Office Action dated Jan. 19, 2010", 3 pgs.
"Japanese Application Serial No. 2006-528036, Office Action dated Feb. 26, 2009", w/English translation, 5 pgs.
"Japanese Application Serial No. 2006-528036, Office Action dated Jun. 23, 2008", w/English translation, 5 pgs.
"Japanese Application Serial No. 2006-528036, Response filed Dec. 25, 2008 to Office Action dated Jun. 23, 2008", w/English translation, 9 pgs.
"Japanese Application Serial No. 2006-536616, Office Action dated Jun. 23, 2008", (W/ English Translation), 8 pgs.
"Japanese Application Serial No. 2006-536616, Response filed Dec. 19, 2008 to Office Action dated Jun. 23, 2008", (W/ English Translation), 9 pgs.
"Japanese Application Serial No. 2006-536617, Office Action dated Jun. 17, 2008", (W/ English Translation), 3 pgs.
"Japanese Application Serial No. 2006-536617, Response filed May 12, 2009 to Office Action dated Jun. 17, 2008", (W/ English Translation), 19 pgs.
"Japanese Application Serial No. 2006-547608, Office Action dated Jun. 23, 2008", (W/ English Translation), 5 pgs.
"Japanese Application Serial No. 2006-547608, Respone filed Dec. 19, 2008 to Office Action dated Jun. 23, 2008", (Wi English Translation), 10 pgs.
"Japanese Application Serial No. 2007500928, Office Action dated Jul. 1, 2010", w/English translation, 10 pgs.
"Japanese Application Serial No. 2007504965, Office Action dated Mar. 7, 2012", w/English translation, 4 pgs.
"Japanese Application Serial No. 2007504965, Office Action dated Jun. 14, 2011 ", w/English translation, 4 pgs.
"Japanese Application Serial No. 2007504965, Office Action dated Sep. 14, 2010", English translation, 1 pg.

(56) References Cited

OTHER PUBLICATIONS

"Japanese Application Serial No. 2007504965, Response filed Mar. 11, 2011 to Office Action dated Sep. 14, 2010", 8 pgs.
"Japanese Application Serial No. 2008-306790, Office Action dated May 31, 2011 ", 1 pg.
"Japanese Application Serial No. 2008-306790, Response filed Nov. 29, 2011 to Office Action dated May 8, 2012", 2 pgs.
"Japanese Application Serial No. 2008-306790, Response filed Nov. 29, 2011 to Office Action dated May 31, 2011 ", (W/ English Translation), 12 pgs.
"Japanese Application Serial No. 2008-316282, Office Action dated May 16, 2011 ", 2 pgs.
"Japanese Application Serial No. 2008-316296, Office Action dated Feb. 28, 2011 ", 2 pgs.
"Japanese Application Serial No. 2008-316296, Office Action dated Jun. 22, 2010", 2 pgs.
"Japanese Application Serial No. 2008-323279, Office Action dated Sep. 30, 2010", 1 pg.
"Japanese Application Serial No. 2008-323290, Office Action dated Jun. 6, 2012", (W/ English Translation), 8 pgs.
"Japanese Application Serial No. 2008-323290, Office Action dated Jun. 8, 2011 ", (W/ English Translation), 8 pgs.
"Japanese Application Serial No. 2008-323290, Response filed Dec. 7, 2011 to Office Action dated Jun. 8, 2011", (W/ English Translation), 16 pgs.
"Japanese Application Serial No. 2008-536574, Office Action dated Mar. 11, 2010", (W/ English Translation), 4 pgs.
"Japanese Application Serial No. 2008-536574, Office Action dated Oct. 3, 2011", (W/ English Translation), 7 pgs.
"Japanese Application Serial No. 2008-536575, Office Action dated Jul. 7, 2011 ", (W/ English Translation), 5 pgs.
"Japanese Application Serial No. 2008-536576, Office Action dated Jul. 19, 2011 ", (W/ English Translation), 4 pgs.
Anonymous. (1995). "5mm Origin Tacker™ It Runs in Circles Around Staples," Guidant Oriain Advertising Literature, 2 pages.
Examiner's Interview Summary dated Feb. 11, 2005, for U.S. Appl. No. 10/271,334, filed Oct. 15, 2002, 1 page.
Final Office Action dated Dec. 22, 2010, for U.S. Appl. No. 11/978,752, filed Oct. 30, 2007, 6 pages.
Final Office Action dated Jan. 25, 2008, for U.S. Appl. No. 10/669,881, filed Sep. 24, 2003, 7 pages.
Final Office Action dated Jul. 21, 2009, for U.S. Appl. No. 11/540,427, filed Sep. 29, 2006, 8 pages.
Final Office Action dated Jun. 30, 2010, for U.S. Appl. No. 11/254,619, filed Oct. 20, 2005, 10 pages.
Final Office Action dated May 2, 2011, for U.S. Appl. No. 11/978,753, filed Oct. 30, 2007, 8 pages.
Final Office Action dated Apr. 13, 2011, for U.S. Appl. No. 11/488,305, filed Jul. 18, 2006, 8 pages.
Final Office Action dated Apr. 26, 2012, for U.S. Appl. No. 12/315,015, filed Nov. 26, 2008, 7 pages.
Final Office Action dated Aug. 4, 2011, for U.S. Appl. No. 11/540,428, filed Sep. 29, 2006, 9 pages.
Final Office Action dated Dec. 3, 2009, for U.S. Appl. No. 11/166,411, filed Jun. 24, 2005, 5 pages.
Final Office Action dated Oct. 20, 2011, for U.S. Appl. No. 11/254,619, filed Oct. 20, 2005, 11 pages.
Gadacz, T. et al. (Nov. 1995). "The Spiral Tacker: A New Technique for Stabilizing Prosthetic Mesh in Laparoscopic Hernia Repair," Surgical Rounds 461-467.
Hatchett, R.L. et al. (1995). "Extraperitoneal Endoscopic Burch Repair Using a Tacker Mesh Technique," Circa 1-4.
International Preliminary Examination Report dated Jul. 28, 2007, for PCT Patent Application No. PCT/US2006/033741, filed on Aug. 29, 2006, 5 pages.
International Preliminary Report on Patentability dated Jul. 10, 2006, for PCT Patent Application No. PCT/US2004/029402, filed on Sep. 10, 2004, 3 pages.
International Preliminary Report on Patentability dated Jul. 24, 2008, for PCT/US2006/037085, filed on Sep. 22, 2006, 9 pages.

International Preliminary Report on Patentability dated Jun. 18, 2008, for PCT Patent Application No. PCT/US06/033749, filed on Aug. 29, 2006, 6 pages.
International Preliminary Report on Patentability dated Jun. 18, 2008, for PCT Patent Application No. PCT/US2006/033748, filed on Aug. 29, 2006, 7 pages.
International Preliminary Report on Patentability dated Mar. 1, 2004, for PCT Patent Application No. PCT/US02/38365, filed on Nov. 29, 2002, 3 pages.
International Preliminary Report on Patentability dated Sep. 1, 2004, for PCT Patent Application No. PCT/US02/32753, filed on Oct. 15, 2002, 3 pages.
International Search Report dated Jul. 8, 2008, for PCT Patent Application No. PCT/US2006/033747, filed on Aug. 29, 2006, 2 pages.
International Search Report dated Aug. 15, 2007, for PCT Patent Application No. PCT/US06/033749, filed on Aug. 29, 2006, 3 pages.
International Search Report dated Aug. 15, 2007, for PCT Patent Application No. PCT/US2006/033748, filed on Aug. 29, 2006, 3 pages.
International Search Report dated Aug. 30, 2007, for PCT/US2006/037085, filed on Sep. 22, 2006, 9 pages.
International Search Report dated Aug. 30, 2007, for PCT/US2006/037085, filed on Sep. 22, 2006, one page.
International Search Report dated Dec. 11, 2009, for PCT/US2009/005604, filed on Oct. 14, 2009, 3 pages.
International Search Report dated Dec. 18, 2009, for PCT/US2009/005609, filed Oct. 14, 2009, 3 pages.
International Search Report dated Feb. 24, 2006, for PCT Patent Application No. PCT/US2004/029402, filed on Sep. 10, 2004, 3 pages.
International Search Report dated Mar. 30, 2007, for PCT Patent Application No. PCT/US2006/033741, filed on Aug. 29, 2006, 2 pages.
International Search Report dated Mar. 6, 2003, for PCT Patent Application No. PCT/US02/32753, filed on Oct. 15, 2002, one page.
International Search Report dated May 8, 2003, for PCT Patent Application No. PCT/US02/38365, filed on Nov. 29, 2002, 4 pages.
Medical Technologies. (Oct. 1995). "Laparoscopic Surgery," Medical Data International, Inc. MedPro p. 190.
Newman, L. et al. (1995). "Tacker-Assisted TAPP Procedure," Circa, 2 pages.
Non Final Office Action dated Jun. 22, 2012, for U.S. Appl. No. 12/288,034, filed Oct. 16, 2008, 7 pgs.
Non Final Office Action dated May 18, 2004, for U.S. Appl. No. 10/271,334, filed Oct. 15, 2002, 8 pages.
Non Final Office Action dated May 5, 2009, for U.S. Appl. No. 11/166,411, filed Jun. 24, 2005, 7 pages.
Non-Final Office Action dated Feb. 3, 2011, for U.S. Appl. No. 11/254,619, filed Oct. 20, 2005, 8 pges.
Non-Final Office Action dated Jan. 27, 2006, for U.S. Appl. No. 10/669,881, filed Sep. 24, 2003, 5 pages.
Non-Final Office Action dated May 14, 2008, for U.S. Appl. No. 11/255,116, filed Oct. 20, 2005, 14 pages.
Non-Final Office Action dated May 20, 2010, for U.S. Appl. No. 11/978,752, filed Oct. 30, 2007, 5 pages.
Non-Final Office Action dated Oct. 1, 2009, for U.S. Appl. No. 11/254,619, filed Oct. 20, 2005, 5 pges.
Non-Final Office Action dated Oct. 6, 2008, for U.S. Appl. No. 11/540,427, filed Sep. 29, 2006, 9 pages.
Non-Final Office Action dated Nov. 12, 2010, for U.S. Appl. No. 11/540,428, filed Sep. 29, 2006, 7 pages.
Non-Final Office Action dated Oct. 31, 2011, for U.S. Appl. No. 11/488,305, filed on Jul. 18, 2006, 6 pages.
Non-Final Office Action dated Oct. 6, 2011, for U.S. Appl. No. 12/315,015, filed Nov. 26, 2008, 10 pages.
Non-Final Office Action dated Sep. 1, 2010, for U.S. Appl. No. No. 11/488,305, filed Jul. 18, 2006, 7 pages.
Non-Final Office Action dated Sep. 3, 2010, for U.S. Appl. No. 11/978,753, filed Oct. 30, 2007, 7 pages.
Notice of Allowability dated Feb. 11, 2005, for U.S. Appl. No. 10/271,334, filed Oct. 15, 2002, 4 pages.

(56) References Cited

OTHER PUBLICATIONS

Notice of Allowance dated Apr. 29, 2011, for U.S. Appl. No. 11/540,427, filed Sep. 29, 2006, 8 pages.
Notice of Allowance dated Aug. 10, 2009, for U.S. Appl. No. 11/255,116, filed Oct. 20, 2005, 4 pages.
Notice of Allowance dated Aug. 31, 2011, for U.S. Appl. No. 11/978,752, filed Oct. 30, 2007, 5 pages.
Notice of Allowance dated Oct. 8, 2008, for U.S. Appl. No. 10/669,881, filed Sep. 24, 2003, 6 pages.
Notice of Allowance dated Aug. 23, 2011, for U.S. Appl. No. 11/166,411, filed Jun. 24, 2005, 5 pages.
Notice of Allowance dated Aug. 26, 2005, for U.S. Appl. No. 10/271,334, filed Oct. 15, 2002, 3 pages.
Notice of Allowance dated Jan. 6, 2011, for U.S. Appl. No. 11/166,411, filed Jun. 24, 2005, 4 pages.
Notice of Allowance dated Mar. 17, 2005, for U.S. Appl. No. 10/271,334, filed Oct. 15, 2002, 3 pages.
Response to Non-final Office Action dated Nov. 22, 2004, for U.S. Appl. No. 10/271,334, filed Oct. 15, 2002, 10 pages.
U.S. Appl. No. 13/162,384, filed Jun. 16, 2011 by Bolduc (Copy not attached).
Written Opinion dated Jul. 8, 2008, for PCT Patent Application No. PCT/US2006/033747, filed on Aug. 29, 2006, 3 pages.
Written Opinion dated Aug. 15, 2007, for PCT Patent Application No. PCT/US06/033749, filed on Aug. 29, 2006, 5 pages.
Written Opinion dated Aug. 15, 2007, for PCT Patent Application No. PCT/US2006/033748, filed on Aug. 29, 2006, 5 pages.
Written Opinion dated Aug. 26, 2003, for PCT Patent Application No. PCT/US02/32753, filed on Oct. 15, 2002, 4 pages.
Written Opinion dated Aug. 30, 2007, for PCT/US2006/037085, filed on Sep. 22, 2006, 7 pages.
Written Opinion dated Dec. 11, 2009, for PCT/US2009/005604, filed on Oct. 14, 2009, 7 pages.
Written Opinion dated Dec. 18, 2009, for PCT/US2009/005609, filed Oct. 14, 2009, 6 pages.
Written Opinion dated Feb. 24, 2006, for PCT Patent Application No. PCT/US2004/029402, filed on Sep. 10, 2004, 3 pages.
Written Opinion dated Mar. 30, 2007, for PCT Patent Application No. PCT/US2006/033741, filed on Aug. 29, 2006, 4 pages.
Written Opinion dated Oct. 27, 2003, for PCT Patent Application No. PCT/US02/38365, filed on Nov. 29, 2002, 4 pages.
U.S. Appl. No. 10/271,334, U.S. Pat. No. 6,960,217, filed Oct. 15, 2002, Title: Endovascular Aneurysm Repair System.
U.S. Appl. No. 11/166,411, U.S. Pat. No. 8,092,519, filed Jun. 24, 2005, Title: Endovascular Aneurysm Repair System.
U.S. Appl. No. 11/540,427, U.S. Pat. No. 7,959,663, filed Sep. 29, 2006, Title: Endovascular Aneurysm Repair System.
U.S. Appl. No. 13/162,384, filed Jun. 16, 2011, Title: Endovascular Aneurysm Repair System.
U.S. Appl. No. 11/978,752, U.S. Pat. No. 8,083,752, filed Oct. 30, 2007, Title: Endovascular Aneurysm Repair Systems and Methods.
U.S. Appl. No. 11/978,753, filed Oct. 30, 2007, Title: Systems and Methods for Applying Tissue-Piercing Fasteners.
U.S. Appl. No. 10/307,226, U.S. Pat. No. 8,075,570, filed Nov. 29, 2002, Title: Intraluminal Prosthesis Attachment Systems and Methods.
U.S. Appl. No. 11/166,428, filed Jun. 24, 2005, Title: Multi-Lumen Prosthesis Systems and Methods.
U.S. Appl. No. 10/693,255, U.S. Pat. No. 6,929,661, filed Oct. 24, 2003, Title: Multi-Lumen Prosthesis Systems and Methods.
U.S. Appl. No. 10/786,465, U.S. Pat. No. 8,231,639, filed Feb. 25, 2004, Title: Systems and Methods for Attaching a Prosthesis Within a Body . . . .
U.S. Appl. No. 13/495,836, filed Jun. 13, 2012, Title: Systems and Methods for Attaching a Prosthesis Within a Body Lumen or Hollow Organ.
U.S. Appl. No. 10/669,881, U.S. Pat. No. 7,491,232, filed Sep. 24, 2003, Title: Catheter-Based Fastener Implantation Apparatus and Methods . . . .
U.S. Appl. No. 12/315,015, filed Nov. 26, 2008, Title: Catheter-Based Fastener Implantation Apparatus and Methods.
U.S. Appl. No. 11/540,428, filed Sep. 29, 2006, Title: Catheter-Based Fastener Implantation Apparatus and Methods.
U.S. Appl. No. 10/692,283, U.S. Pat. No. 7,147,657, filed Oct. 23, 2003, Title: Prosthesis Delivery Systems and Methods.
U.S. Appl. No. 11/633,724, U.S. Pat. No. 8,080,050, filed Dec. 5, 2006, Title: Prosthesis Delivery Systems and Methods.
U.S. Appl. No. 13/291,942, filed Nov. 8, 2011, Title: Prosthesis Delivery Systems and Methods.
U.S. Appl. No. 11/254,619, filed Oct. 20, 2005, Title: Devices, System, and Methods for Guiding an Operative Tool Into an Interior Body . . . .
U.S. Appl. No. 11/254,444, U.S. Pat. No. 7,828,838, filed Oct. 20, 2005, Title: Devices, Systems and Methods for Prosthesis Delivery and . . . .
U.S. Appl. No. 12/942,232, filed Nov. 9, 2010, Title: Devices, Systems, and Methods for Prosthesis Delivery and Implantation, Including a . . . .
U.S. Appl. No. 10/808,216, filing Mar. 24, 2004, Title: Devices, Systems and Methods for Supporting Tissue and/or Structures Within a Hollow.
U.S. Appl. No. 11/365,056, filed Mar. 1, 2006, Title: Devices, Systems and Methods for Supporting Tissue and/or Structures Within a Hollow . . . .
U.S. Appl. No. 13/157,242, filing Jun. 9, 2011, Title: Devices, Systems, and Methods for Supporting Tissue and/or Structures Within a Hollow . . . .
U.S. Appl. No. 10/692,282, U.S. Pat. No. 7,128,754, filed Oct. 23, 2003, Title: Catheter-Based Fastener Implantation Apparatus and Methods.
U.S. Appl. No. 11/580,584, U.S. Pat. No. 7,959,670, filed Oct. 13, 2006, Title: Catheter-Based Fastener Implantation Methods.
U.S. Appl. No. 11/254,950, U.S. Pat. No. 7,823,267, filed Oct. 20, 2005, Title: Devices, Systems, and Methods for Prosthesis Delivery and . . . .
U.S. Appl. No. 12/917,842, filed Nov. 2, 2010, Title: Devices, Systems, and Methods for Prosthesis Delivery and Implantation, Including . . . .
U.S. Appl. No. 11/255,116, U.S. Pat. No. 7,637,932, filed Oct. 20, 2005, Title: Devices, Systems, and Methods for Prosthesis Delivery and . . . .
U.S. Appl. No. 12/653,219, filed Dec. 10, 2009, Title: Devices, Systems and Methods for Prosthesis Delivery and Implantation.
U.S. Appl. No. 11/488,305, filed Jul. 18, 2006, Title: Endovascular Aneurysm Devices, Systems, and Methods.
U.S. Appl. No. 12/288,034, filed Oct. 16, 2008, Title: Devices, Systems and Methods for Endovascular Staple and/or Prosthesis Delivery and . . . .
U.S. Appl. No. 10/752,435, filed Jan. 6, 2004, Title: Prosthes Systems and Methods Sized and Configured for the Receipt and Retention of . . . .
U.S. Appl. No. 11/981,112, filed Oct. 31, 2007, Title: Prosthesis Systems and Methods.
U.S. Appl. No. 12/288,045, filed Oct. 16, 2008, Title: Devices, Systems, and Methods for Endovascular Staple and/or Prosthesis Delivery . . . .
U.S. Appl. No. 12/288,032, filed Oct. 16, 2008, Title: Devices, Systems, and Methods for Endovascular Staple and/or Prosthesis Delivery . . . .
U.S. Appl. No. 14/230,469, filed Mar. 31, 2014, Title: Devices, Systems, and Methods for Prosthesis Delivery and Implantation, Including the . . . .
U.S. Appl. No. 14/210,683, filed Mar. 14, 2014, Title: Systems and Methods for Attaching a Prosthesis Within a Body Lumen or Hollow Organ.
U.S. Appl. No. 14/595,928, filed Jan. 13, 2015, Title: Endovascular Aneurysm Devices, Systems, and Methods.

\* cited by examiner

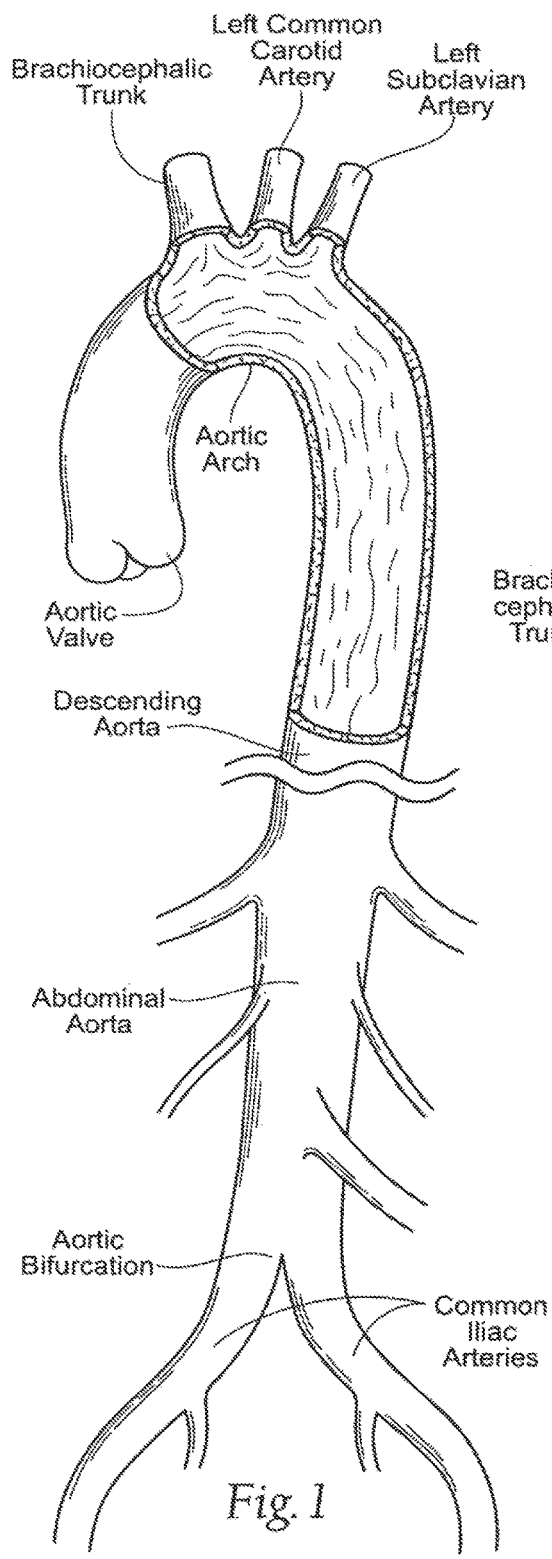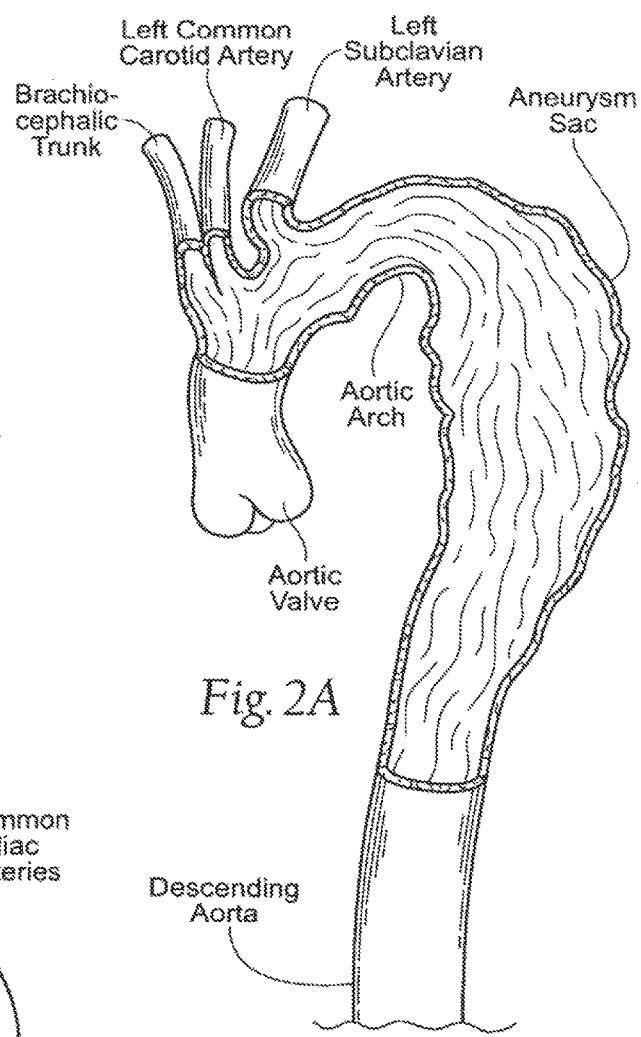
Fig. 1
Fig. 2A

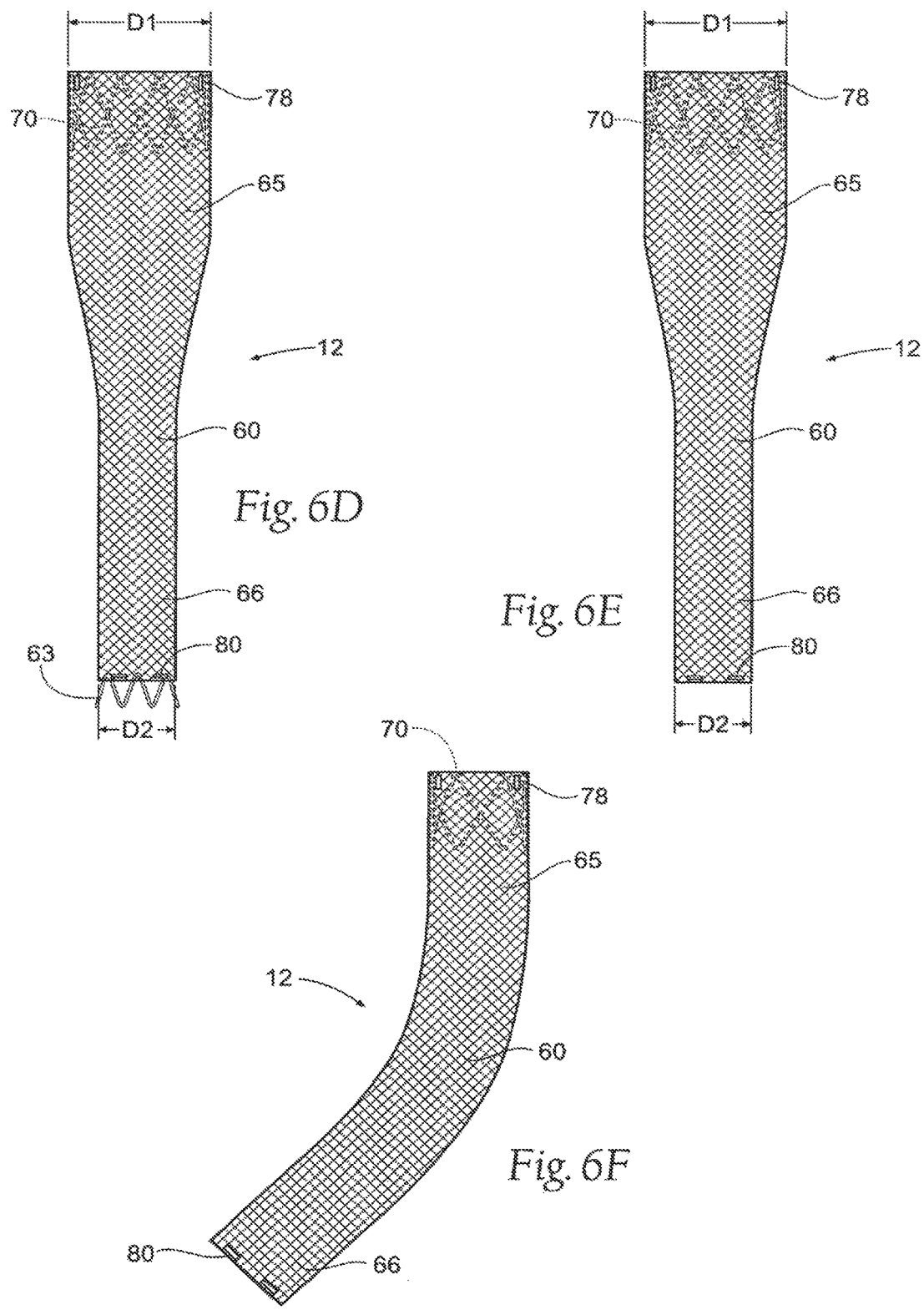

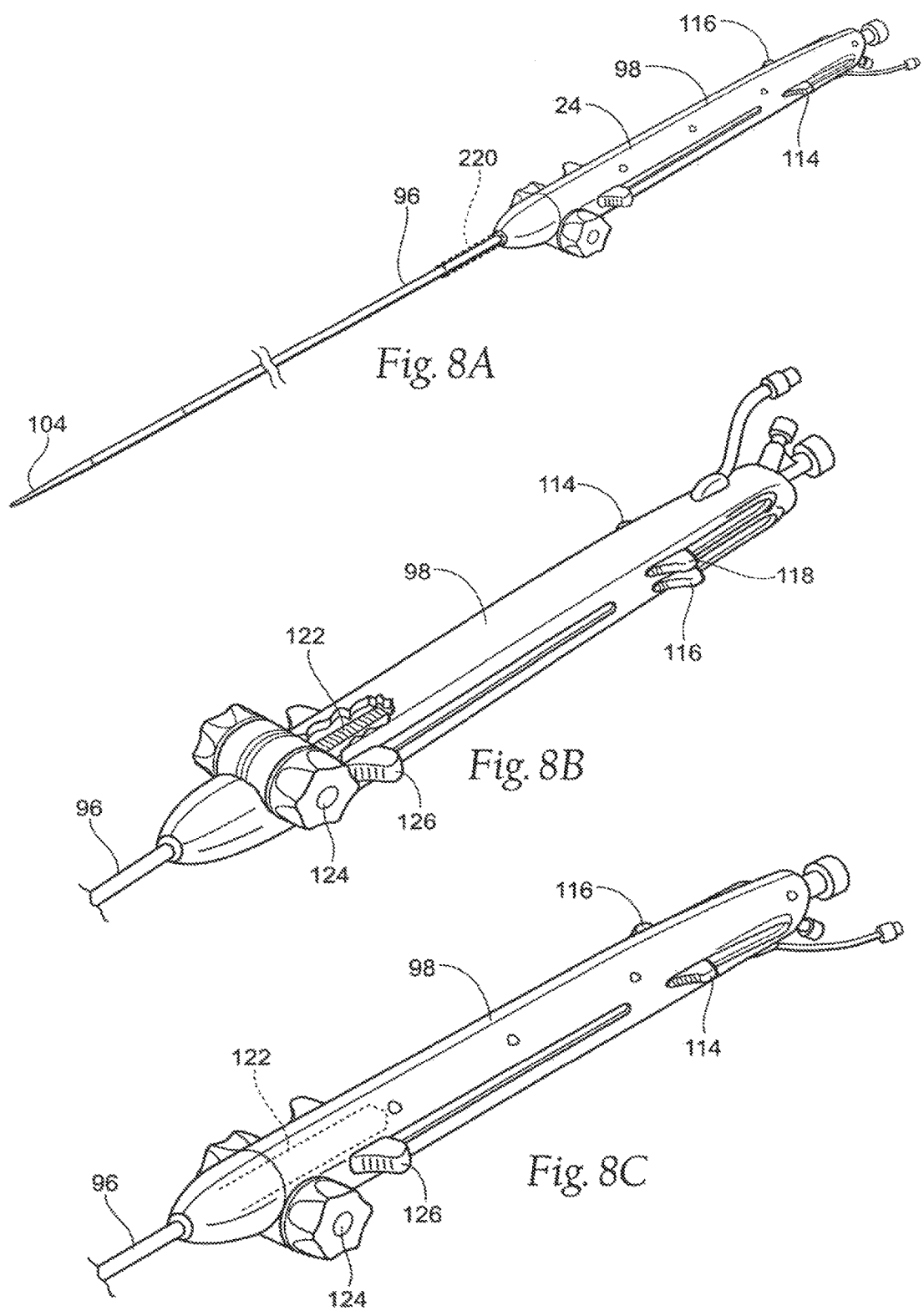

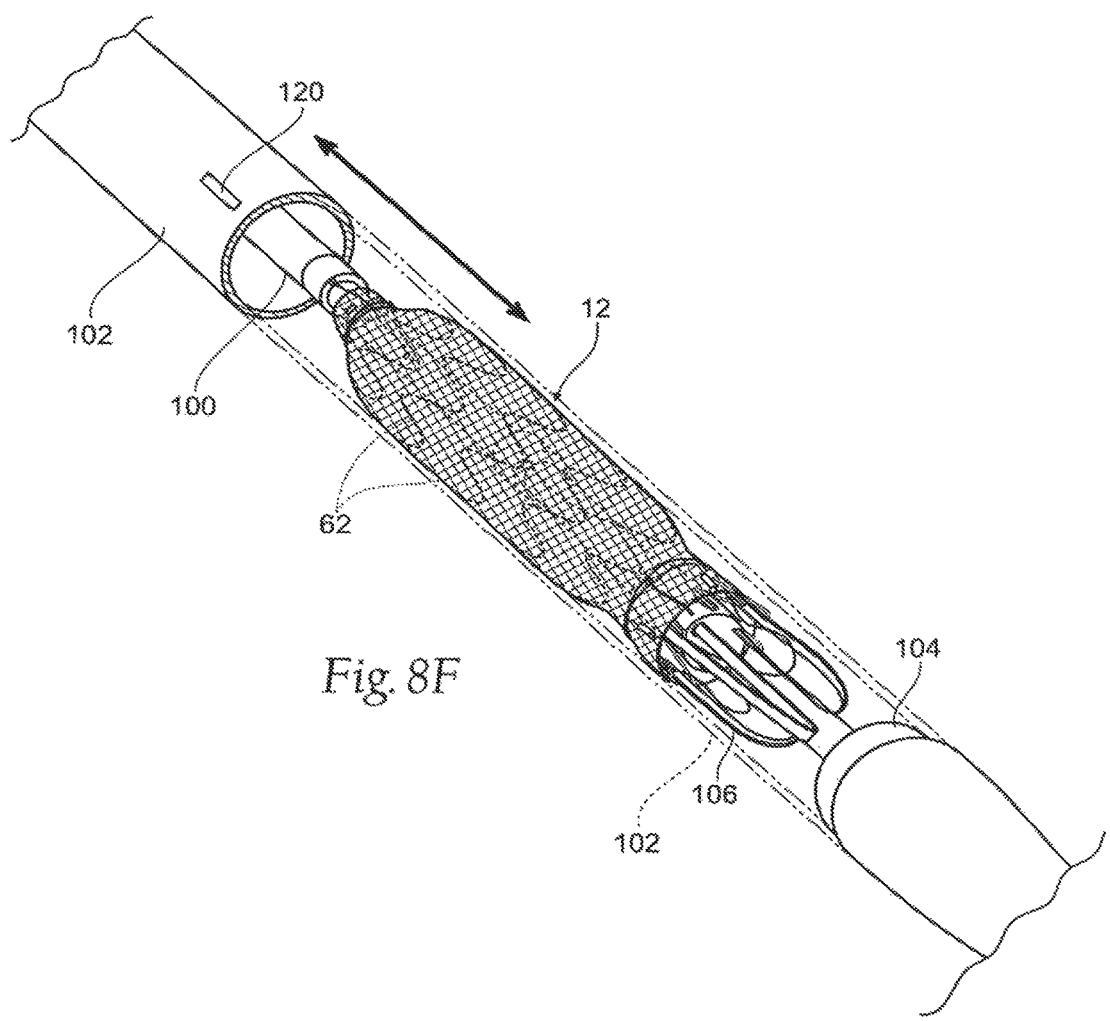

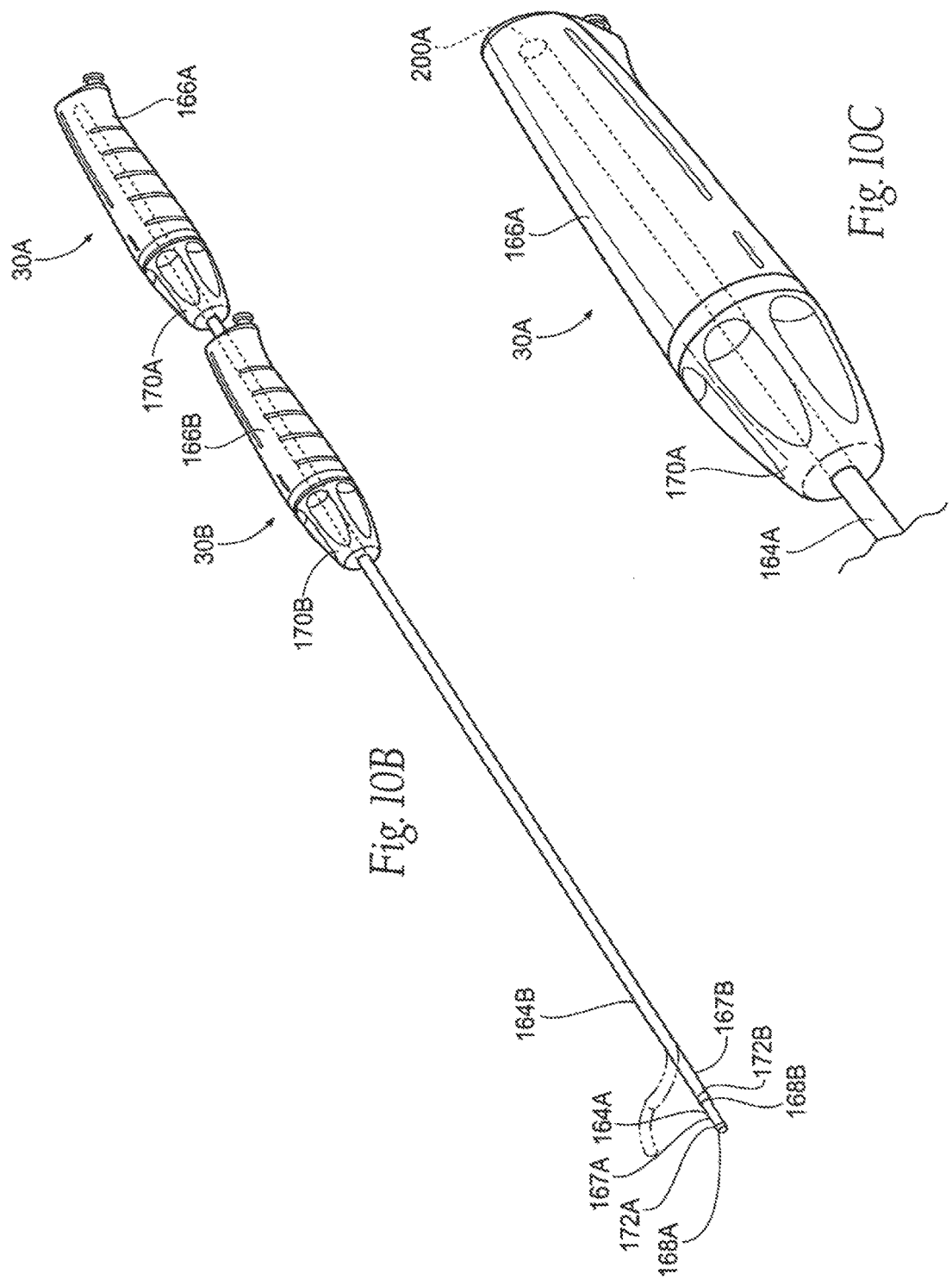

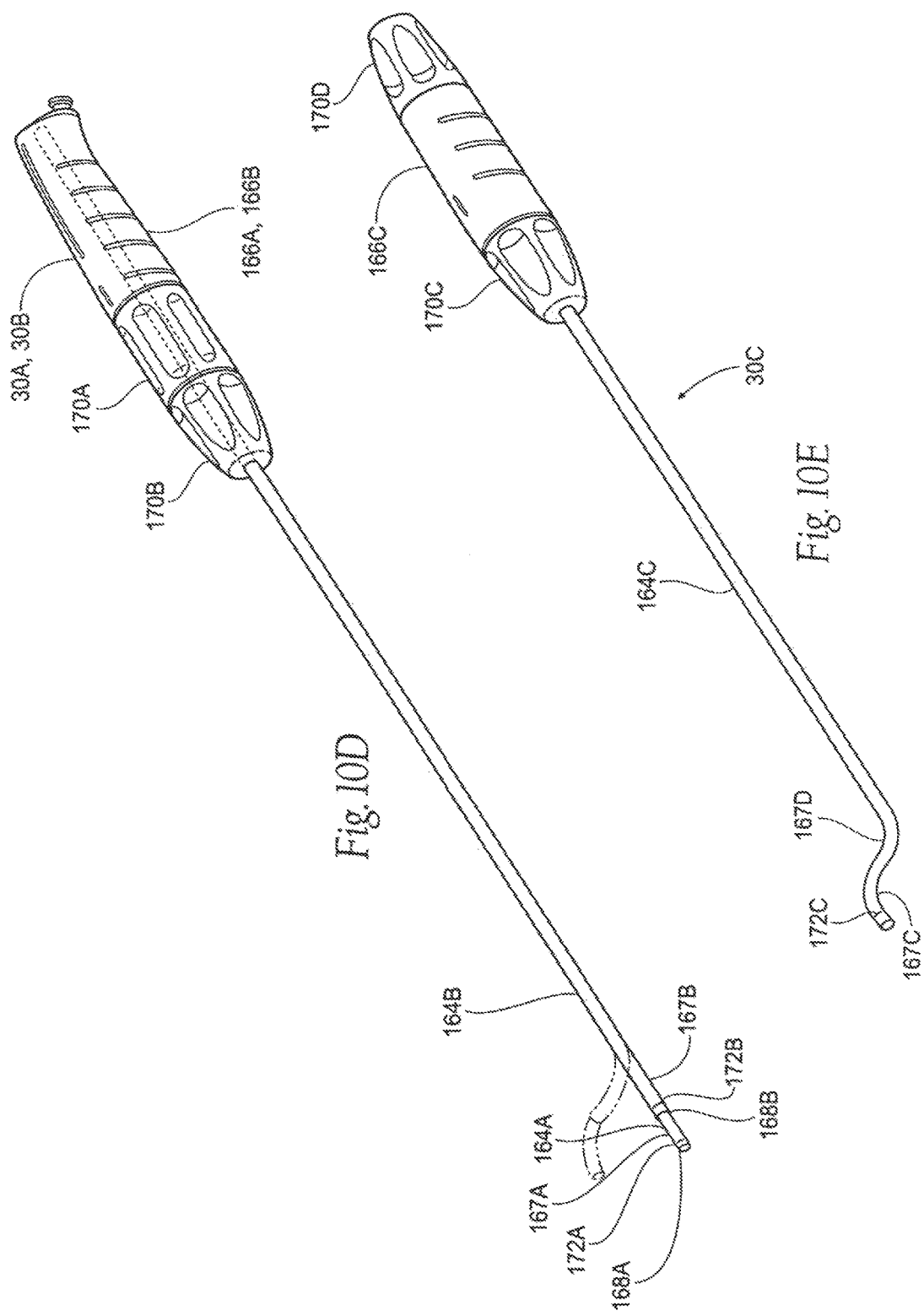

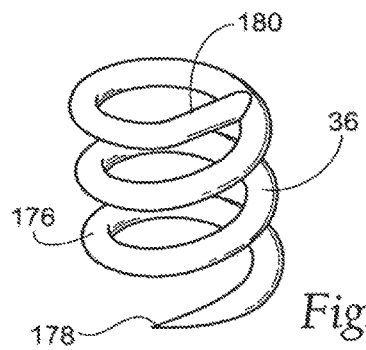
Fig. 11A
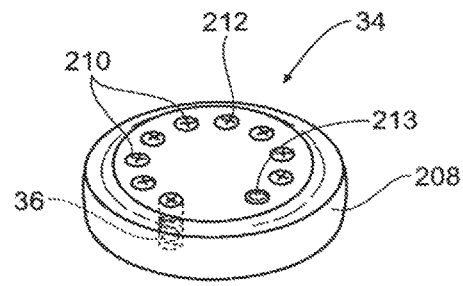
Fig. 11B
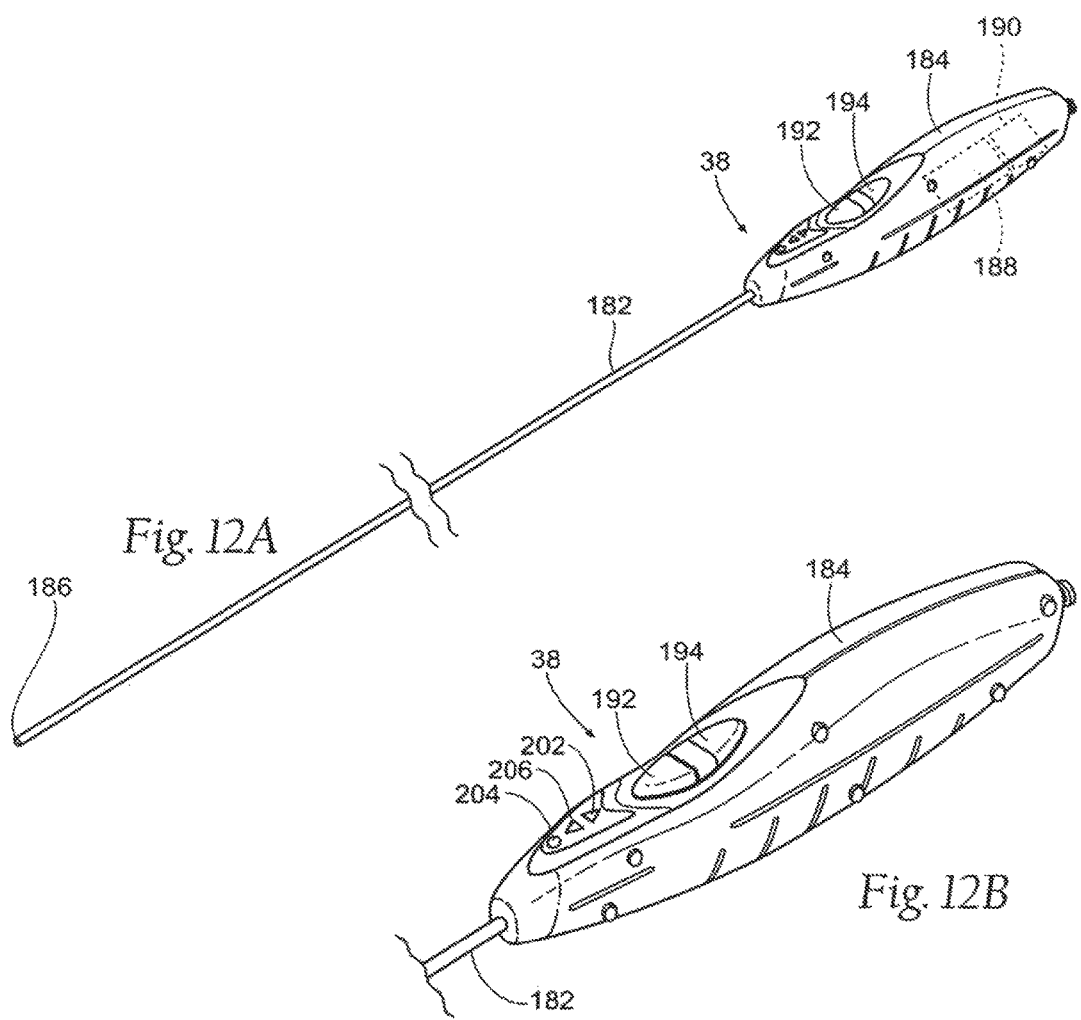
Fig. 12A
Fig. 12B

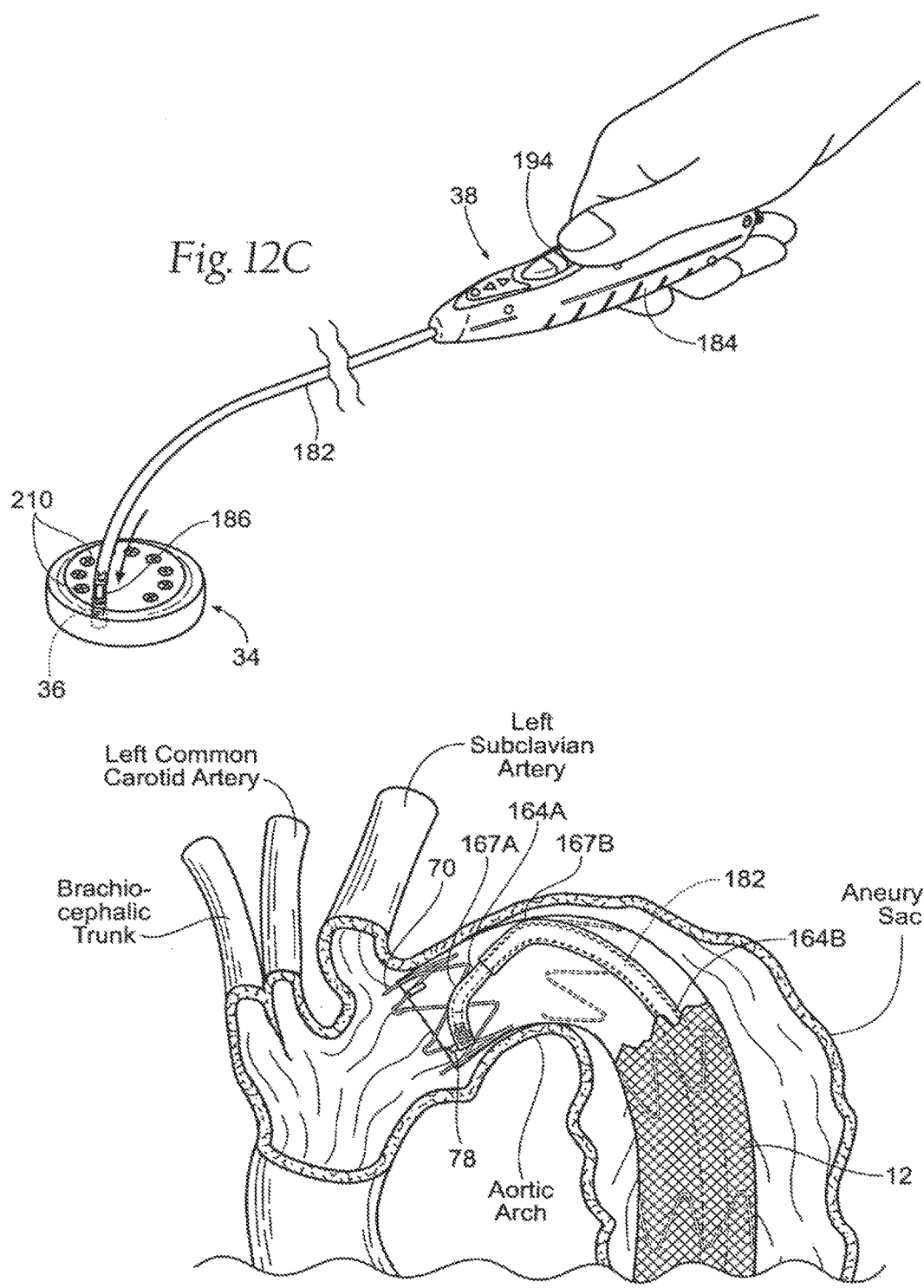

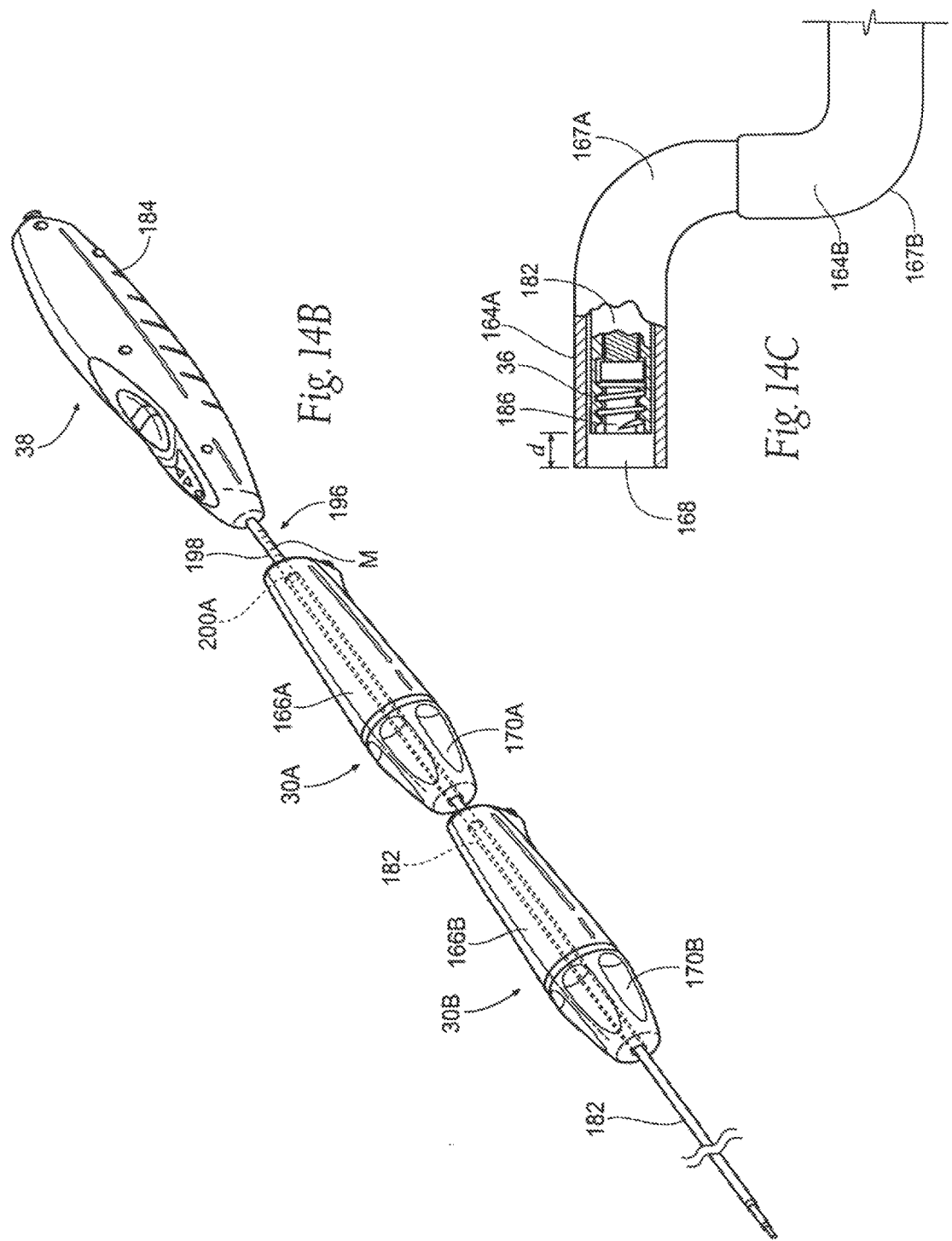

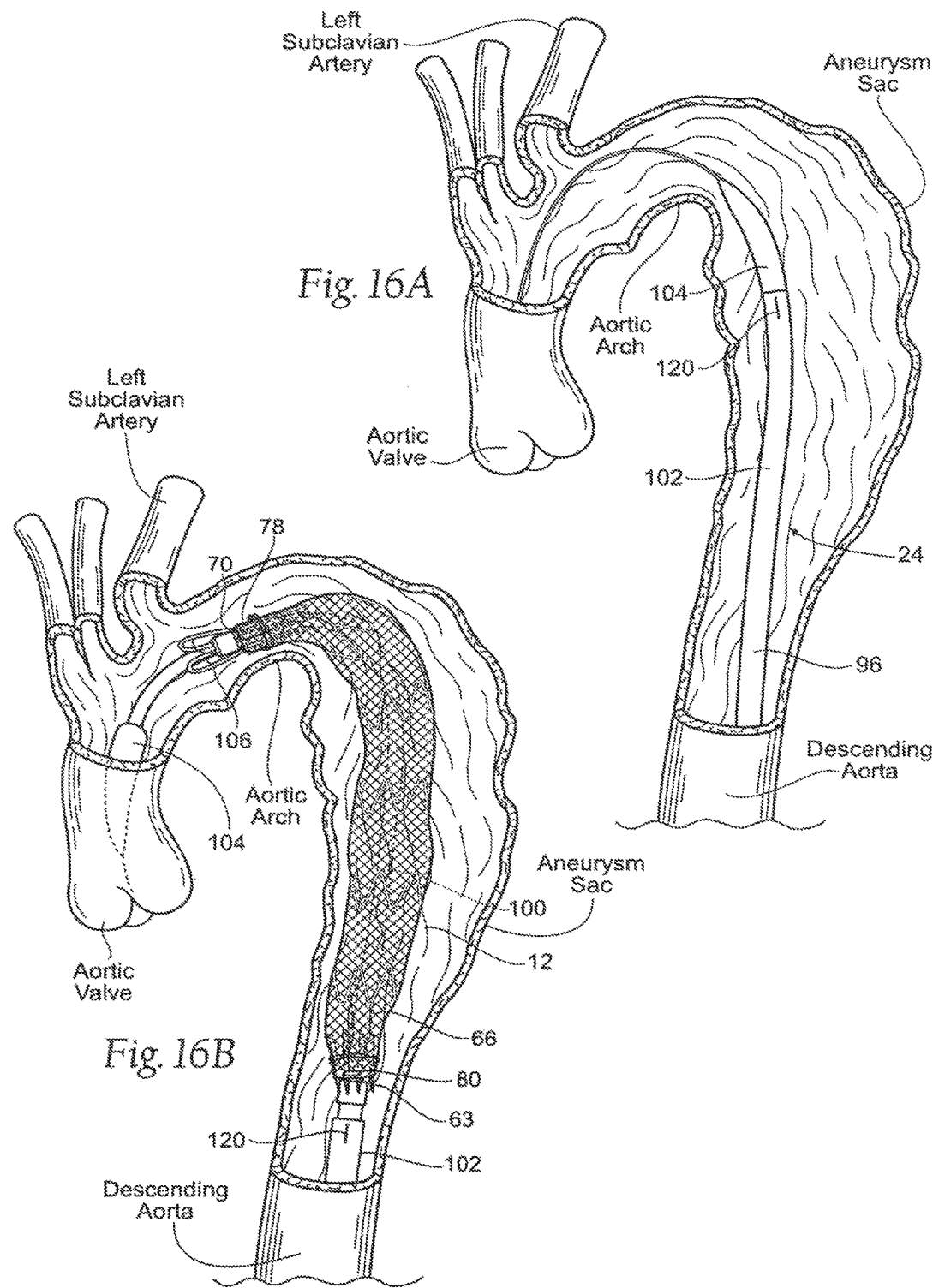

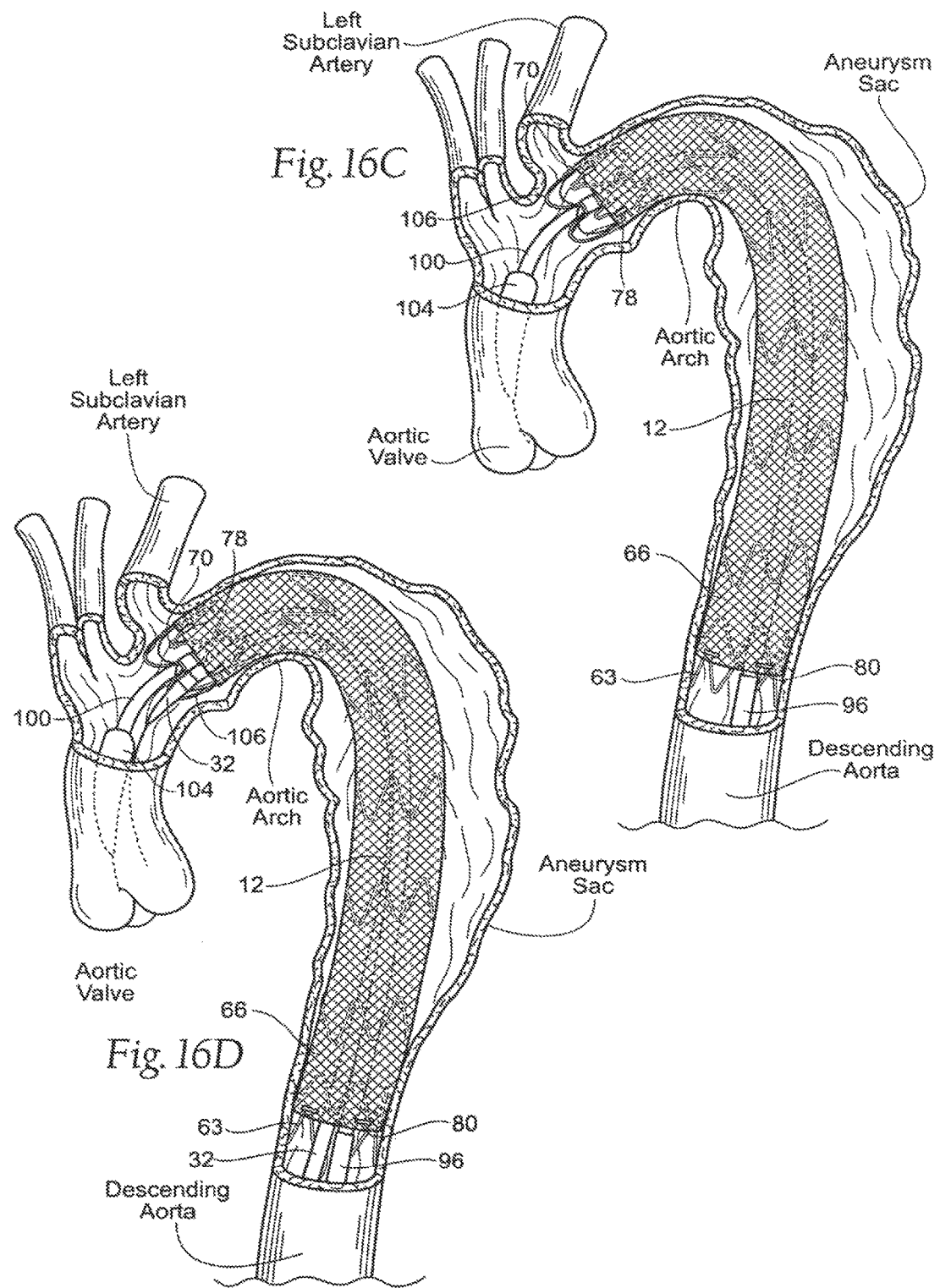

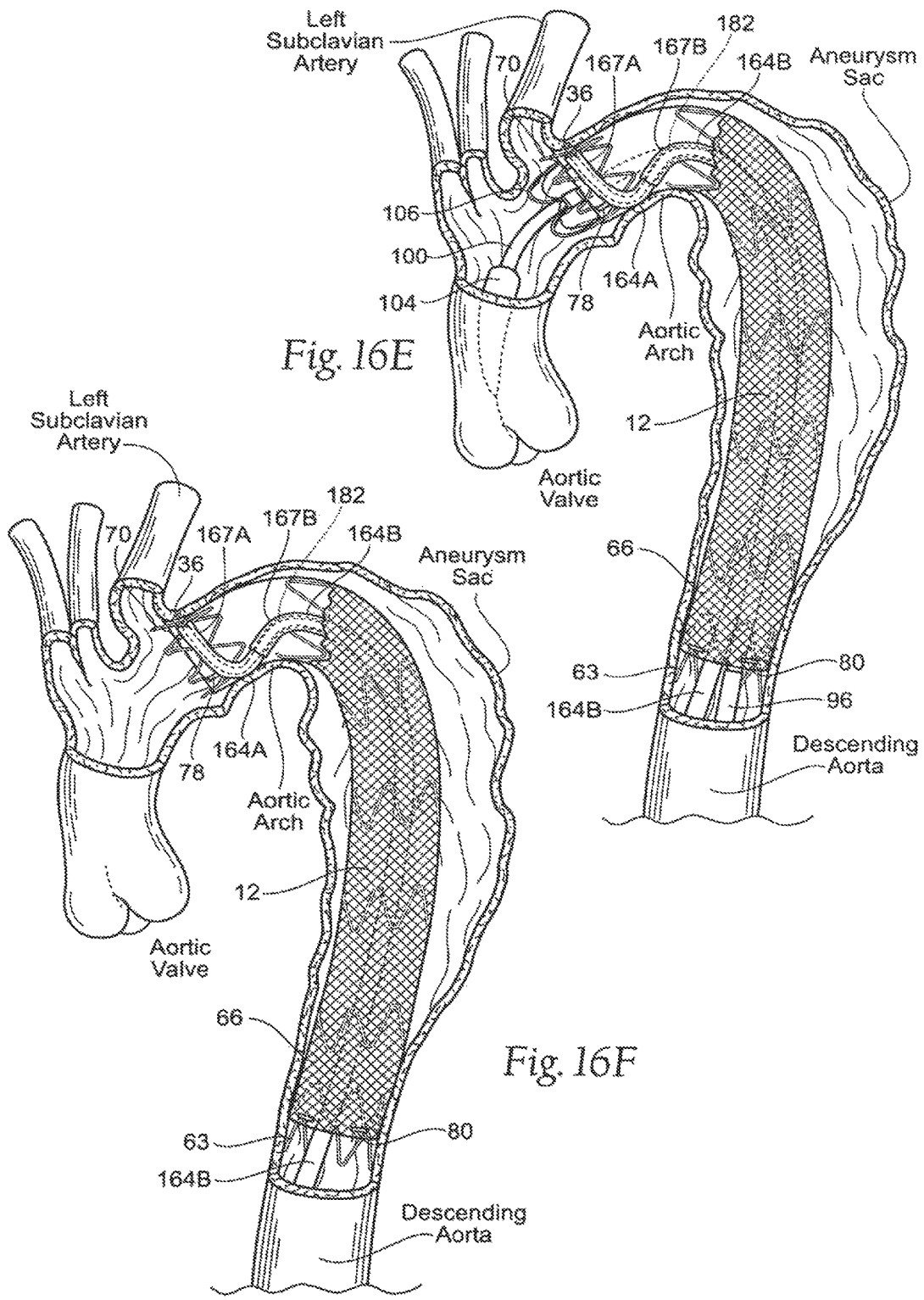

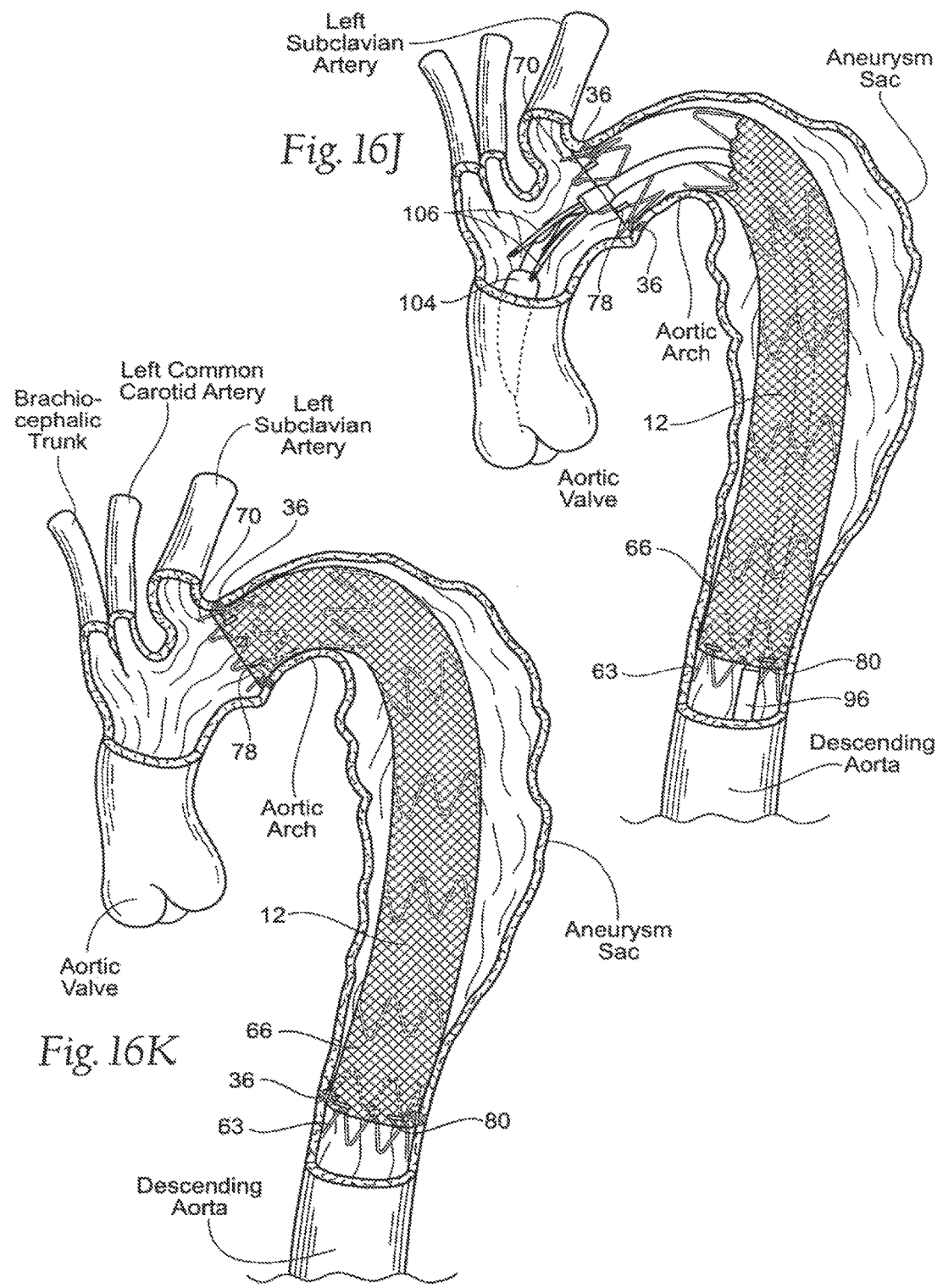

DEVICES, SYSTEMS, AND METHODS FOR ENDOVASCULAR STAPLE AND/OR PROSTHESIS DELIVERY AND IMPLANTATION

RELATED APPLICATIONS

This application is a Division of co-pending U.S. patent application Ser. No. 12/288,031, filed Oct. 16, 2008.

U.S. patent application Ser. No. 12/288,031 is a continuation-in-part of U.S. patent application Ser. No. 11/488,305, filed Jul. 18, 2006, now abandoned.

U.S. patent application Ser. No. 12/288,031 is also a continuation-in-part of U.S. patent application Ser. No. 11/255,116, filed Oct. 20, 2005, now U.S. Pat. No. 7,637,932.

U.S. patent application Ser. No. 12/288,031 is also a continuation-in-part of U.S. patent application Ser. No. 11/254,619, filed Oct. 20, 2005, now U.S. Pat. No. 9,320,503.

U.S. patent application Ser. No. 12/288,031 is also a continuation-in-part of U.S. patent application Ser. No. 11/633,724, filed Dec. 5, 2006, now U.S. Pat. No. 8,080,050 which is a division of U.S. patent application Ser. No. 10/692,283, filed Oct. 23, 2003, now U.S. Pat. No. 7,147,657. which claims the benefit of U.S. Provisional Patent Application Ser. No. 60/488,753, filed Jul. 21, 2003.

U.S. patent application Ser. No. 12/288,031 also is a continuation-in-part of U.S. patent application Ser. No. 10/786,465, filed Feb. 25, 2004, now U.S. Pat. No. 8,231,639.

U.S. patent application Ser. No. 12/288,031 is also a continuation-in-part of U.S. patent application Ser. No. 11/166,428, filed Jun. 24, 2005, now abandoned, which is a division of U.S. patent application Ser. No. 10/693,255, filed Oct. 24, 2003, now U.S. Pat. No. 6,929,661, which claims the benefit of U.S. Provisional Patent Application Ser. No. 60/489,011, filed Jul. 21, 2003.

U.S. patent application Ser. No. 12/288,031 also is a continuation-in-part of U.S. patent application Ser. No. 10/307,226, filed Nov. 29, 2002, now U.S. Pat. No. 8,075,570.

U.S. patent application Ser. No. 12/288,031 is also a continuation-in-part of U.S. patent application Ser. No. 10/669,881, filed Sep. 24, 2003, now U.S. Pat. No. 7,491,232.

U.S. patent application Ser. No. 12/288,031 is also a continuation-in-part of U.S. patent application Ser. No. 11/166,411, filed Jun. 24, 2005, now U.S. Pat. No. 8,092,519, which is a division of U.S. patent application Ser. No. 10/271,334, filed Oct. 15, 2002, now U.S. Pat. No. 6,960,217, which claims the benefit of U.S. Provisional Patent Application Ser. No. 60/333,937, filed Nov. 28, 2001. Each of the preceding applications is incorporated herein by reference.

FIELD OF THE INVENTION

The invention relates generally to devices, systems, and methods for the delivery and implantation of an endovascular staple(s) and/or prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta occur in the abdominal region, usually in the infrarenal area between the renal arteries and the aortic bifurcation. Aneurysms can also occur in the tortuous thoracic region between the aortic arch and renal arteries. The rupture of an aortic aneurysm results in massive hemorrhaging and has a high rate of mortality.

Damage or disease of a vessel such as the aorta may also result in a dissection of the vessel wall. Aortic dissections are usually caused by a connective tissue disorder and/or high blood pressure. Left untreated, an aortic dissection can rupture or critically reduce blood flow to the heart, the brain, the spinal cord, the abdominal organs and the legs.

Open surgical replacement of a diseased or damaged section of vessel can eliminate the risk of vessel rupture. In this procedure, the diseased or damaged section of vessel is surgically removed and a prosthesis, made generally in either in a straight or bifurcated configuration, is installed and then permanently attached and sealed to the ends of the native vessel by suture. The prostheses for these procedures are usually unsupported woven tubes and are typically made from polyester, ePTFE or other suitable materials. The prostheses are longitudinally unsupported so they can accommodate changes in the morphology of an aneurysm, dissection, and/or the native vessel. However, these procedures require a large surgical incision and have a high rate of morbidity and mortality. In addition, many patients are unsuitable for this type of major surgery due to other co-morbidities.

Endovascular aneurysm and dissection repair has been introduced to overcome the problems associated with open surgical repair. The diseased or damaged section of the vessel is bridged with a vascular prosthesis, i.e., graft, which is placed intraluminally. Typically these prostheses for aortic aneurysms and dissections are delivered collapsed on a catheter through the femoral artery. These prostheses are usually designed with a fabric material attached to a metallic scaffolding (stent) structure, which expands or is expanded to contact the internal diameter of the vessel.

Unlike open surgical repair of diseased or damaged sections of a vessel, such as an aortic aneurysm or an aortic dissection, intraluminally deployed prostheses are not sutured to the native vessel, but rely on either barbs or hooks extending from the stent, which penetrate into the native vessel during deployment and require a substantial area of healthy tissue to penetrate, and/or the radial expansion force of the stent itself is utilized to hold the prosthesis in position. These prosthesis attachment means do not provide the same level of attachment when compared to suture and can damage the native vessel upon deployment. In addition, in some areas the native vessel may include bends or turns, making it difficult for one or both ends of the deployed prosthesis to expand, appose and seal the prosthesis to the vessel wall.

Accordingly, there is a need for improved prosthesis delivery and fastening devices, systems, and methods that deliver and fasten a staple(s) and/or a prosthetic graft within or to a body lumen, the prosthesis being able to adapt to changes in the vessel morphology and able to be deployed and fastened safely and without damage to the native vessel, including a tortuous vessel.

SUMMARY OF THE INVENTION

The devices, systems, and methods for delivering and implanting radially expandable prostheses in the body lumens are described. In particular, the present invention provides improved devices, systems, and methods for implanting vascular prostheses into blood vessels, including both arterial and venous systems. In the exemplary embodiments, a variety of tools are used to place prostheses in vasculature to repair and/or reinforce aneurysms and/or dissections, particularly thoracic aortic aneurysms, and aortic dissections.

One aspect of the invention provides devices, systems, and methods including a steerable guide catheter comprising a first guide tube having a length and defining an open interior lumen, the first guide tube lumen adapted for accommodating passage of an operative endovascular tool, a second guide tube having a length and defining an open interior lumen, the second guide tube lumen adapted for accommodating the first guide tube, and a handle assembly. The handle assembly may comprise a first deflecting means coupled to a distal end region of the first guide tube to apply a deflecting force to bend the distal end region of the first guide tube, the first deflecting means adapted to bend the distal end region in a first articulated position, and a second deflecting means coupled to a distal end region of the second guide tube to apply a deflecting force to bend the distal end region of the second guide tube, the second deflecting means adapted to bend the distal end region in a second articulated position. The second articulated position may be different than the first articulated position. The second guide tube may comprise a length that is shorter than the length of the first guide tube. The steerable guide catheter farther include an operative tool that applies one or more fasteners to tissue.

Another aspect of the invention provides devices, systems, and methods including a steerable guide catheter comprising a steerable guide catheter comprising a first guide tube having a length and defining an open interior lumen, the first guide tube lumen adapted for accommodating passage of an operative endovascular tool, a second guide tube having a length and defining an open interior lumen, the second guide tube lumen adapted for accommodating passage of the first guide tube, a first handle assembly comprising a first deflecting means coupled to a distal end region of the first guide tube to apply a deflecting force to bend the distal end region of the first guide tube, the first deflecting means adapted to bend the distal end region in a first articulated position, and a second handle assembly comprising a second deflecting means coupled to a distal end region of the second guide tube to apply a deflecting force to bend the distal end region of the second guide tube, the second deflecting means adapted to bend the distal end region in a second articulated position.

The second articulated position may be different than the first articulated position. The second guide tube may comprise a length that is shorter than the length of the first guide tube.

Yet another aspect of the invention provides devices, systems, and methods including a method comprising providing a steerable guide catheter, the guide catheter comprising a first guide tube having a length and defining an open interior lumen, the first guide tube lumen adapted for accommodating passage of an operative endovascular tool, a second guide tube having a length and defining an open interior lumen, the second guide tube lumen adapted for accommodating the first guide tube, and a handle assembly. The handle assembly may comprise a first deflecting means coupled to a distal end region of the first guide tube to apply a deflecting force to bend the distal end region of the first guide tube, and a second deflecting means coupled to a distal end region of the second guide tube to apply a deflecting force to bend the distal end region of the second guide tube, the second deflecting means adapted to bend the distal end region in a second articulated position.

Additional steps may include passing the operative tool through the guide catheter, and operating the operative tool while residing in the guide catheter to apply at least one fastener to tissue.

The devices, systems, and methods may further including manipulating the first deflecting means for applying a deflecting force and bending the distal end region of the first guide tube in a first articulated position, and manipulating the second deflecting means for applying a deflecting force and bending the distal end region of the second guide tube in a second articulated position. The second articulated position may be different than the first articulated position.

Yet another aspect of the invention provides devices, systems, and methods including a method comprising providing a first guide tube having a length and defining an open interior lumen, the first guide tube lumen adapted for accommodating passage of an operative endovascular tool, the first guide tube including a first handle assembly comprising a first deflecting means coupled to a distal end region of the first guide tube to apply a deflecting force to bend the distal end region of the first guide tube, providing a second guide tube having a length and defining an open interior lumen, the second guide tube lumen adapted for accommodating passage of the first guide tube, the second guide tube including a second handle assembly comprising a second deflecting means coupled to a distal end region of the second guide tube to apply a deflecting force to bend the distal end region of the second guide tube, inserting the first guide tube into the lumen of the second guide tube, advancing the first guide tube until the distal end region of the first guide tube extends beyond the distal end region of the second guide tube, passing the operative tool through the guide catheter, and operating the operative tool while residing in the guide catheter to apply at least one fastener to tissue.

Additional steps may include manipulating the first deflecting means for applying a deflecting force and bending the distal end region of the first guide tube in a first articulated position, and manipulating the second deflecting means for applying a deflecting force and bending the distal end region of the second guide tube in a second articulated position. The second articulated position may be different than the first articulated position.

Yet another aspect of the invention provides devices, systems, and methods including a steerable guide catheter system, the system comprising a first guide tube having a length and defining an open interior lumen, the first guide tube lumen adapted for accommodating passage of an operative endovascular tool, a second guide tube having a length and defining an open interior lumen, the second guide tube lumen adapted for accommodating the first guide tube, and a handle assembly.

The handle assembly may comprise a first deflecting means coupled to a distal end region of the first guide tube to apply a deflecting force to bend the distal end region of the first guide tube, the first deflecting means adapted to bend the distal end region in a first articulated position, a second deflecting means coupled to a distal end region of the second guide tube to apply a deflecting force to bend the distal end region of the second guide tube, the second deflecting means adapted to bend the distal end region in a second articulated position, and instructions for use describing the use of the steerable guide catheter system, the instructions comprising the operations of introducing into a vessel the steerable guide catheter, advancing the steerable guide catheter to the targeted site in the vessel, manipulating the first deflecting means for applying a deflecting force and bending the distal end region of the first guide tube in a first articulated position, and manipulating the second deflecting means for applying a deflecting force and bending the distal end region of the second guide tube in a second articulated position.

The second articulated position may be different than the first articulated position. The operative tool may also be included with the system, the operative tool adapted to apply at least one fastener to tissue while residing in the guide catheter.

The instructions for use may further include instructions comprising passing the operative tool through the guide catheter, and operating the operative tool while residing in the guide catheter to apply at least one fastener to tissue.

Another aspect of the invention provides devices, systems, and methods including a steerable guide catheter comprising a first guide tube having a length and defining an open interior lumen, the first guide tube lumen adapted for accommodating passage of an operative endovascular tool, and a handle assembly. The handle assembly may comprise a first deflecting means coupled to a distal end region of the first guide tube to apply a deflecting force to bend the distal end region of the first guide tube, the first deflecting means adapted to bend the distal end region in a first articulated position, and a second deflecting means coupled to the distal end region of the first guide tube to apply a deflecting force to bend the distal end region of the first guide tube, the second deflecting means adapted to bend the distal end region in a second articulated position.

The second articulated position may be different than the first articulated position. An operative tool may be included that applies one or more fasteners to tissue.

The steerable guide catheter may also include a second guide tube having a length and defining an open interior lumen, the second guide tube lumen adapted for accommodating the first guide tube, and the second deflecting means coupled to the distal end region of the second guide tube to apply a deflecting force to bend the distal end region of the second guide tube, the second deflecting means adapted to bend the distal end region in the second articulated position. The second guide tube may comprise a length that is shorter than the length of the first guide tube.

BRIEF DESCRIPTION OF THE DRAWINGS

FIG. 1 is a perspective view of a healthy aorta showing the extent of the aorta from the aortic root, through the aortic arch, the descending thoracic aorta, and to the abdominal aorta and aortic bifurcation.

FIGS. 2A to 2C are perspective views of diseased aortas, showing the extent to which aneurysms may deform the aorta.

FIG. 6D is a side view of an additional embodiment of an endovascular graft that forms a part of the system shown in FIG. 4, the unsupported graft including a proximal portion with a first diameter, and a tapered portion extending to a distal portion have a second diameter smaller than the first diameter.

FIG. 6E is a side view of an additional embodiment of an endovascular graft shown in FIG. 6D, the unsupported graft including a most proximal stent not extending beyond the proximal edge of the graft, and without a distal stent.

FIG. 6F is a side view of an additional embodiment of an endovascular graft that forms a part of the system shown in FIG. 4, the unsupported graft including a curved portion adapted for placement in a tortuous vessel, and including a most proximal stent not extending beyond the proximal edge of the graft, and without a distal stent.

FIG. 8A is a view of the delivery system for the endovascular graft, which forms a part of the system shown in FIG. 4.

FIGS. 8B and 8C are perspective views of the top and bottom of the control handle of the delivery system shown in FIG. 8A.

FIG. 8F is a view of the distal end of the delivery system showing the retracted and advanced positions of the slidable release jacket as shown in FIG. 8E, and showing a supported graft attached to the delivery system.

FIG. 10B is a perspective view of the guide tube from the first steerable endovascular guide nested within the second steerable endovascular guide, the nested system adapted to guide the staple applier through at least one resolved angle and to apply an apposition force to conform the shape of the endovascular graft to be secured to the vessel wall.

FIG. 10C is an enlarged view of the handle of the first steerable endovascular guide shown in FIG. 10A.

FIG. 10D is a view of an alternative embodiment of a steerable endovascular guide shown in FIG. 10B, showing the steerable endovascular guide as a single guide device incorporating the features of the first steerable guide and the second steerable guide.

FIG. 10E is a view of an additional alternative embodiment of a steerable endovascular guide, showing the steerable endovascular guide as a single handle guide device with a single steerable guide tube adapted for steering in multiple directions.

FIG. 11A is a view of an endovascular fastener or staple that forms a part of the system shown in FIG. 4.

FIG. 11B is a view of a cassette to hold a plurality of endovascular fasteners, as shown in FIG. 11A, and to present the fasteners for loading in the staple applier, which also forms a part of the system shown in FIG. 4.

FIG. 12A is a view of a fastener applier for implanting a fastener as shown in FIG. 11A, which forms a part of the system shown in FIG. 4.

FIG. 12B is an enlarged view of the handle of the fastener applier shown in FIG. 12A, and showing the controls available to the user.

FIG. 12C is a view showing the manipulation of the fastener applier shown in FIG. 12A in loading a fastener from the cassette shown in FIG. 11B.

FIG. 13A is an anatomic view showing the driven member at the distal end of the fastener applier (and positioned within the catheter of the two segment steerable guide system) prior to being driven to implant a fastener in a graft and adjacent tissue, to secure the position of the graft, and showing the two segment steerable guide system adapted to guide the fastener applier through at least one angle to reach tortuous locations for fastener implant.

FIG. 14B is a view showing the fastener applier shown in FIG. 14A nested within the two segment steerable endovascular guide system of a type shown in FIG. 10B, showing how the indicia, which is visible to a naked eye, marks when the driven member rests at a desired distance within the steerable guide system just short of the terminus of the guide tube of the first steerable guide and therefore out of contact with tissue.

FIG. 14C is a close-up view showing the distal end of the two segment steerable guide system when the indicia visible at the proximal portion of the applier catheter marks when the actuated member rests at a desired distance within the first guide tube short of the terminus of the first guide tube and therefore out of contact with tissue.

FIGS. 16A to 16K are anatomic views of manipulation of the components of the system shown in FIG. 4 in placing a prosthesis in a descending thoracic aortic aneurysm, which manipulations can be incorporated within an instruction for use associated with a kit like that shown in FIG. 5.

DESCRIPTION OF THE PREFERRED EMBODIMENT

Figure 2B:
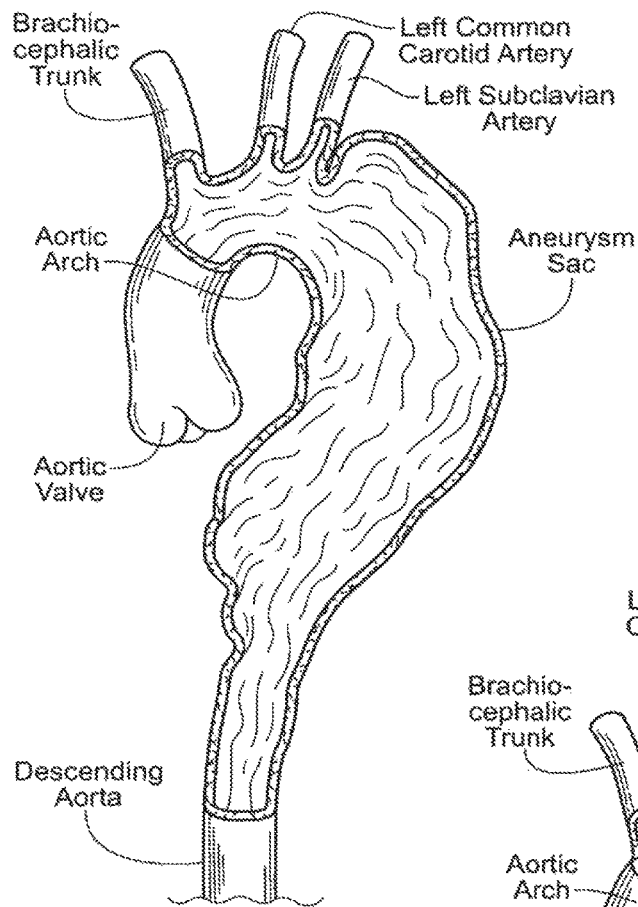

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

This specification discloses various catheter-based devices, systems, and methods for delivering and implanting staples and prostheses, including radially expandable prostheses in the body lumens. For example, the various aspects of the invention have application in procedures requiring the repair of diseased and/or damaged sections of a hollow body organ and/or blood vessel. The devices, systems, and methods that embody features of the invention, are also adaptable for use with systems and surgical techniques that are not necessarily catheter-based.

The devices, systems, and methods are particularly well suited for treating aortic dissections and aneurysms of the aorta, including those that occur in the thoracic region between the aortic arch and renal arteries, as well as aneurysms that also occur in the abdominal region, usually in the infrarenal area between the renal arteries and the aortic bifurcation. For this reason, the devices, systems, and methods will be described in this context. Still, it should be appreciated that the disclosed devices, systems, and methods are applicable for use in treating other dysfunctions elsewhere in the body, which are not necessarily aorta-related.

When referring to a prosthesis, i.e., an endovascular graft or its components that are intended to be implanted in a vessel or body organ, the terms "proximal" and "distal" will be used to describe the relation or orientation of the graft with respect to the heart after implantation. Therefore, the term "proximal" will be used to describe a relation or orientation of the graft that, when implanted, is toward the heart, and the term "distal" will be used to describe a position or orientation of the graft that, when implanted, is away from the heart, i.e., toward the feet.

When referring to implantation apparatus or devices that are manipulated by a physician or operator in order to implant the endovascular graft or its components, the terms "proximal" and "distal" will be used to describe the relation or orientation of the apparatus or device with respect to the operator as it is used. Therefore, the term "proximal" will be used to describe a relation or orientation of the apparatus or device that, when in use, is positioned toward the operator (i.e., at the handle end of the device), and the term "distal" will be used to describe a position or orientation of the apparatus or device that, when in use, is positioned away from the operator (i.e., at the other end of a catheter or the like away from the handle).

I. Aortic Abnormalities

A healthy aorta, the body's largest artery, has a general shape like the handle portion of a walking cane (see FIG. 1). The short length of the curved handle comes out of the heart and curls through the aortic arch. Multiple smaller arteries branch off at the aortic arch to serve the head and arms. The aorta continues to descend through the chest cavity into the abdomen and separates to provide blood to the abdominal organs and both legs. Various abnormalities may affect the aorta, most of which are considered potentially life-threatening. Prevalent aortic abnormalities include aortic aneurysms and aortic dissections, as non-limiting examples.

Figure 2C:
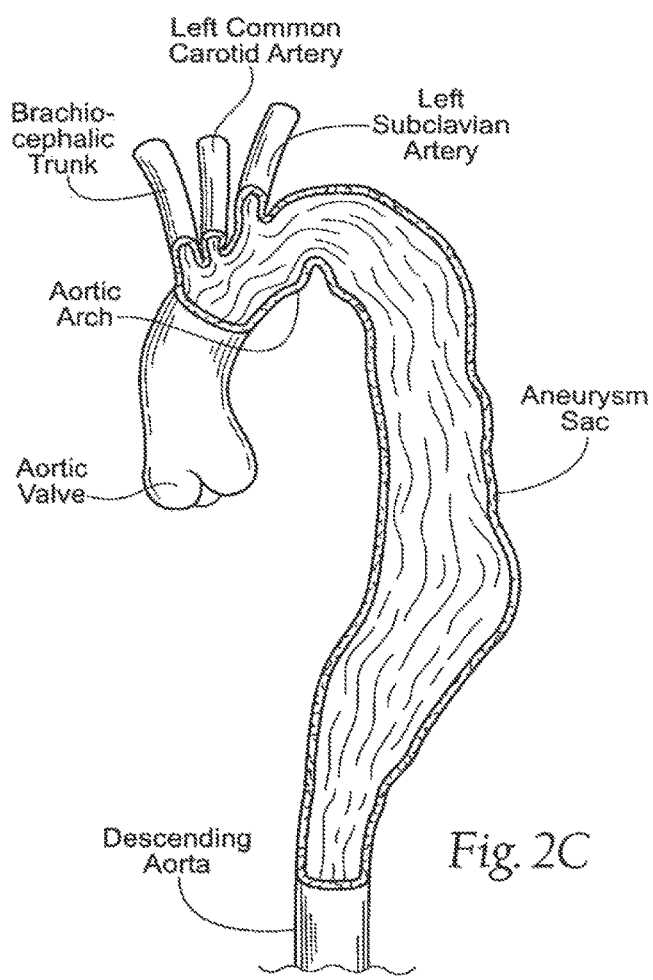

Aneurysms may affect one or more segments of the thoracic aorta, including the ascending aorta, the arch, and the descending thoracic aorta, a thoracic aortic aneurysm (TAA) can be described as an expanded (bulging) section(s) of the wall of the aorta, and is considered a life-threatening condition. Thoracic aortic aneurysms of any size can cause significant short- and long-term mortality due to rupture and dissection. FIGS. 2A, 2B, and 2C show examples of aortas having diseased tissues and difficult cases where the left subclavian artery ostium is distal to the aortic arch. Relative positions of the aneurysmal tissues in the tortuous aortic arch can be seen, as can and relationship to the brachiocephalic trunk, left common carotid artery, and the left subclavian artery. Often the left subclavian artery provides a landmark for positioning of an endovascular graft (to be described in greater detail below).

Common causes of a thoracic aortic aneurysm include hardening of the arteries (atherosclerosis), degeneration of the media of the aortic wall, as well as from local hemodynamic forces. Additional risk factors include various connective tissue disorders such as Marfan syndrome, previous dissection of the aorta, and trauma such as falls or motor vehicle accidents. They also sometimes occur in people who have bicuspid aortic valves.

Figure 3A:
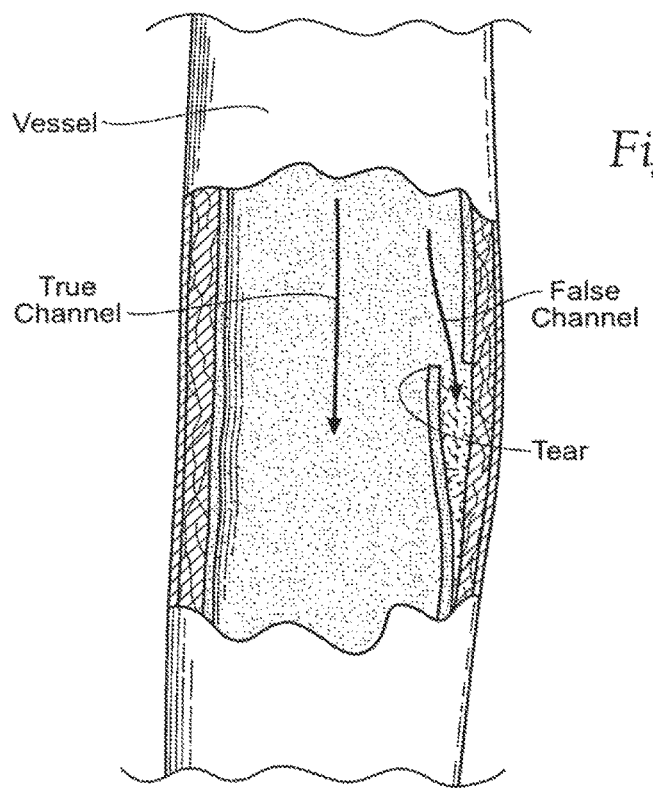
FIGS. 3A and 3B are perspective views of diseased aortas, showing aortic dissections.
Figure 3B:
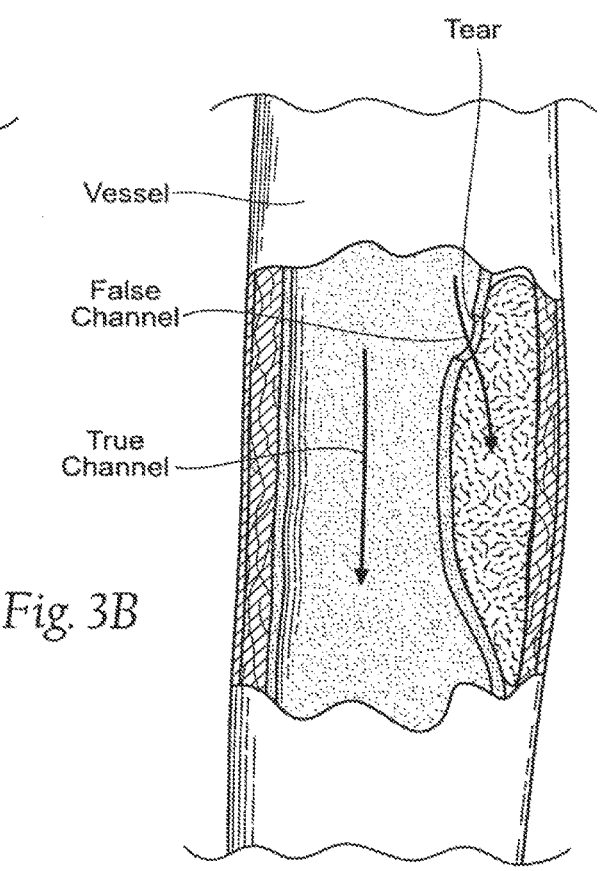

An aortic dissection is a perforation or tear in the lining of the aorta. The tear allows blood to flow between the layers of the aortic wall, with the force of the blood forcing the layers of the wall apart. FIGS. 3A and 3B show views of aortic dissections. An aortic dissection is a medical emergency and can quickly lead to death. If the dissection tears the aortic wall completely open, massive and rapid blood loss occurs.

The tearing of the inner lining of the aorta causes the blood to separate along the wall of the artery. This generally causes two channels in the vessel, with one channel referred to as the true channel and the other channel referred to as the false channel. As can be seen in FIGS. 3A and 3B, the tear allows the blood to create the false channel. With each heartbeat, the artery may progressively tear more and more with blood propagating down the false channel blocking off the true channel and the flow of blood to some or all of the branches of the aorta.

Aortic dissections can be classified by the Stanford method into a type A or type B depending on the location and the extent of the dissection. Type A dissection, or proximal dissection, involves the ascending aorta and aortic arch, and may or may not involve the descending aorta. Type B dissection, or distal dissection, usually begins just distal to the ostium of the left subclavian artery, extending distally into the descending and abdominal aorta. If left untreated, the risk of death from aortic dissection can reach 30 percent within fifteen minutes after onset of symptoms and 75 percent by one week.

II. System Overview

Figure 4:
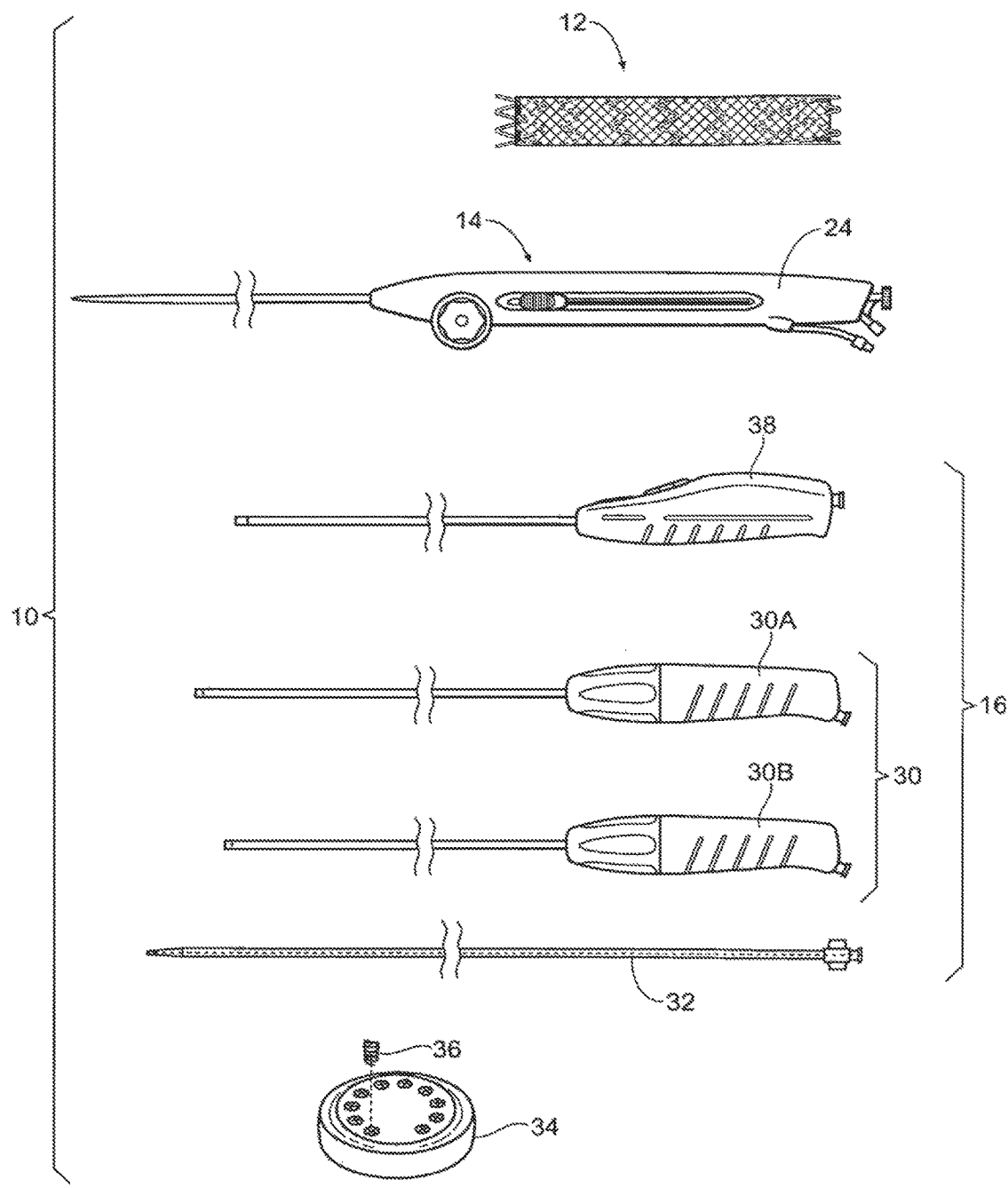
FIG. 4 is a view of the components of a system for repairing an endovascular aneurysm.

Aortic abnormalities, such as thoracic aortic aneurysms and aortic dissections with the appropriate anatomy, may now be repaired by the implantation of an endovascular prosthesis or graft. The implantation of staples alone may also be used for the repair of aortic dissections. FIG. 4 shows an exemplary system 10 for repairing an aortic abnormality. By way of example, the system 10 and/or components of the system are well suited for the repair of a descending thoracic aortic aneurysm and/or an aortic dissection, and will be described in this context. The system 10 comprises three primary components 12, 14, and 16.

The first component comprises an endovascular prosthesis or graft assembly 12. In use, the endovascular graft 12 is placed within a vessel at the site of the aortic abnormality. The endovascular graft 12 serves to exclude a portion of the vascular system from blood flow and blood pressure, in order to obtain exclusion of a portion of the vascular system, the endovascular graft must be sealed against the vascular wall, which requires apposition between the endovascular graft 12 and the vascular wall. The endovascular graft 12 must also be prevented from moving or migrating from its deployed position within the vascular system.

Figure 6A:
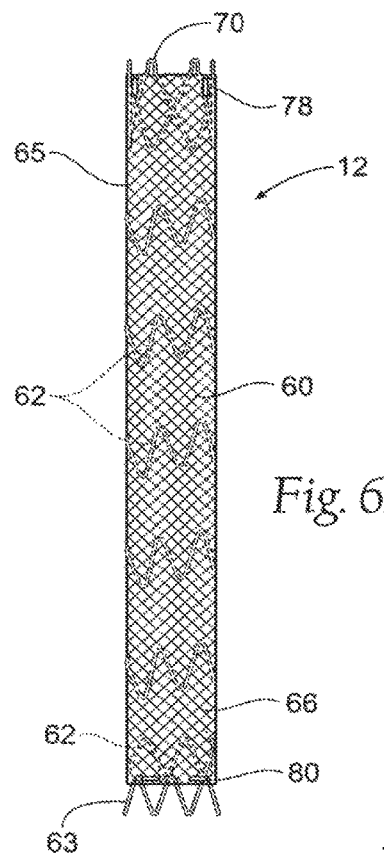
FIG. 6A is a side view of one embodiment of an endovascular graft that forms a part of the system shown in FIG. 4, the supported graft including a most proximal stent extending beyond the proximal edge of the graft.
Figure 6B:
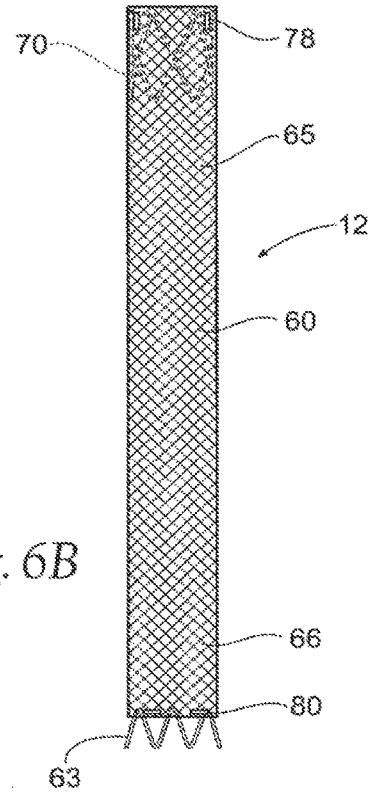
FIG. 6B is a side view of an additional embodiment of endovascular graft that forms a part of the system shown in FIG. 4, the unsupported graft including a distal stent and a most proximal stent not extending beyond the proximal edge of the graft.
Figure 6C:
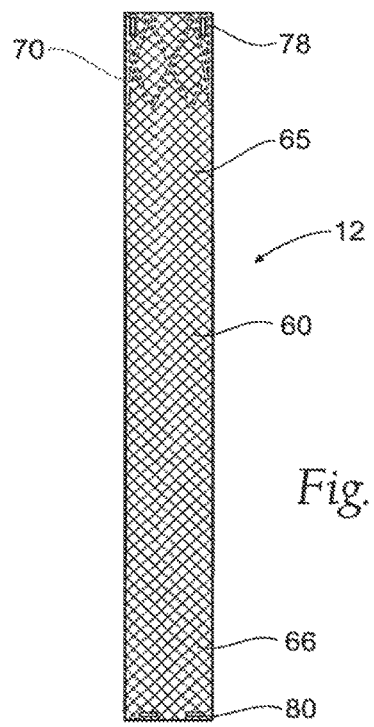
FIG. 6C is a side view of an additional embodiment of an endovascular graft shown in FIG. 6B, the unsupported graft including a most proximal stent not extending beyond the proximal edge of the graft, and without a distal stent.
Figure 6G:
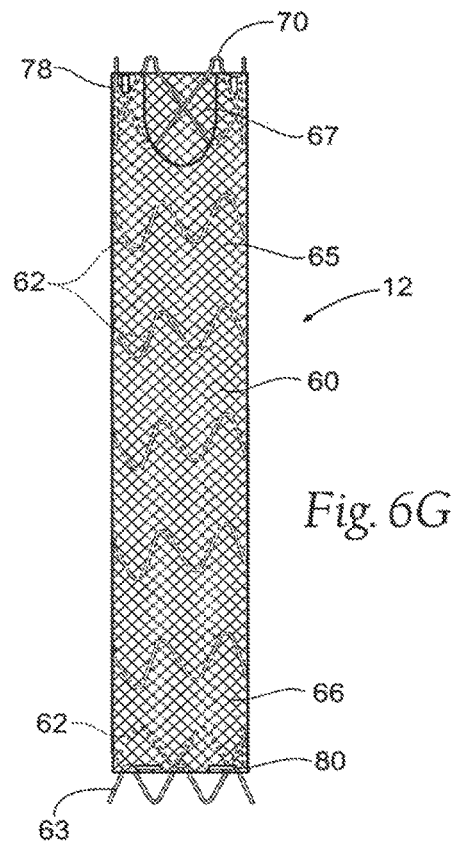
FIG. 6G is a side view of an additional embodiment of an endovascular graft that forms a part of the system shown in FIG. 4, the supported graft including a graft opening, the graft adapted to allow positioning of the proximal portion of the graft proximal to a branch artery (e.g., the left subclavian artery where healthy tissue may be present for securing the graft, and maintaining fluid flow communication to the branch artery.
Figure 6H:
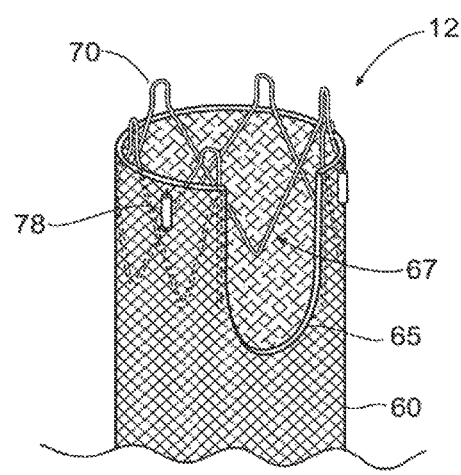
FIG. 6H in a close-up view of the opened or fenestrated portion of the endovascular graft shown in FIG. 6G.
Figure 6I:
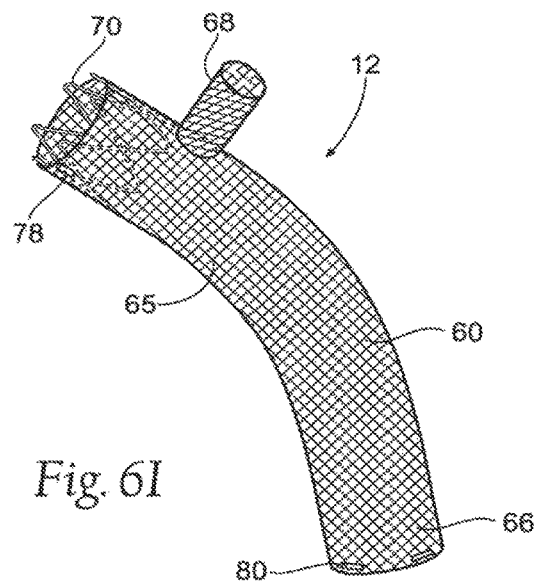
FIG. 6I is a perspective view of an additional embodiment of endovascular graft that forms a part of the system shown in FIG. 4, the branched graft includes a small ancillary branch protruding from the side of the graft, the branch 68 adapted to align with a vessel branch.
Figure 6J:
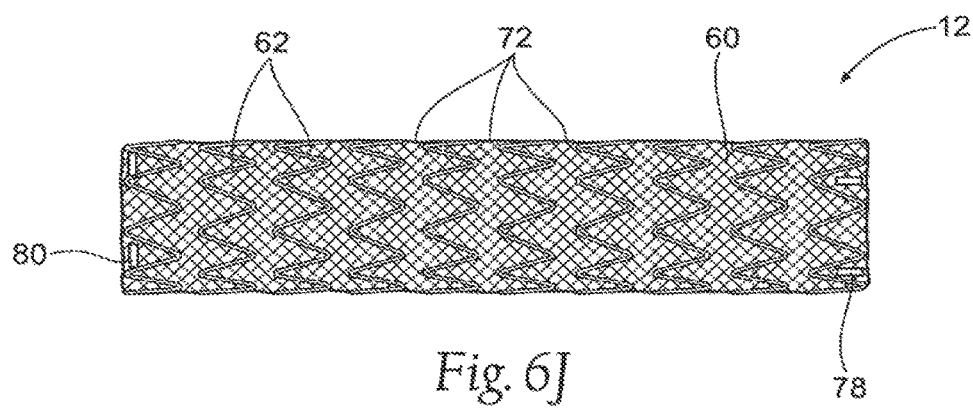
FIG. 6J is a view of an additional embodiment of endovascular graft that forms a part of the system shown in FIG. 4, the graft including areas adapted for preferential binding/folding, allowing the graft to better conform to angled or tortuous anatomy.
Figure 6K:
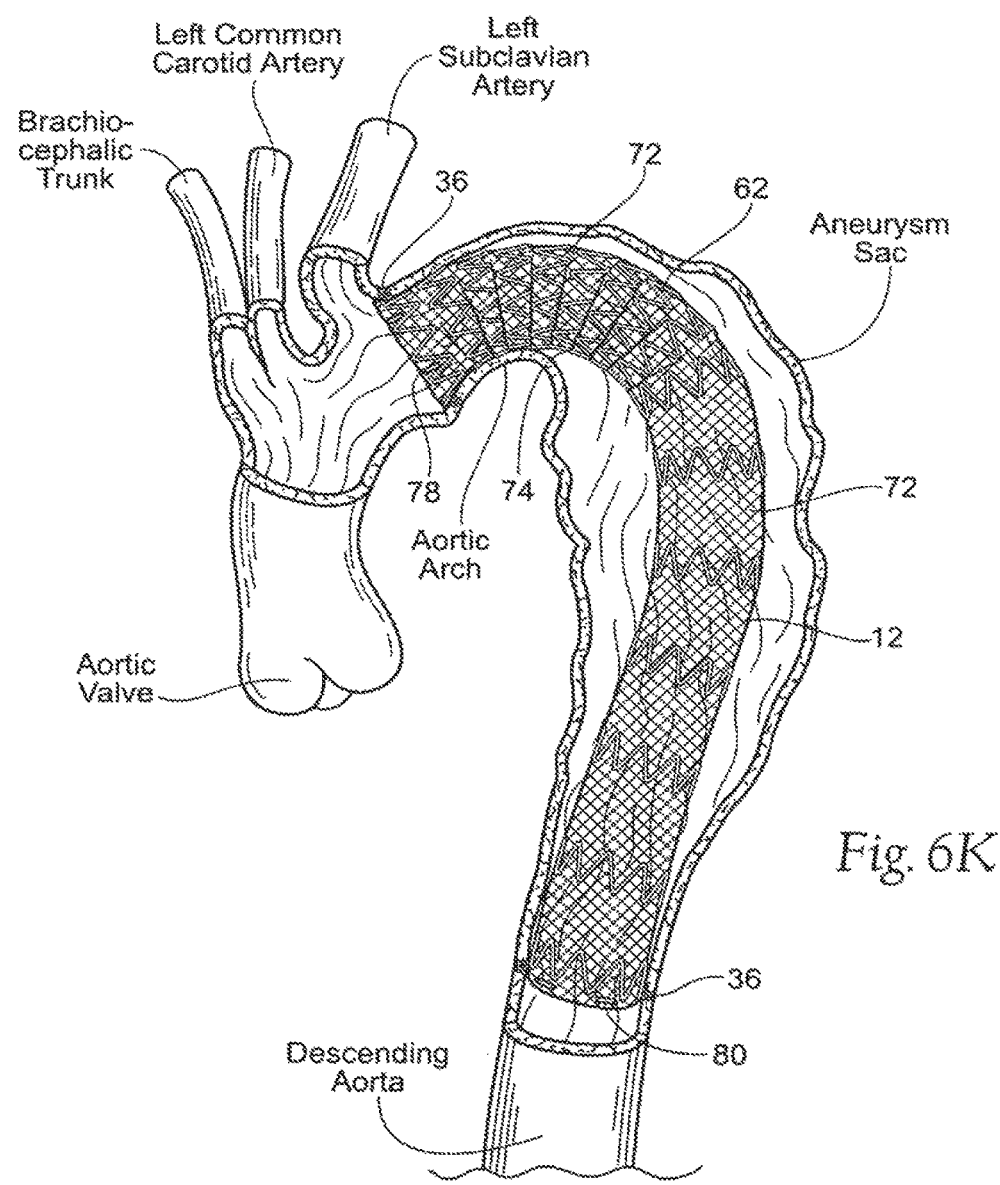
FIG. 6K is a view of the graft shown in FIG. 6J, showing the graft implanted in a tortuous vessel.
Figure 6L:
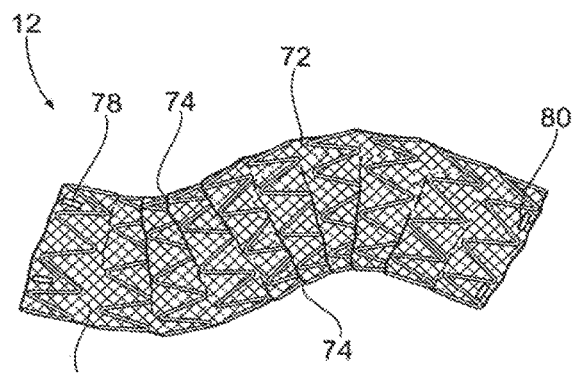
FIG. 6L is a view of the graft shown in FIG. 6J, showing the ability of the graft to bend/fold in a multi-curved configuration.
Figure 6M:
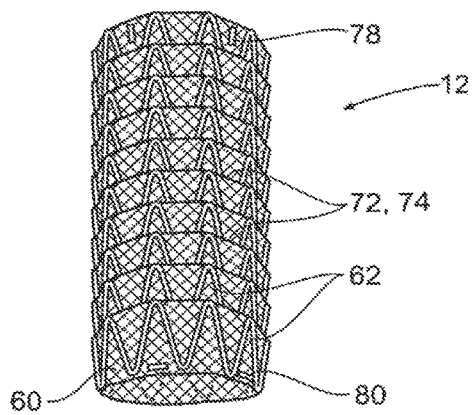
FIG. 6M is a view of the graft shown in FIG. 6J, showing the graft in a compressed configuration, the graft having the ability to be processed to bend/fold at predefined locations.
Figure 7A:
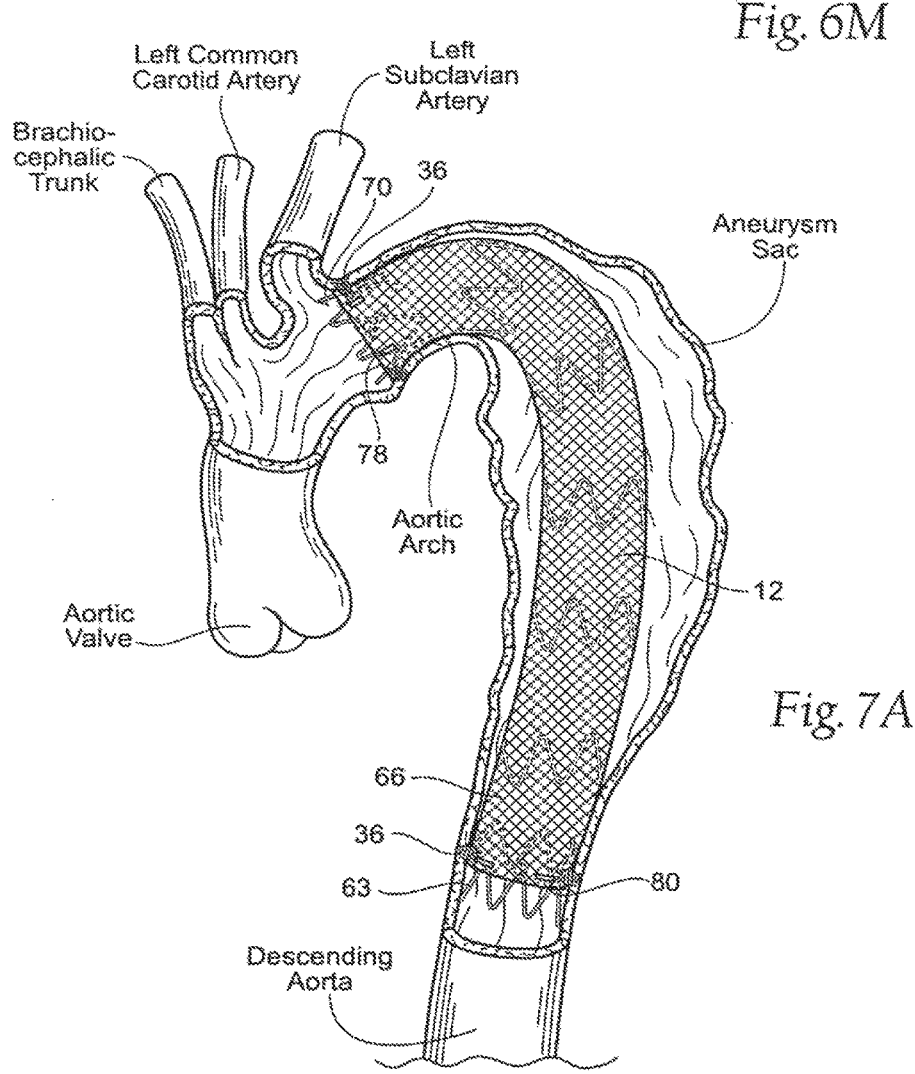
FIG. 7A is an anatomic view of a representative graft assembly implanted within a descending thoracic aortic aneurysm (TAA).
Figure 7B:
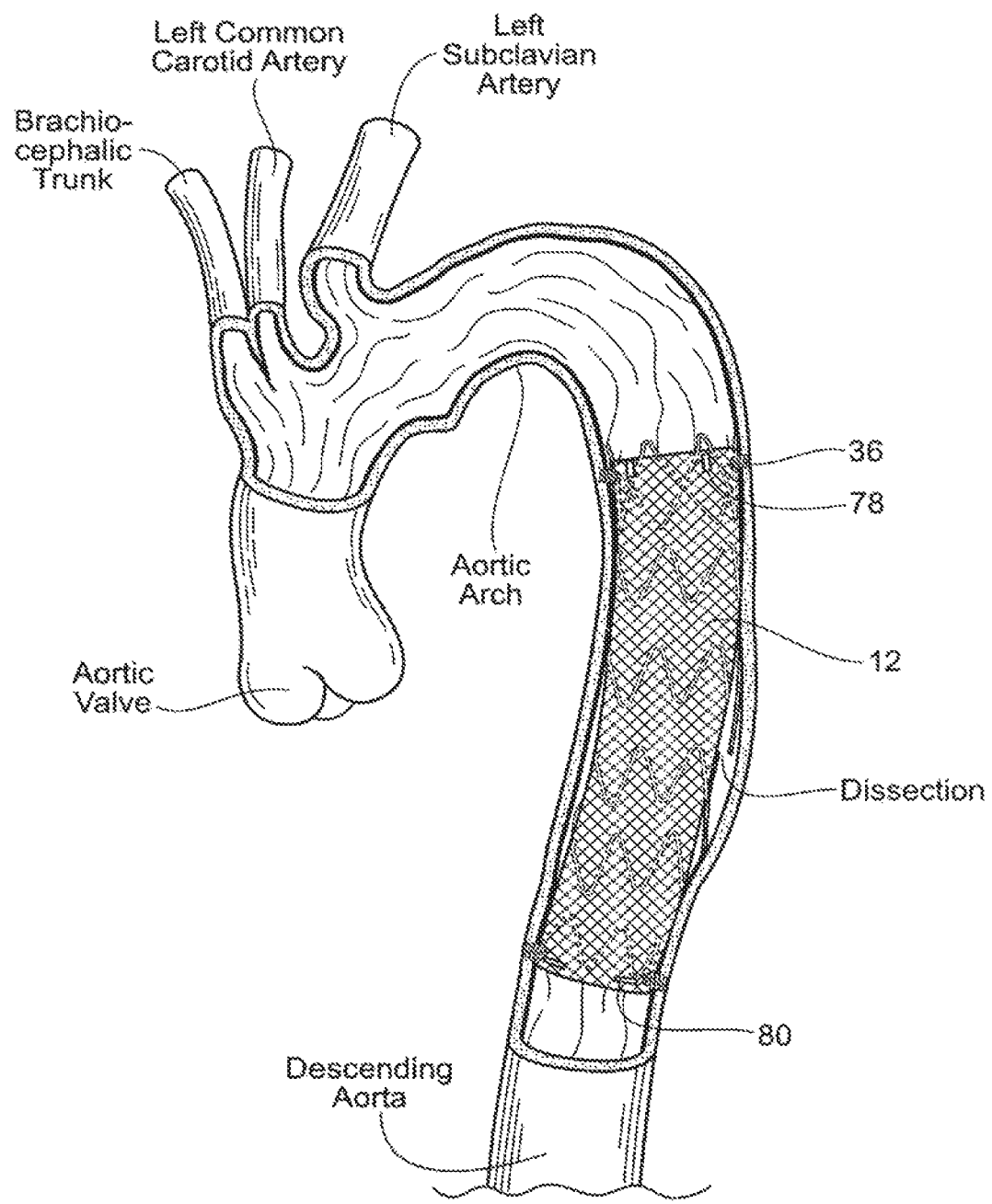
FIG. 7B is an anatomic view of a representative graft assembly implanted within a descending thoracic aorta, the graft positioned to repair an aortic dissection.

In the illustrated embodiments, the endovascular graft 12 is placed and secured within the aortic arch, e.g., at or near the left subclavian artery and extends past the site of the aneurysm and into the descending aorta (see FIG. 7A). FIG. 7B shows the endovascular graft 12 placed and secured within the descending aorta and extending past the site of a dissection. Additional embodiments of a graft assembly 12 are shown in FIGS. 6B through 6M.

The second component 14 comprises an endovascular delivery system for introducing and deploying the endovascular graft 12 using an endovascular approach. In the illustrated embodiment, in which the endovascular graft 12 comprises a single lumen body, a single endograft delivery component 24 may be provided. In alternative embodiments incorporating modular endovascular graft components, there may be individual corresponding endograft delivery components provided.

The third component 16 comprises an endovascular stapling system. In one embodiment, the endovascular stapling system 16 may be used to attach one or more regions of the endovascular graft 12 to the vessel wall with one or more endovascular staples. The endovascular stapling system 16 may also be used for implanting one or more endovascular staples without including an endovascular graft 12, the endovascular staples serving to close the entrance of the dissection to blood flow.

In one embodiment, the endovascular stapling system 16 comprises a steerable endovascular guide system 30 comprising a first steerable guide 30A and a second steerable guide 30B, an obturator 32, a cassette 34 holding a plurality of endovascular staples 36, and an endovascular fastening device, i.e., a staple applier 38. In an alternative embodiment, the two steerable guide catheters 30A and 30B may be combined into one operational handle with two steerable guide catheters. The steerable endovascular guide system 30 is sized and configured to provide at least one angle, rotational positioning, and relative positioning (axially) between the two guide catheters and preferably two or more angles with rotational positioning and relative positioning between the two guide catheters.

In use, the steerable endovascular guide system 30 establishes an endovascular path to the targeted site where the endovascular graft 12 has been positioned, and may be partially or fully deployed. The steerable endovascular guide system 30 is adapted to be manipulated by flexure and rotation in at least one direction or angle to provide the staple applier 38 access to successive sites, including difficult to reach sites due to tortuous anatomy of the vessel. The endovascular staple applier 38, carrying one or more endovascular staples 36, is guided by the two segment (30A and 30B) steerable endovascular guide system 30 to the successive sites. Once positioned, individual endovascular staples 36 are implanted, to penetrate the endovascular graft 12 (if used) and adjacent vessel wall. The endovascular staple applier 38 is actuated to implant individual endovascular staples 36 into selected region or regions of the endovascular graft 12 and adjacent vessel wall, to attach the endovascular graft 12 to the vessel wall.

The stapling system is adapted to apply an apposition force, i.e., resolution of force, to the endovascular graft 12 to modify the shape or form of the endovascular graft to conform to the shape of the vessel wall. This resolution of force can be utilized to deflect a portion or portions of the endovascular graft against the vessel wall to implant an endovascular staple, i.e., a fastener. After the conformance is obtained, a fastener or fasteners are implanted through the endovascular graft 12 and into the vessel wall. The fastener(s) maintain the shape of the modified configuration of the endovascular graft. This modified shape enables the endovascular graft 12 to obtain apposition between the graft 12 and the tortuous wall(s) of the vessel, and to exclude a portion of the vascular system.

III. System Kit

Figure 5:
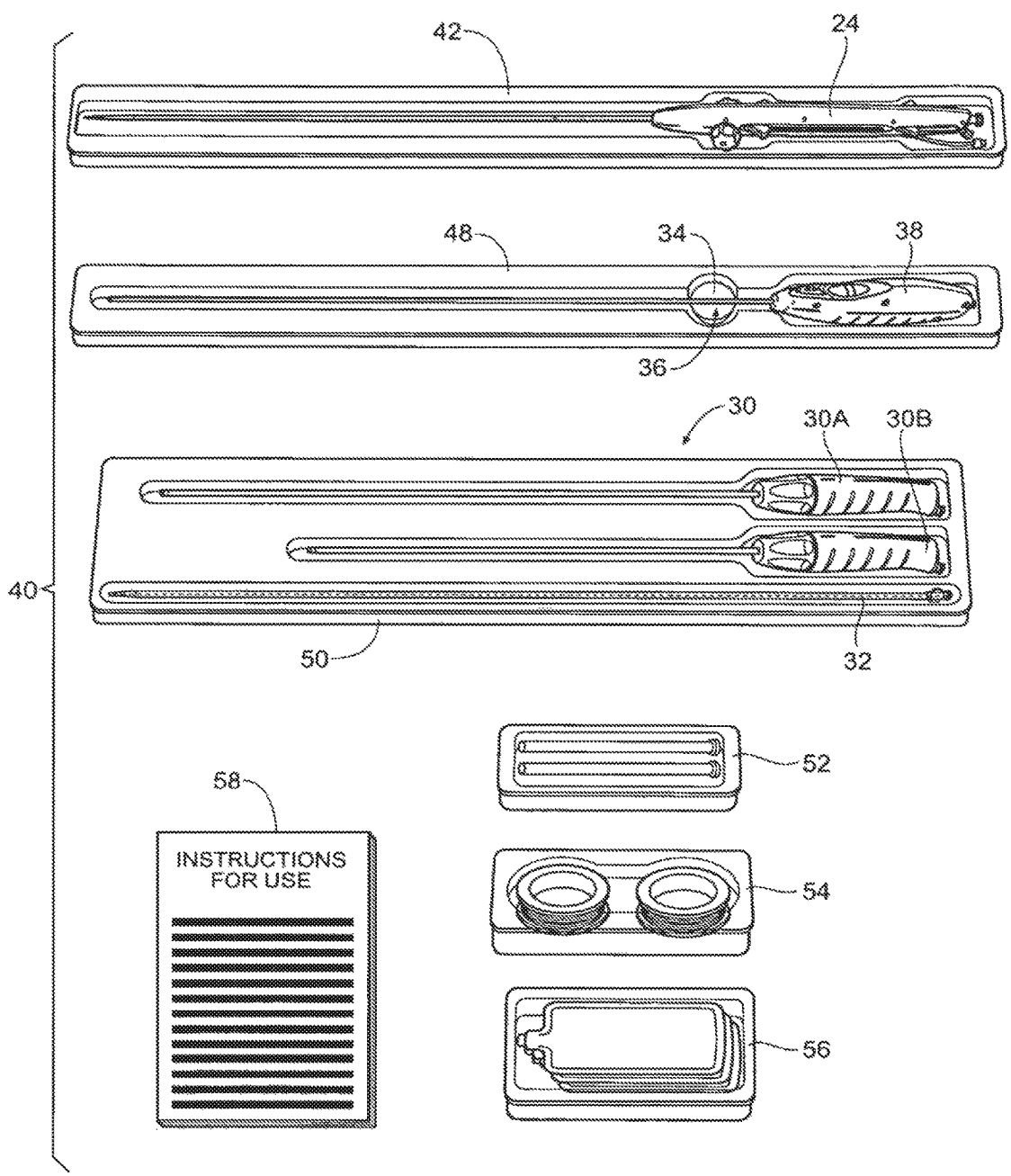
FIG. 5 is a view of the components of the system shown in FIG. 4 consolidated for use in a multiple piece kit, along with instructions for their use.

As FIG. 5 shows, the various tools and devices as just described, comprising the system 10, can be consolidated for use in a multiple piece functional kit 40. It is to be appreciated that the various tools and devices are not necessarily shown to scale.

The kit 40 can take various forms. In the illustrated embodiment, the kit 40 comprises an assemblage of individual packages 42, 48, 50, 52, 54, and 56, each comprising a sterile, packaged assembly. One or more of the packages may include an interior tray or card made, e.g., from die cut cardboard, plastic sheet, or thermo-formed plastic material, which hold the contents. The kit 40 also preferably includes instructions or directions 58 for using the contents of the packages to carry out a desired procedure. A desired procedure using the contents of the kit 40 shown in FIG. 5 will be described in greater detail later.

The instructions for use 58 can, of course vary. The instructions for use 58 can be physically present in one or more of the packages, but can also be supplied separately. The instructions for use 58 can be embodied in separate instruction manuals, or in video or audio recordings. The instructions for use 58 can also be available through an Internet web page.

A. The Component Packages

The arrangement and contents of the packages can vary. For example, as shown in FIG. 5, the kit 40 comprises six packages 42, 48, 50, 52, 54, and 56, and instructions 58. Three of these packages 42, 48, and 50 provide the main components of the endovascular repair system 10 as described. The remaining packages 52, 54, and 56 provide ancillary components used in the deployment of the system 10, e.g., conventional vascular access sheaths (in package 52); conventional 0.035 inch guide wires (in package 54); and bags containing heparinized saline for catheter flushing and contrast for angiography (in package 56).

In package 42, the endovascular graft 12 is preloaded into the endograft delivery component 24. Housed within the package 42, the endovascular graft 12 and the corresponding delivery component 24 for the endovascular graft are supplied sterile to the user.

As further shown in FIG. 5, the kit 40 comprises an additional package 50 that provides the two segment (30A and 30B) steerable endovascular guide system 30 and at least one associated component; namely, the obturator 32. As previously described, the steerable endovascular guide system 30 may also comprise a single device having the combined features of the two separate catheters. The kit 40 also comprises an additional package 48 that provides the endovascular staple applier 38 and at least one associated component; namely, a cassette 34 holding a plurality of endovascular staples 36. Housed within the packages 48 and 50, the two segment steerable endovascular guide system 30 and the endovascular staple applier 38 and their associated components are supplied sterile to the user.

IV. System Components

A. The Endovascular Graft

In representative embodiments (see FIGS. 6A through 6M), the endovascular graft 12 is a single lumen endograft generally comprising two primary components: a graft 60 made of a biocompatible material, e.g., polyester, ePTFE, etc.; and optionally a most proximal stent or scaffold 70 made of a biocompatible metal or plastic material, e.g., stainless steel, nickel-titanium (Nitinol), etc. One or more stents or scaffolds 62 may also be included in the graft mid-body for additional support (supported graft). Supported grafts (with one or more stents 62) and unsupported grafts are possible. In addition, a distal stent 63 may or may not be included.

In a representative embodiment, the preferred length of the endovascular graft 12 is between 5 cm and 30 cm and most preferably between 10 cm and 25 cm. Although, it is to be appreciated that other lengths, such as 15 and 20 cm for example, are possible to accommodate different anatomic conditions and vessel abnormalities. Desirably, a range of dimensions for the diameter of the graft 12 are provided to accommodate different anatomic dimensions of patients.

The endovascular graft 12 may include a most proximal stent 70, e.g., with diamond or "V" shaped cells, which may be sewn to the inside or outside of the proximal portion 65 of the graft e.g., with braided or monofilament suture. The most proximal stent 70 is sized and configured to accommodate secure apposition to the vessel wall, for example, at the level of the aortic arch just below, or just beyond the left subclavian artery. At this tortuous location, the graft 12 and/or stent 70 may resolve to a more elliptical or oval shape, due to the curvature of the proximal portion of the endovascular graft within the aortic arch, which may bend or curve 90 degrees or more. The stapling system 16 is adapted to apply an apposition force to deflect a portion or portions of the proximal portion 65, or other portions of the graft 12 and/or the stent 70 against the vessel wall where the graft 12 does not naturally appose the vessel wall due to the curvature of the vessel wall, to conform the shape of the endovascular graft 12 to the vessel wall at the desired location to be secured. The ability to deflect a portion or portions of the endovascular graft is desirable because it allows the shape of the graft 12, or portions thereof, to be customized to the patient's anatomy.

In the embodiment shown in FIG. 6A, the stent 70 extends beyond the fabric, with the extension ranging from about 0.0 mm to about 15 mm, although a wider range is possible. A supporting stent 62 is shown in the graft 12. In an alternative embodiment shown in FIG. 6B, the stent 70 does not extend beyond the fabric. The grafts in FIGS. 6B and 6C are shown as an unsupported graft with a distal stent 63 and without a distal stent 63, respectively.

Additional embodiments of the graft 12 are possible to address a variety of anatomical configurations. FIG. 6D shows an unsupported tapered graft 12 wherein the proximal portion 65 includes a first diameter D1, and the distal portion 66 includes a second diameter D2. The first diameter may be greater than the second diameter in one embodiment and less than the second diameter in an alternative embodiment. The grafts in FIGS. 6D and 6E are shown as an unsupported graft with a distal stent 63 and without a distal stent 63, respectively.

FIG. 6F shows one embodiment of a curved graft 12 configuration. The curved graft may be used to aid in conformance with placement in the aortic arch or other tortuous locations. As a non-limiting example, the curved graft 12 is shown without the use of the distal stent. The curved graft may be initially woven in a straight configuration, and then processed (i.e., heat set on a curved mandrel) to take the predetermined curved shape.

FIG. 6G shows an additional alternative embodiment of the graft 12. The graft 32 includes an opening 67 in the proximal portion 65 which could accommodate fluid communication with a branch artery such as the left subclavian artery, for example, and allow the graft 12 to land further proximally in the thoracic aorta, where healthy tissue may be more readily available to secure the graft 12.

FIG. 6I shows another alternative embodiment of the graft 12. The branched graft 12 includes a small ancillary branch 68 protruding from the side of the graft, the branch 68 adapted to align with a vessel branch, such as the subclavian artery.

FIGS. 6J to 6M show yet another alternative embodiment of a graft 12. The tubular graft 12 includes areas 72 for preferential bending/folding. These preferential bending/folding areas 72 allow the graft 12 to better conform to angled or tortuous anatomy, in addition, the preferential bending/folding areas 72 bias the folds 74 in a direction that is most advantageous for blood flow (i.e., the folds go in the direction of blood flow). The preferential bending/folding areas 72 may also eliminate or reduce the contact between individual stents 62 (i.e., metal scaffolding components) when the graft is placed in angled or tortuous anatomy.

As can be seen in FIG. 6J, the graft 12 includes sufficient unstented graft areas 72 in-between the stents 62 in order to allow the bending/folding to occur. The width of the unstented graft area 72 may vary depending on the application and/or the location of implantation (see FIG. 6K for example). FIGS. 6K and 6L show the graft 12 in various curved configurations. As can be seen, the graft 12 is adapted to bend/fold (i.e., compress) at or near the inner radius of the curve, while the unstented graft area 72 at or near the outer radius of the curve is allowed to expand as needed.

The graft 12 may be preconfigured so the graft bends/folds at the unstented graft areas 72 as desired. A compressive force may be applied to successive stents 62 while radially pinching or squeezing the leading edge of one stent 62, to cause it and the unstented graft material 72 between the two stents to fold within the other stent 62. Using this method, the graft 12 may be partially or completely compressed as shown in FIG. 6M. Time and/or temperature may then be used to process the graft 12 to bend/fold in a predetermined manner. The bends/folds in the graft 12 may be made permanent with time and/or temperature configurations. Generally, the lower the temperature the longer the time it takes to achieve a desired configuration. In a preferred embodiment, a temperature between about 10 degrees Celsius to about 250 degrees Celsius may be used, and more preferably between about 30 degrees Celsius to about 150 degrees Celsius. The graft may be processed to varying levels of conformity using a range of times from about 1 second to several days.

The graft 12 may include scents 62, shown with diamond or "V" shaped cells, which may be sewn to the inside or outside of the graft, e.g., with braided or monofilament suture.

Predetermined arrays of radiopaque markers made from biocompatible materials with high radiopacity (e.g., tantalum, platinum or gold) are desirably attached to the endovascular graft 12 to assist with visualization under fluoroscopy. The markers, like the stents, may be sewn to the graft, e.g., with braided or monofilament suture or can be attached to the stent. The arrays can vary. In the illustrated embodiments, there are four (4) proximal stent marker bands 78 and four (4) distal stent marker bands 80, although other combinations and positions are possible to aid in the placement of the graft.

Further details of representative constructions of the endovascular graft 12 can be found in co-pending, commonly owned U.S. patent application Ser. No. 11/254,444, filed Oct. 20, 2005, and entitled "Devices, Systems, and Methods for Prosthesis Delivery and implantation, Including a Prosthesis Assembly," which is incorporated herein by reference.

B. Endovascular Graft Implantation Components

1. The Endovascular Graft Delivery System a. General Overview

Figure 8D:
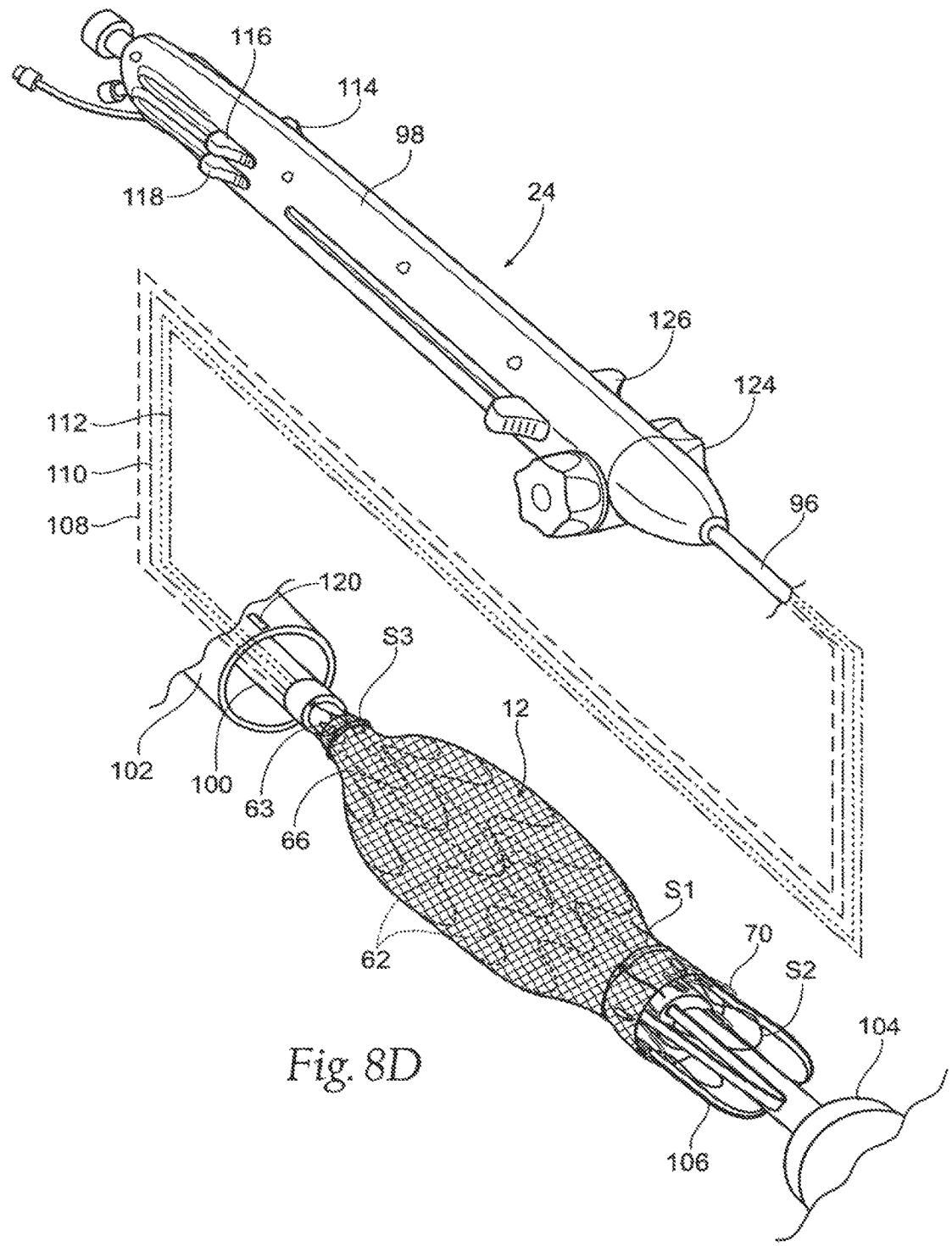
FIG. 8D is an enlarged perspective view of the distal end of the delivery system shown in FIG. 8A, with parts broken away to show the attachment of a supported endovascular graft to the delivery system and the release wire and/or wires and jacket controls that are coupled to the handle to affect a controlled stepwise release of the endovascular graft from the delivery system.

The endovascular graft assembly 12 is preloaded into the delivery system 24 (see FIG. 8A), which is a single use component that is supplied to the user within its package 42 in a sterile condition (see FIG. 5). The delivery system 24 is sized and configured to facilitate accurate placement of the endovascular graft 12 and to allow the physician to maintain control of the endovascular graft 12 while the endovascular staples 36 are applied.

In the illustrated embodiment, the delivery system 24 comprises a delivery catheter 56 and a control handle 98 coupled to the proximal end of the delivery catheter 96. The delivery catheter 96 (see FIG. 8D) comprises a flexible inner assembly 100 and an outer graft retention jacket 102. The inner assembly 100 carries at its distal-most end a flexible radiopaque tracking nosecone 104.

When preloaded (see FIG. 8D), the endovascular graft 12 (a supported graft 12 is shown) may be attached to the inner assembly 100 in discrete locations. In this non-limiting example, the graft is attached in three locations, just proximal of the nosecone 104 (i.e., toward the handle 98), the proximal portion 65 of the graft may be secured by a releasable suture S1 to the inner assembly 100. Also just proximal of the nosecone 104, the inner assembly 100 may include a set of stabilizing arms 106 (or a releasable suture). In the illustrated embodiment, there are three stabilizing arms 106. The proximal portion 65 of the preloaded endovascular graft 12 may be attached to the three stabilizing arms by three releasable pull wires S2, each threaded through eyelets in a respective one of the distal ends of the stabilizing arms 106 and through adjacent graft material. The distal end 66 of the preloaded endovascular graft 12 may also be attached to the inner assembly 100 by a releasable suture S3. These sutures S1, S2, and S3 and release wires 108, 110, and 112 (or other release means) secure the endovascular graft 12 to the inner assembly 100 for deployment to the targeted implantation site.

In an alternative embodiment, the graft 12 can be attached to the inner assembly 100 in multiple discrete locations without using the proximal stabilizing arms, it is also to be appreciated that the stabilizing arms are not limited to attaching only the proximal portion 65 to the inner assembly 100. Stabilizing arms may be used to attach any portion of the graft 12 to the inner assembly, including the most proximal stent 70, a distal stent 63, the proximal portion 65, the distal portion 66, or any other portion of the graft 12.

Figure 9:
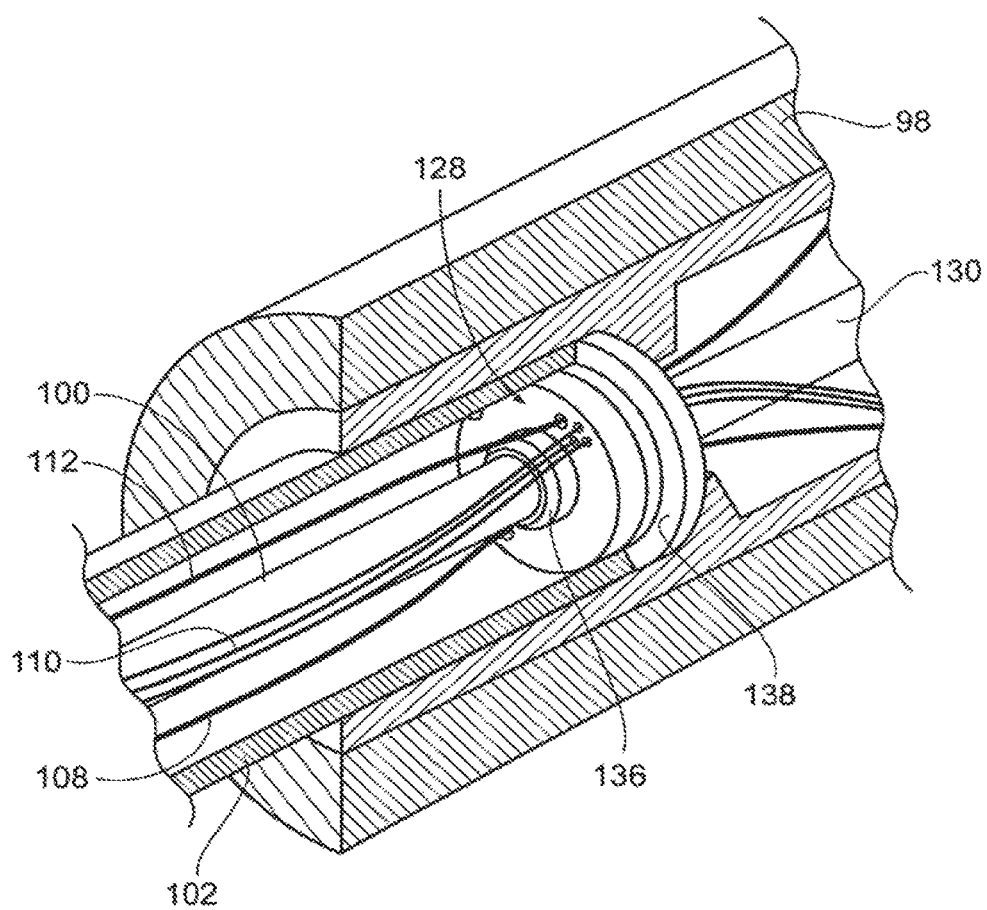
FIG. 9 is an enlarged view at a hemostatic seal assembly within the handle of the delivery system, showing the passage of the release wires through the seal assembly between the control mechanisms and the distal end of the delivery system (as shown in FIG. 8D).

The separate release wires 108, 210, and 112 extend from the handle 98 along the inner assembly 100 (see FIG. 9). The separate release wires 108 and 212 are independently coupled to the respective suture S1 holding the most proximal stent 70 (release wire 108), and the suture S3 at the distal portion 66 of the endovascular graft 12 (release wire 112). The release wires 210 are continuations of the release wires S2 threaded through the stabilizing arms 106 (as previously described), so that, in the illustrated embodiment, there are actually three release wires no, one for each arm 106. Controls 114, 116, and 118 on the handle 98 are coupled to the separate release wires 108, 110 (commonly coupled to the three wires), and 112, as will be described in greater detail later, to independently release the sutures or release wires at one location, without necessarily releasing the sutures or release wires at another location. The separate and independently controllable release wires 208, 110, and 112 make possible the release of the endovascular graft. 12 in a prescribed order, to deploy the endovascular graft 12 in a desired sequence during the graft deployment process, as will be described in greater detail later.

Figure 8E:
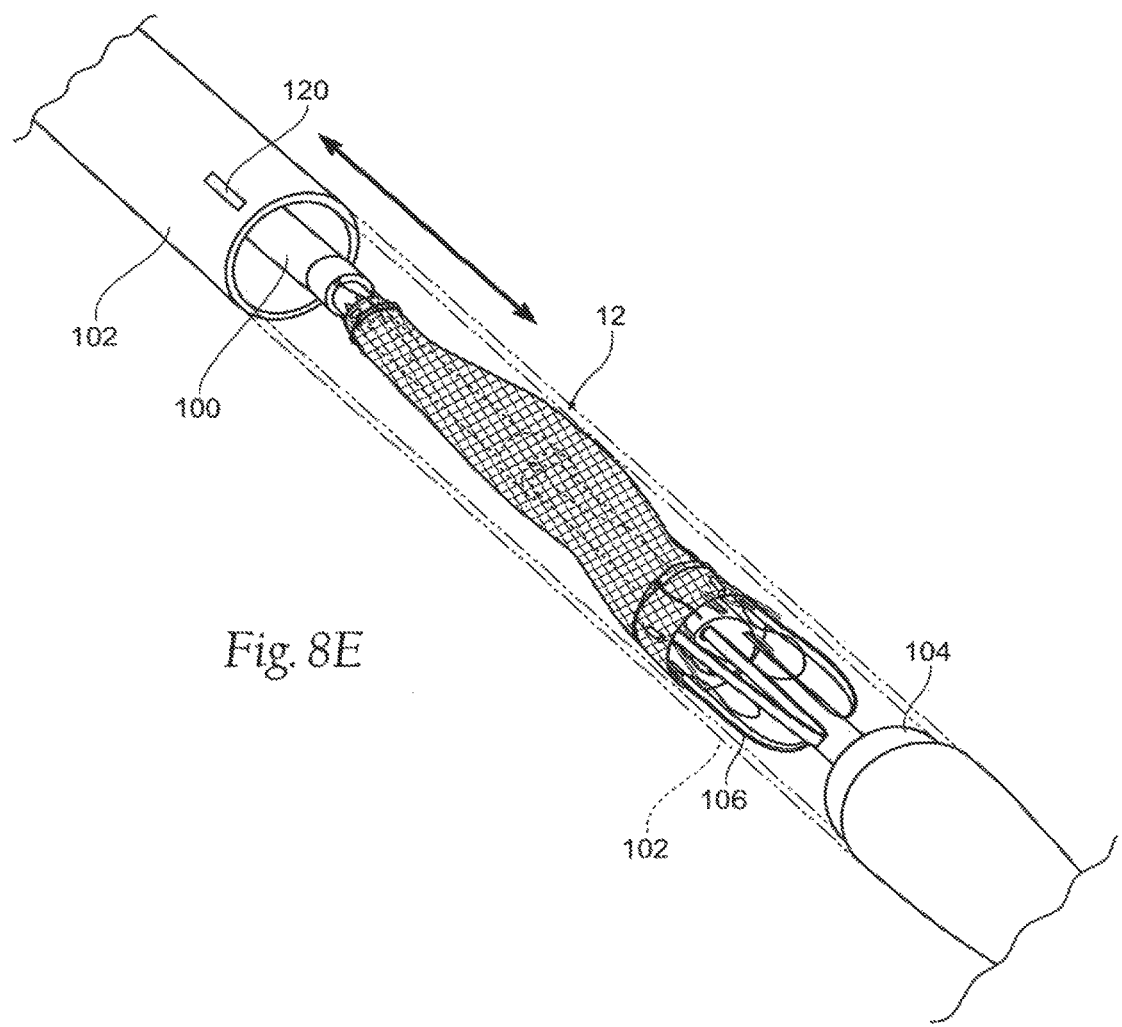
FIG. 8E is a view of the distal end of the delivery system showing the retracted and advanced positions of the slidable release jacket, with an unsupported graft attached to the delivery system.

The graft retention jacket 102 is sized and configured to slide over and along the inner assembly 100 from an advanced position over the preloaded endovascular graft 22 (shown in phantom lines in FIG. 8E) to a retracted position spaced away from the preloaded endovascular graft 12 (shown in solid lines in FIG. 8E). FIG. 8E shows an embodiment of an unsupported graft, and FIG. 8F shows an embodiment of a supported graft. One or more radiopaque marker(s) 120 is positioned at or near the leading edge of the graft retention jacket 102 to assist in visualization under fluoroscopy.

As can be seen in FIGS. 8B and 8C a jacket control mechanism 122 coupled to controls 124 and 126 on the handle 98 affects retraction of the graft retention jacket 102 in a stepwise fashion—using first control 124 and then control 126, as will be described later—as well as the re-advancement of the retention jacket 102 using the single control 126 after the graft 22 has been fully deployed and it is time to withdraw the delivery system.

When in its advanced position, the graft retention jacket 102 protects the preloaded endovascular graft 12 as it is advanced through the patient's vasculature. When in its retracted position, the graft retention jacket 102 frees the preloaded endovascular graft 12 for deployment by operation of the controls 224 and 126 on the handle 98 during the graft deployment process.

The actuating means on the control handle 98 (see FIGS. 8B and 8C) may include a jacket retraction knob 124 and a jacket retraction slide 126, which are coupled to the jacket control mechanism 122 just described. The jacket retraction knob 124 is actuated by rotation and is coupled to gear components oil the jacket control mechanism 122 within the handle 98. The gear components apply a mechanical advantage in response to rotation of the knob 124 sufficient to overcome the resistance of the graft retention jacket 102 to axial movement beyond the proximal portion of the graft and optionally the mid-body stent(s) 62, when included, of the endovascular graft 12. Once passed the proximal portion of the graft, the gear components of the jacket control mechanism 122 may be automatically released from the jacket retraction knob 124 (the knob 124 will accordingly spin freely), and subsequent control passes to the jacket retention slide 126. Pulling on the jacket retention slide 126 (which may not provide a mechanical advantage) suffices to complete the retraction of the jacket 102. This control sequence provides the physician with tactile feedback during the retraction of the jacket 102. After retracted in this manner, the jacket 102 can be advanced back toward the nosecone 104 using the jacket slide 126 when it is time to withdraw the delivery system after release of the graft 32.

In an alternative embodiment of the jacket control mechanism 122 within the handle 98, the delivery system 24 may have the ability to produce a mechanical advantage for the full length of the retraction of the graft retention jacket 102. The mechanical advantage produced may be disengaged by the physician at any point during the retraction of the jacket 102, and the mechanical advantage may be reengaged if desired, at any point during the retraction of the jacket 102. The mechanical advantage may be produced using the gear system as described, or may be produced by other means such as a reel and cable system, or an exterior threaded rod with an internal threaded component for example.

As previously described, the actuating components on the control handle may include the proximal release slide 114, the graft release slide 116, and the distal release slide 128. The proximal release slide 114 is coupled to the release wire 110 for the proximal portion 65 of the graft. The graft release slide 116 is coupled to the three separate release wires 110 for the stabilizing arms 106. The distal end release slide 118 is coupled to the separate release wire 212 for the distal portion 66 of the endovascular graft 12.

Once the graft retention jacket 102 is retracted (as just described), pulling on the proximal release slide 114 opens the proximal portion 65 of the graft. Pulling on the distal end release slide 118 opens the distal portion 66 of the endovascular graft 12. Despite opening the proximal portion 65 and the distal portion 66, the proximal portion 65 of the endovascular graft 12 remains attached to the inner assembly 100 of the endovascular graft delivery system. The physician maintains control of the endovascular graft 12 for further final positioning and for the application of the staples 36, as will be described in greater detail later.

Once positioned in a desired location and/or after insertion or implantation of staples to secure the endovascular graft 12 to the vessel wall, pulling on the graft release slide 116 releases the endovascular graft 12 from the stabilizing arms 106 and the delivery catheter 96.

Figure 8G:
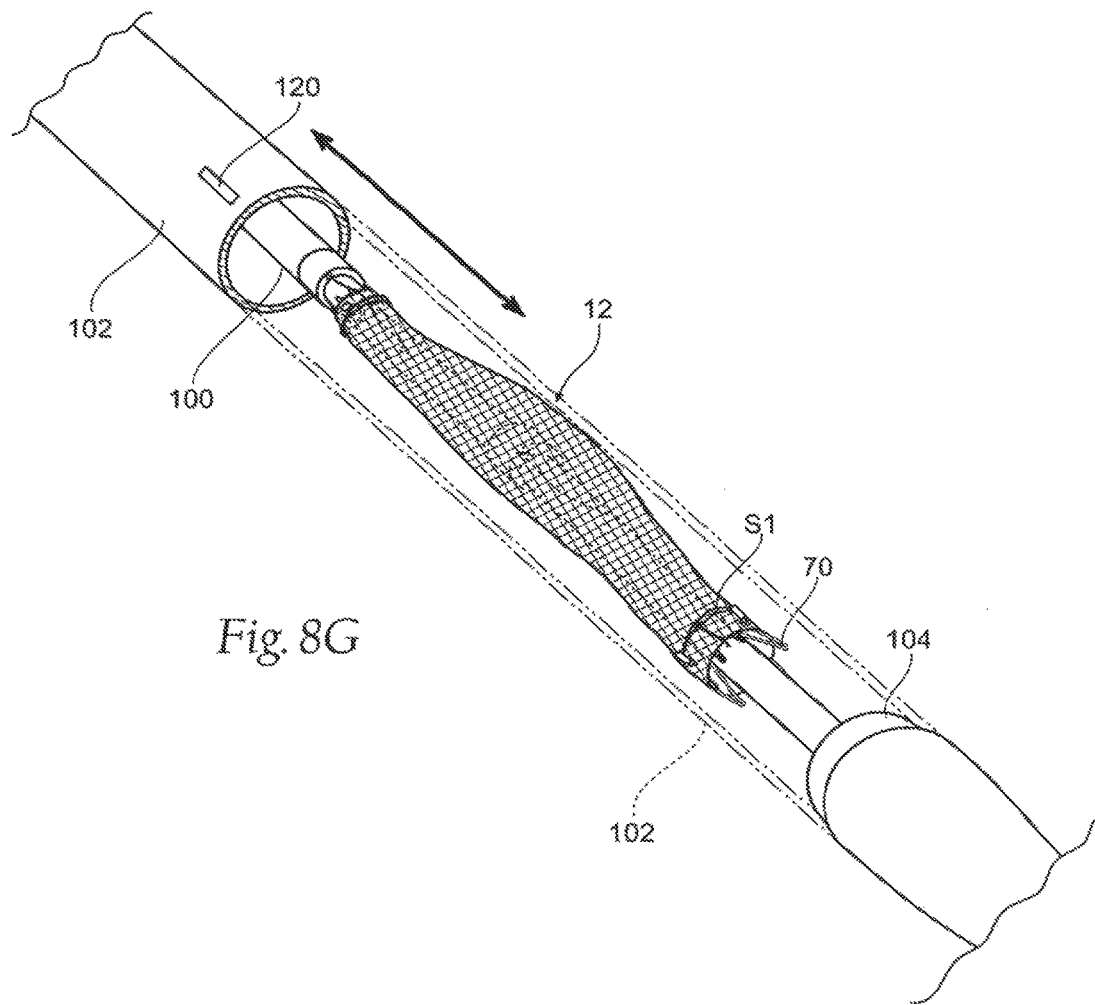
FIG. 8G is a view of the distal end of the delivery system snowing the retracted and advanced positions of the slidable release jacket as shown in FIG. 8E, and showing an alternative delivery system without stabilizing arms.

An alternative embodiment of the delivery catheter 96 is shown in FIG. 8G without stabilizing arms. In this embodiment, the endovascular graft 12 (an unsupported graft 12 is shown) may be attached to the inner assembly 100 at discrete locations. In this non-limiting example the graft is attached in two locations, just proximal of the nosecone 104, (i.e., toward the handle 98), with the proximal portion 65 of the endovascular graft 12 being secured by a releasable suture S1 to the inner assembly 100, and the distal end of the preloaded endovascular graft 12 may also be attached to the inner assembly 100 by a releasable suture S3. These sutures S1 and S3 secure the endovascular graft 12 to the inner assembly 100 for deployment to the targeted implantation site, as previously described. It is to be appreciated, as previously described, that the graft 12 can be attached to she inner assembly 100 in multiple discrete locations, and without using the proximal stabilizing arms, to maintain control of the graft 12. The use of release wires, for example, as described above may be used to attach the graft 12 to the inner assembly 100 to maintain control of the graft 12 while implantation of staples takes place.

If desired, and as shown in phantom lines in FIG. 8A, a stationary outer jacket 220 may be provided that extends for a distance from the proximal end of the handle 98 over the delivery catheter 96 (the jacket 102), which slides within the stationary outer jacket 220. The stationary jacket 220 provides a seal interface with a hemostatic valve of the introducer sheath at the access site. The stationary jacket 220 can be made of a suitable medical grade plastic, such as Fluorinated Ethylene Propylene (FEP) as a non-limiting example. The stationary outer jacket 220 provides column strength and lubricity to reduce friction during sliding actuation of the jacket 102.

In a representative embodiment, the handle 98 (e.g., near the sliding controls 114, 116, and 118 just described) includes a hemostatic seal assembly 126. As FIG. 9 shows, a flush passage 130 (for conveying heparinized saline to flush the delivery catheter 96 prior to deployment) communicates with the space between the inner assembly 100 and jacket 102 through the hemostatic seal assembly 128. As FIG. 9 also shows, the individual release wires 108, 110, and 112 for the proximal portion release slide 114, the graft release slide 116 (one release wire 110 for each stabilizing arm 106), and the distal end release slide 118, as previously described, also pass from the slide controls 114, 116, and 118 within the handle in a sealed fashion through the hemostatic seal assembly 128 for passage along the inner assembly 100 to the distal end of the delivery catheter 96, where they connect to their respective components, as previously described. The hemostatic seal assembly 126 allows flushing to occur and prevents blood, which can enter the space between the outer jacket 102 and the inner assembly 100 catheter tube during use, from entering the interior of the handle 98.

The delivery catheter 96 is desirably sized to present a minimum diameter according to the diameter of the endovascular graft 12 it carries. The delivery catheter 96 is desirably sized and configured with a lumen accommodating conventional over-the-wire delivery within a patient's vasculature, e.g., using a conventional 0.035 or 0.038 inch guide wire. In a representative embodiment, the overall length of the delivery catheter 96 (not including the handle 98) is preferably between 40 and 120 cm and most preferably between 60 and 110 cm.

Further details of representative constructions of a delivery system 24 can be found in co-pending, commonly owned U.S. patent application Ser. No. 11/255,116, filed Oct. 20, 2005, and entitled "Devices, Systems, and Methods for Prosthesis Delivery and Implantation," which is incorporated herein by reference.

2. Endovascular Stapling System

Figure 10A:
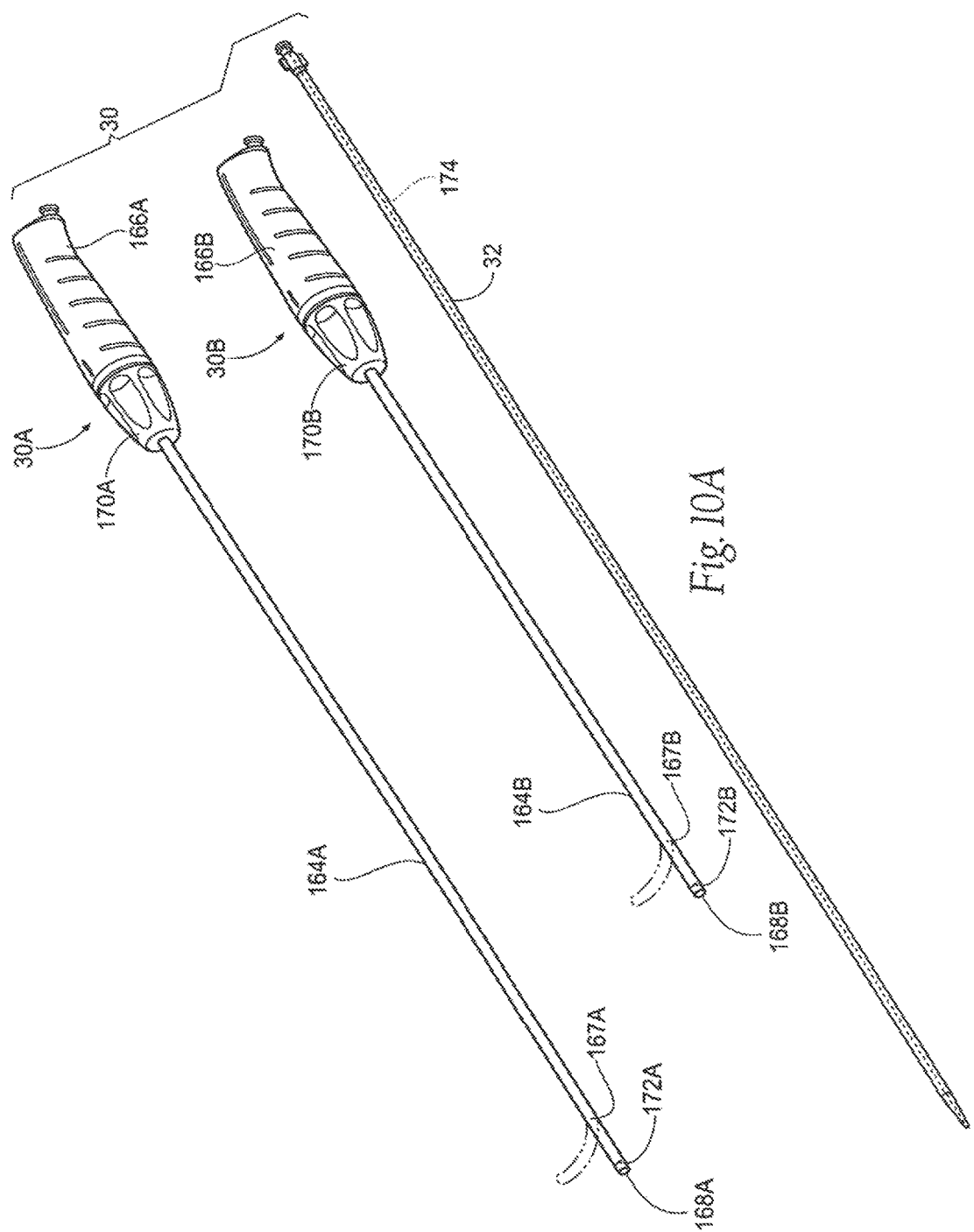
FIG. 10A is a perspective view of the first steerable endovascular guide, the second steerable endovascular guide, and the obturator, which make up a steerable endovascular guide system (a two segment guide system is shown) that form a part of the system shown in FIG. 4.

The endovascular stapling system 16 comprises a steerable endovascular guide system 30 comprising a first steerable guide 30A and a second steerable guide 30B, and a companion obturator 32 (see FIGS. 10A and 10B). The endovascular stapling system 16 also comprises a plurality of endovascular staples 36 (FIG. 11A) and, desirably, a cassette 34 for holding the staples 36 (see FIG. 11B), as well as an endovascular staple applier 38 (see FIGS. 12A and 12B). It is to be appreciated that the steerable endovascular guide system 30 may comprise a single guide device incorporating the features of the first steerable guide 30A and the second steerable guide 30B (see FIG. 10D).

The stapling system 16 may be used to apply an apposition force to the endovascular graft 12 to modify the shape of the endovascular graft to conform to the shape of the vessel wall. The endovascular stapling system 16 is also adapted to provide apposition force for improved sealing and fixation to eliminate movement and/or migration of the endovascular graft 12 within the vascular system. The endovascular stapling system 30 and endovascular staples 36 may also be used without the use of a graft 12 to close the entrance of a vessel dissection to blood flow.

a. Steerable Endovascular Guide and Companion Obturator

Referring to FIGS. 10A through 10D, the steerable endovascular guide system 30 is a single use system that is supplied with a companion obturator 32 to the user within its package 50 in a sterile condition. The steerable endovascular guide system 30 is sized and configured to direct the endovascular staple applier 38 through at least one or more resolved angles to the desired location in a vessel for implantation of one or more endovascular staples 36, i.e., through one or more steerable segments 167A and 167B. In one embodiment shown in FIGS. 10A and 10B, steerable segment 167A is a component of the first steerable guide 30A, and steerable segment 167B is a component of the second steerable guide 30B.

In an additional embodiment shown in FIG. 10D, steerable segment 167A and steerable segment 167B are both components of an integrated endovascular guide system 30.

The first (inner) steerable endovascular guide 30A includes a guide tube 164A, and a handle 166A coupled to the proximal end of the guide tube 164A. The guide tube 164A defines an open interior lumen 168A accommodating passage of the endovascular staple applier 38 (during use).

The second (outer) steerable endovascular guide 30B is similar to the first steerable guide 30A, except the second steerable guide tube 164B has a shorter overall length, as will be described below. The second steerable guide 30B includes a guide tube 164B, and a handle 166B coupled to the proximal end of the guide tube 164B. The guide tube 164B defines an open interior lumen 168B accommodating passage of the obturator 32 (during deployment) and the guide tube 164A of the first steerable endovascular guide segment 30A (during use).

The distal portion of the two segment steerable endovascular guide system 30 can be deflected in one or more distinct segments comprising the first steerable segment 167A and the second steerable segment 167B (as shown in phantom lines in FIGS. 10A and 10B), and re-straightened by deflection means, such as steering wires or pull cords (not shown) coupled to a first rotational deflector knob 170A on the handle 166A of the first steerable guide 30A for control of the first segment 167A, and a second deflector knob 170B on the handle 166B of the second steerable guide 30B for control of the second segment 167B. Each deflector knob 170A, 170B is adapted to move its respective steerable segment 167A, 167B, from a first, generally straight position for deployment to the general targeted region, to a second, articulated position for alignment of the distal end of the guide tube 164A, and the staple applier 38, to be in contact with the vessel wall for staple deployment.

In the two component configuration, the guide tube 164A of the first steerable endovascular guide 30A is inserted (i.e., nested) into the lumen 168B of the guide tube 164B of the second steerable guide 30B until the distal end of the handle 166A is positioned near or against the proximal end of the handle 166B. The length of the second guide tube 164B is less than the length of the first guide tube 164A (see FIG. 10B). This allows the distal end segment 167A to be independently articulated (via the rotational deflector knob 170A) as it may not be confined within the second guide tube 164B. In addition, the first steerable guide 30A may be selectively moved longitudinally relative to the second steerable guide 30B. Longitudinal adjustment of the first steerable guide 30A allows the length of the distal end segment 176A to be adjusted. Because the first guide tube 164A passes through and extends beyond the distal end of the second guide tube 164B, when the distal end segment 167B of the second guide tube 164B is articulated (via the rotational deflector knob 170B), the first guide tube 164A articulates with the second guide tube 164B. The nested guide tubes 164A and 164B allow for distal end segments 167A and 167B to be independently steerable and longitudinally adjustable to produce at least one resolved angle to aid in positioning the stapler applier 38 in a desired location to produce a force resolution desired to deploy a staple 36.

In a representative, embodiment, the over-all length of guide tube 164A, not including handle 166A, is preferably between 40 and 120 cm and most preferably between 60 and 110 cm, and the length of the two segment deflectable tip is preferably between 1.0 and 10 cm and most preferably between 2 and 5 cm. The first segment 167A is preferably between about 1.0 and 5.0 cm, and the second segment 167B is preferably between about 1.0 and 2-5 cm. It is to be appreciated that the lengths of the segments may change depending on the body lumen in which the endovascular guide system is being used. C-shaped radiopaque markers 172A and 172B may be located at or near the distal tip of the guide tube 164A and 164B respectively, to aid in orientation under fluoroscopy.

In yet an additional embodiment of a steerable endovascular guide shown in FIG. 10E, the steerable guide 30C may include a single control handle 166C with a single steerable guide tube 164C, as compared to the steerable guides shown in FIGS. 10B and 10D, where assemblies are combined to produce a steerable endovascular guide. The control handle 166C may be adapted for steering the guide tube 164C in multiple directions using, for example, a first deflector knob 170C and second deflector knob 170D. As can be seen, the single guide tube is shown with two steerable segments 167C and 167D.

In a representative embodiment, the obturator 32 is desirably sized and configured with a lumen 174 accommodating conventional over-the-wire delivery within a patient's vasculature, e.g., using an appropriately sized guide wire.

Further details of representative constructions of a steerable endovascular guide 30A can be found in co-pending, commonly owned U.S. patent application Ser. No. 11/254,619, filed Oct. 20, 2005, and entitled "Devices, Systems, and Methods for Guiding an Operative Tool into an Interior Body," and co-pending, commonly owned U.S. patent application Ser. No. 11/255,116, filed Oct. 20, 2005, and entitled "Devices, Systems, and Methods for Prosthesis Delivery and Implantation," which are both incorporated herein by reference.

b. The Endovascular Staple and Companion Cassette

The endovascular staple 36 (see FIG. 11A) is a single use component that is supplied, desirably in a companion cassette 34, to the user within a package in a sterile condition. The endovascular staple 36 is sized and configured to attach the endovascular graft 12 to a vessel wall, and/or to close the entrance of a vessel dissection.

In the illustrated embodiment (see FIG. 11A) the endovascular staple 36 comprises a main staple body 176 that is helical-shaped. The helical-shape allows the endovascular staple 36 to pierce and engage tissue in response to rotation of the main staple body 176, thereby securing attachment of the endovascular graft 12 to a vessel wall.

In a representative embodiment, the main staple body 176 is manufactured from medical grade wire having a diameter between about 0.1 mm and 1.0 mm. In a representative embodiment, the endovascular staple 36 is approximately between about 2 mm and 12 mm in over-all length and approximately between about 1.0 mm and 10 mm in maximum diameter. The leading end 178 of the main staple body 176 is desirably sharpened to facilitate atraumatic deployment through the graft materials and vessel wall. The proximal end 180 of the main staple body 176 is desirably closed to prevent over-penetration of the endovascular staple 36.

Desirably, a plurality of staples 36 (e.g., ten) are provided in a convenient cassette 34 (see FIG. 11B), to allow easy and accurate loading into the endovascular staple applier 38. The cassette 34 includes a base 208 having a plurality of foil covered spaced apart staple ports or stations 210, each sized to house a staple 36. A deformable cover 212 (e.g. a foil cover) may be positioned over each staple port 220, and may include a precut shape, such as an "X". The precut "X" allows access for the staple applier 38 to the staple 36 within the port 210, and when the staple applier is inserted the deformable cover 212 and associate "X" deform 213, providing a visual indication to the user which port has been accessed. In use, an operator identifies a port 210 having a precut "X" in the cover 212. The operator operates the staple applier 38 to load the staple 36 from the foil covered port 210, as will be described in greater detail below. After implanting the withdrawn staple 36, the operator again identifies a port 210 having a precut "X" in the cover 212. The operator again operates the staple applier 38 to load the staple 36 from the foil covered port 210 for implantation. In this way, the cassette 34 aids the operator in loading individual staples on the staple applier 36 for implantation in a single fire (one at a time) fashion.

Further details of representative constructions of an endovascular staple 36 and companion cassette 34 can be found in co-pending, commonly owned U.S. patent application Ser. No. 11/255,126, filed Oct. 20, 2005, and entitled "Devices, Systems, and Methods for Prosthesis Delivery and Implantation," which is incorporated herein by reference.

c. Endovascular Staple Applier (1) Overview

The endovascular staple applier 38 (see FIGS. 12A and 12B) is a single use component chat is supplied to the user within a package 48 in a sterile condition. In the illustrated embodiment, the endovascular staple applier 38, a supply of endovascular staples 36, and the staple cassette 34 are provided, for the sake of convenience, in a single package 48. The endovascular staple applier 38 is sized and configured to pass through the lumen 168A of the first steerable endovascular guide 30A guide tube 164A, which may be nested within the lumen 168B of the second steerable endovascular guide 30B guide tube 164B and to be selectively operated to implant one or more endovascular staples 36 through the graft (when used) and into the vessel wall.

In the illustrated embodiment, the endovascular staple applier 38 comprises an applier catheter 182 and a control handle 184 coupled to the proximal end of the applier catheter 182. The applier catheter 182 carries a rotationally driven member 186 at its distal end. A battery powered motor 188 enclosed within the handle 184 is coupled to the driven member 186, to selectively rotate the driven member 186 either in a forward (e.g., clockwise) direction and reverse (e.g., counterclockwise) direction. A control circuit 190 in the handle 184 is coupled to the motor 188 and to a forward control button 192 and a reverse control button 194 on the handle. The control circuit 190 governs operation of the motor 188 according to pre-programmed operating parameters in response to user commands received by manipulation of the buttons 192 and 194.

In use, an endovascular staple 36 is loaded into the driven member 186 from the cassette 34, e.g., by placing the distal end of the applier catheter 182 into an exposed staple port 210 in the cassette 34 and pressing the reverse control button 194 (see FIG. 12C). The now loaded endovascular staple applier catheter 182 is passed through the nested guide tubes 164A and 164B of the endovascular guide system 30, which has been manipulated beforehand to be at an intended implantation site for the endovascular staple 36 (see FIGS. 13A to 13C). To simplify FIGS. 13A to 13C, the delivery system 24 is not shown.

As can be seen in FIG. 13A, the nested guide tubes 164A and 164B are adapted to guide the staple applier catheter 182 through one or more steerable segments 167A and 167B to the desired location in a vessel for implantation of one or more endovascular staples 36. The steerable guide system 30 may be used to apply the desired resolution of force to the endovascular graft 12 to modify the shape or form of the endovascular graft to conform to the shape of the vessel wall. This resolution of force can be utilized to deflect a portion or portions of the endovascular graft against the vessel wall to implant a staple 36.

Figure 13B:
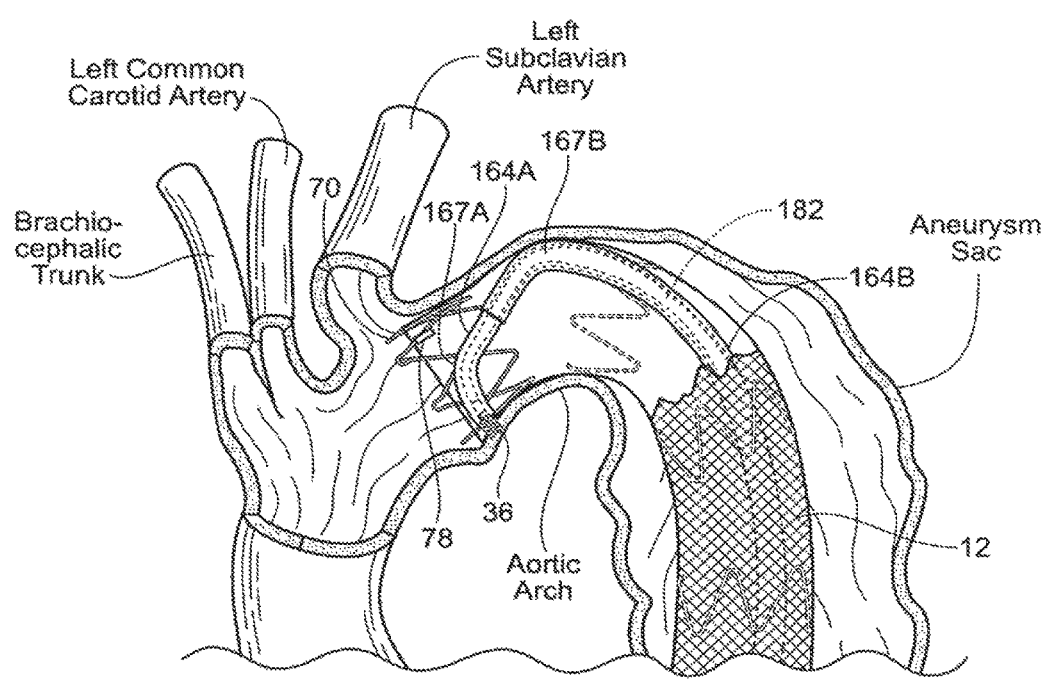
FIGS. 13B and 13C are anatomic views as shown in FIG. 13A, showing the fastener applier positioned within the two segment steerable guide system, the steerable guide system being used to apply an apposition force to the endovascular graft to deflect a portion of the graft against the vessel wall where the graft may not naturally lay flat, modifying the shape of the endovascular graft to conform to the vessel wall, and then implanting a fastener in the graft and adjacent tissue, to secure the position of the graft.
Figure 13C:
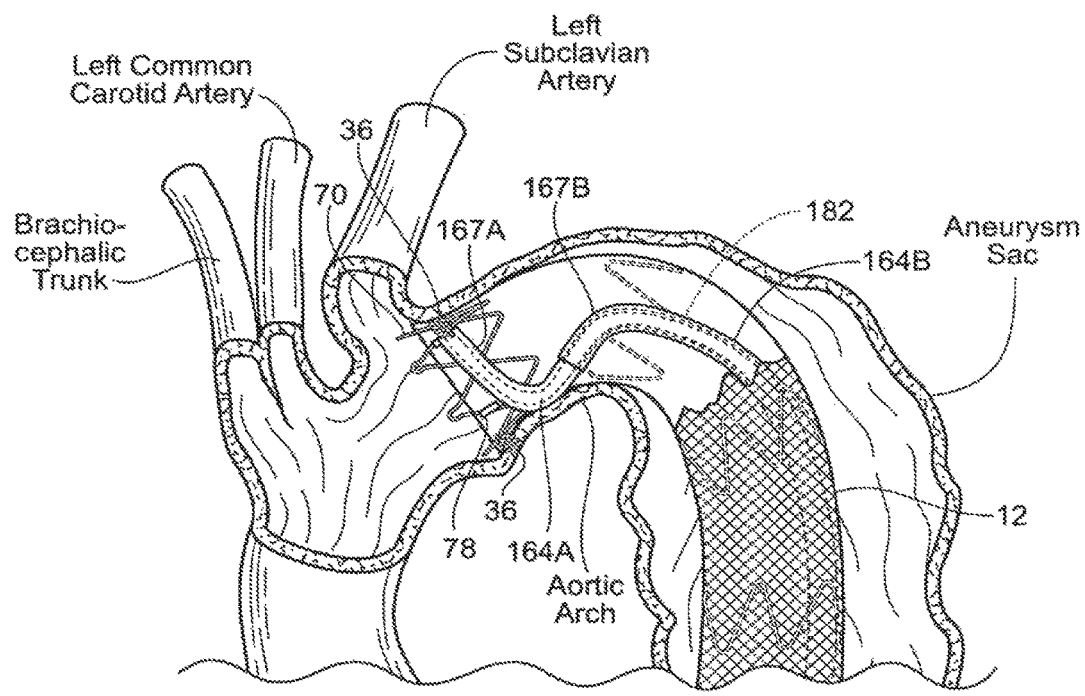

Once the endovascular staple applier catheter 182, loaded with a staple 36, is positioned at the desired location and the resolution of force is achieved, the physician presses the forward control button 192 to command rotation of the endovascular staple 36 in the forward direction, i.e., into tissue (see FIG. 13B).

The control circuit 190 is desirably pre-programmed to require a two-stage implantation process. The first stage commands only a partial implantation of the staple 36. In the first stage, the physician is allowed to ascertain whether the staple 36 is placed correctly at the desired location and that the desired located is suitable for implantation of the staple 36. While in the first stage, the physician is allowed to retract the staple 36 (by pressing the reverse control button 194) and to re-position the staple 36.

The control circuit 190 commands a full filial deployment of the staple 36 only after a deliberate entry of the second stage. In the first and second stages, the control circuit 190 generates audible tones and/or visual indicators (e.g., blinking lights) during operation of the motor 188, to indicate the position of the staple and available direction of motion.

Once the staple 36 is implanted, the endovascular staple applier 38 is withdrawn through the nested guide tubes 164A and 164B. The physician identifies another port 210 having a precut "X" in the cover 212. The staple applier 38 is reloaded. The two segment endovascular guide system 30 is manipulated to another desired implantation site, and the endovascular staple applier 38 (reloaded with another staple 36) is redeployed and operated in the manner just described (see FIG. 12C). The endovascular staple applier 38 is intended to be loaded, deployed, and reloaded in this way multiple times for a single patient.

Further details of representative constructions of an endovascular staple applier 38 and methods of its use can be found in co-pending, commonly owned U.S. patent application Ser. No. 11/254,950, filed Oct. 20, 2005, and entitled "Devices, Systems, and Methods for Prosthesis Delivery and Implantation, Including the Use of a Fastening Tool" which is incorporated herein by reference.

Figure 14A:
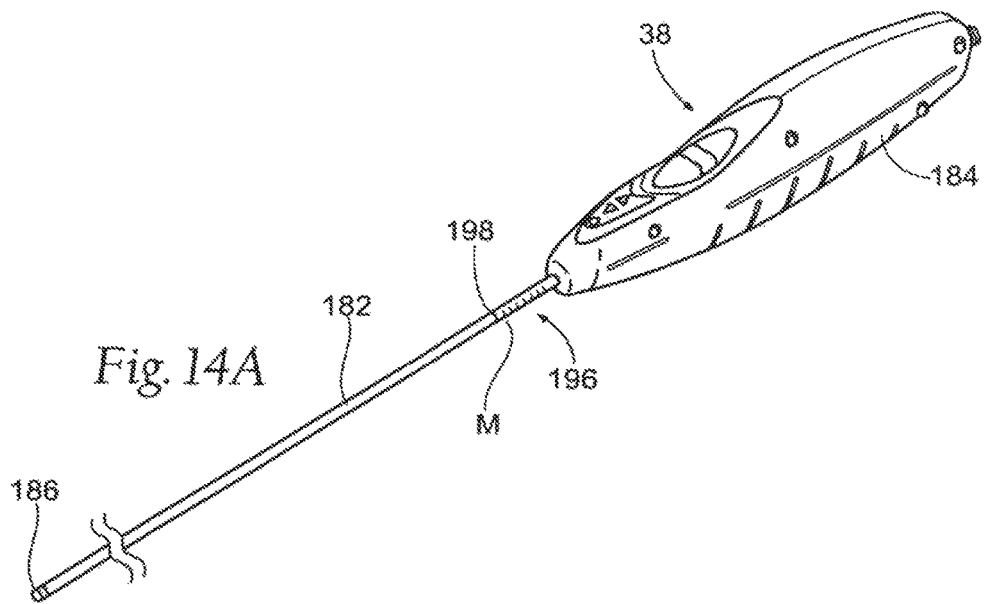
FIG. 14A is a view showing a fastener applier of a type shown in FIG. 12A, which includes indicia visible to a naked eye.

(2) Tracking the Relative Position of the Endovascular Staple Applier in the Endovascular Guide As seen in FIG. 14A, the endovascular staple applier 38 desirably includes indicia 196, which is visible to a naked eye (i.e., without resort to fluoroscopic visualization or other visualization techniques that augment human vision) that indicates the extent to which the driven distal end 186 of the applier catheter 182, which carries the endovascular staple 36, resides within the guide tube 164A of the first steerable endovascular guide 30A. In particular, the visible indicia 196 indicates when the driven distal end 186 of the applier catheter 182 and the staple 36 it carries have arrived at a predetermined location within the guide tube 164A near to the distal end of the guide tube 164A. In this way (see FIGS. 14B and 14C), the physician can quickly and accurately ascertain, without resort to fluoroscopic visualization, that the distal end 186 of the applier catheter 182, and the endovascular staple 36 it carries, are positioned adjacent the end of the guide tube 164A, ready for final deployment, once the guide tube 164A is placed at the intended implantation site. The visible indicia 196 can also indicate the extent to which the driven distal end 186 of the applier catheter 182 has been extended outside the distal end of the guide tube 164A.

In the illustrated embodiment (see FIG. 14A), the indicia 196 comprises visible material or markings M on the most proximal section of the applier catheter 182, adjacent the handle 184, that is marked or colored differently or is otherwise differentiated from the remainder of the applier catheter 182. In a representative example, a prescribed length of contrast-colored tubing 198 can be placed at the most proximal end of the applier catheter 182, where it exits the handle 184.

The contrast-color tubing 198 has a prescribed length. The distal end of the tubing 198 marks a line of differentiation between the tubing 198 and the remainder of the applier catheter 182. The length is selected so that the distal end of the tubing 198 registers with the insertion port/hemostatic seal 200 on the handle 166A of the first steerable endovascular guide 30A (see FIG. 14B) when the driven distal end 186 of applier catheter 182 rests at a desired inset distance d within the distal end of the guide tube 164A (see FIG. 14C).

In this way, the indicia 196 indicates when the applier catheter 182 has reached a desired location relative to the end of the guide tube 164A, and is ready to be further advanced to implant the endovascular staple 36. The contrast-color tubing 198 may further include additional markings M along its length by which the physician can gauge advancement of the applier catheter 182 beyond the guide tube 164A.

The indicia 196 makes it possible for the physician, without resort to fluoroscopic visualization, to always know the position of the endovascular staple 36 and staple applier 182 relative to the end of the endovascular guide system 30 (e.g., within or outside the guide tube 264A.

(3) The Motor Control Circuit

Figure 15A:
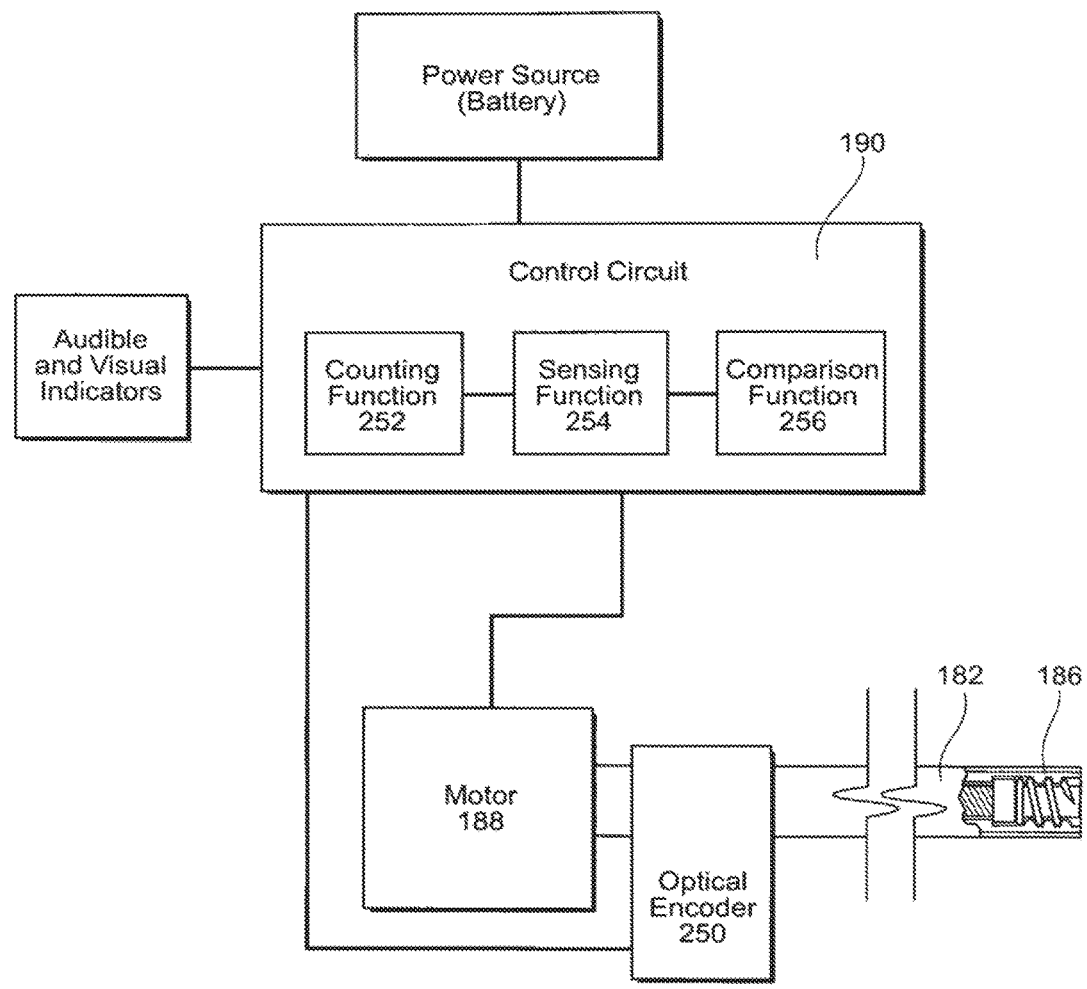
FIG. 15A is a schematic view of the motor control functions of a representative control circuit for the fastener applier shown in FIG. 12A.
Figure 15B:
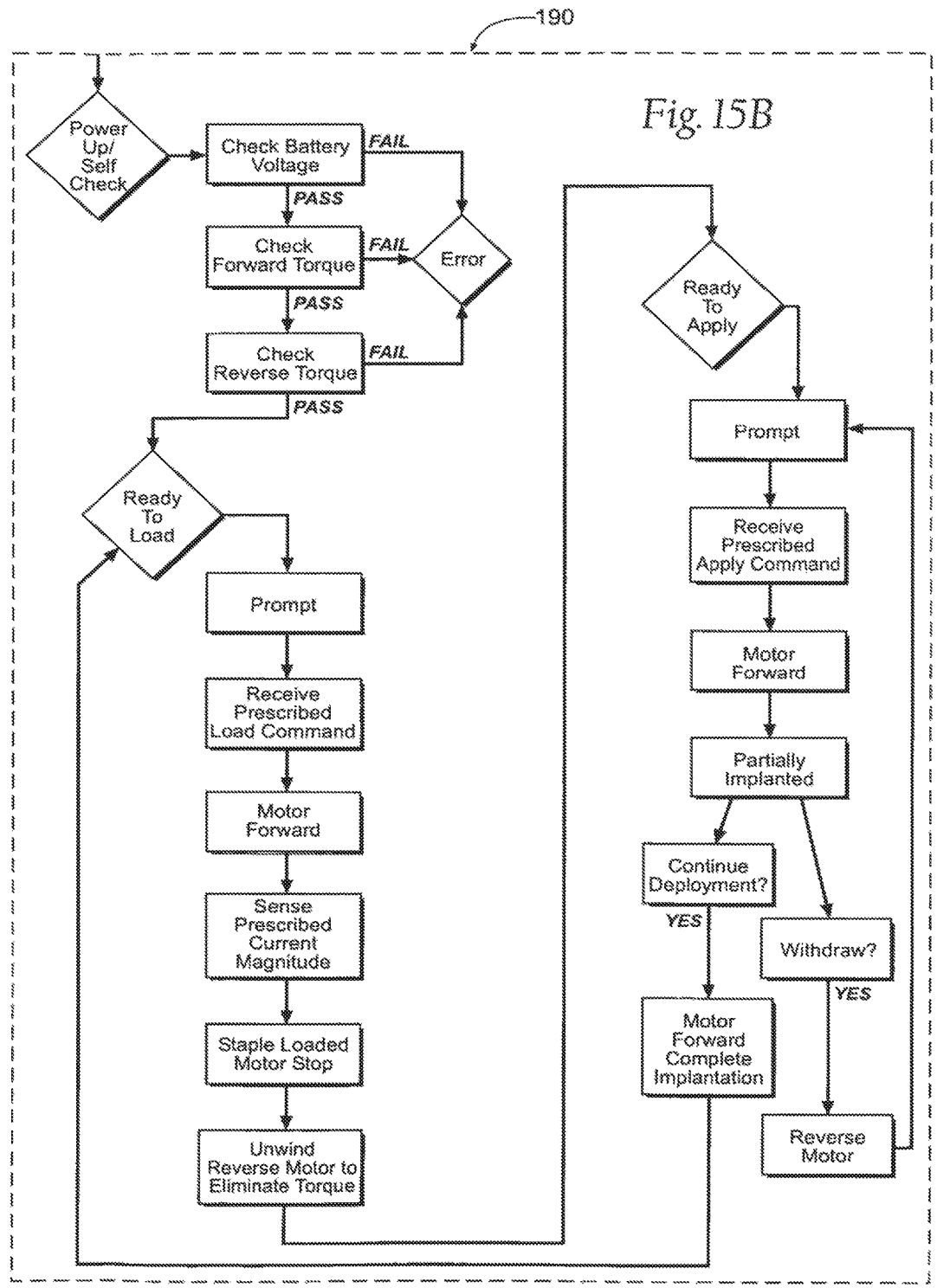
FIG. 15B is a schematic flow diagram of the operational states of the control circuit shown in FIG. 15A.

In a representative embodiment (see FIGS. 15A and 15B), the control circuit 190 for the motor includes an optical encoder 250 coupled to a counting function 252, to enable counting the revolutions of the battery powered motor 188. The control circuit 190 also includes a sensing function 254 that senses the magnitude of current being drawn by the motor 188, for deriving torque that the motor 188 is encountering. The control circuit 190 also includes a comparison function 256 that compares the magnitude of the sensed torque (current) with set torque limits in either the forward or reverse direction, to change the state of operation should excess torque conditions be encountered.

The control circuit 190 carries embedded code, which expresses pre-programmed rules or algorithms under which different operation states are entered and motor command signals are generated in response to input from the external control sources and the counting, sensing, and comparison functions. The pre-programmed rules or algorithms of the control circuit 190 are designed to conserve power consumption, placing the circuit into a standby (wait) mode between staple loading and deployment cycles. This makes it possible to power up the staple applier just once and to leave the staple applier on during an entire procedure, avoiding time consumed in repeated power ups and power downs. The pre-programmed rules or algorithms of the control circuit also dictate that a desired sequence of steps is faithfully followed in loading, deploying, and reloading the staples, prompting the physician at the initiation of each step and not allowing any short-cuts or deviations along the way.

Further details of representative constructions of an endovascular staple applier 38 and methods of its use, including features of the pre-programmed rules or algorithms of a representative control circuit 190, can be found in co-pending, commonly owned U.S. patent application Ser. No. 11/254,950, filed Oct. 20, 2005, and entitled "Devices, Systems, and Methods for Prosthesis Delivery and Implantation, Including the Use of a Fastening Tool" and co-pending, commonly owned U.S. patent application Ser. No. 11/488,305, filed Jul. 18, 2006, and entitled "Endovascular Aneurysm Devices, Systems, and Methods", which are both incorporated herein by reference.

C. The Instructions for Use, Including Deploying an Endovascular Graft

The instructions for use 58 can direct use of catheter-based technology via a peripheral intravascular access site, such as in the femoral artery, optionally with the assistance of image guidance, image guidance includes but is not limited to fluoroscopy, ultrasound, magnetic resonance, computed tomography, or combinations thereof. The instructions for use may include instructions for implanting an endovascular graft 12 to repair an aortic aneurysm, for example. The instructions for use may also include instructions for implanting endovascular staples 36 without the use of a graft 12, for the repair of an aortic dissection, for example, as will be described below.

FIGS. 16A through 18B show representative embodiments of the steps chat representative instructions for use 58 can incorporate or direct.

In a representative embodiment, the instructions for use 58 may include the achievement of percutaneous vascular access by conventional methods into the femoral artery, for example. In this arrangement, the patient is placed on an imaging table, allowing fluoroscopic visualization from the aortic arch to the femoral artery bifurcations. Access is secured to one or both contralateral and ipsilateral branches by standard techniques using introducer sheaths (which can be supplied as part of the kit 40). Using fluoroscopic guidance, access to the patient's aortic arch can be achieved with an appropriately sized guide wire through one or both femoral access sites.

1. Position the Endovascular Graft in the Targeted Endovascular Treatment Site

In this arrangement, the instructions 58 for use may include positioning of the endovascular graft 12 to be deployed. An unsupported graft, and a delivery system 24 including stabilizing arms 106 are shown. It is to be appreciated that other configurations of grafts 12, and delivery systems 24, i.e., without stabilization arms, both as previously described, may be used and are intended to be included in the scope of the invention. It is also to be appreciated that at anytime during or after the retraction of the graft retention jacket, the entire graft assembly may be repositioned within the vasculature. The instructions may include a series of steps that can be followed to carry out this portion of the procedure. These steps may include, but are not limited to:

(i) after flushing the delivery system 24 with heparinized saline, positioning the delivery system 24 within an aortic abnormality over the guide wire via a femoral access site, which has been previously established in conventional fashion (FIG. 16A);

(ii) visualizing the proper position and orientation of the endovascular graft 12 using the radiopaque markers (e.g., proximal stent markers 78, distal stent markers 80 and the marker(s) 120 positioned at or near the leading edge of the graft retention jacket 102;)

(iii) withdrawing the graft retention jacket 102 of the delivery system 24 by rotating the jacket retraction knob 124 and/or sliding the jacket retraction slide 126 away from the patient. Alternatively, the mechanical advantage mechanism may be terminated by the physician at any point during the jacket retraction. The instructions may note that the proximal portion 65 of the endovascular graft 12 will not open during retraction of the jacket 102 and that the proximal portion 65 and distal portion 66 of the graft remain collapsed and connected to the delivery system 24, and chat at anytime during or after the retraction of the jacket retention jacket the entire graft assembly may be repositioned within the vasculature (FIG. 16B);

(iv) verifying the position and orientation of the endovascular graft 12 using the radiopaque markers (e.g., 78, 80, and 120,); and opening the distal portion 66 by retracting the distal release slide 118. Alternatively, the distal portion 66 may open on its own, without the need to operate any controls.

(v) releasing the endovascular graft proximal portion 65 from the delivery system by retracting the proximal end release slide 114 on the handle away from the patient (FIG. 16C). When a delivery system 24 incorporating stabilizing arms 106 or other release wires are used, the instructions may note that the proximal portion (or other portions) of the endovascular graft 12 way still remain secured to the delivery system 24. The physician thereby maintains control and can manipulate the position and orientation of the graft assembly 12 during deployment of endovascular staples.

The instructions may also note that the use of release wires in place of stabilizing arms 106 may be used to attach the endovascular graft 12 to the inner assembly 100 to maintain control of the graft 12 while implantation of endovascular staples takes place.

With an alternative embodiment of a delivery system 24 without stabilizing arms, as previously described, after the proximal portion 65 and distal portion 66 are released from the delivery system, the graft 12 is free of the delivery system 24 and remains in position with the radial force of the proximal stent 70 and/or additional stents incorporated with the graft 12. It is to be appreciated that any of the delivery systems described herein may be removed at this stage of the procedure, or may be removed after endovascular staples have been deployed, as described below.

2. Deploy Endovascular Staples to Secure the Position of the Endovascular Graft

The instructions for use 58 may next instruct securing of the position of the proximal portion of the endovascular graft 12 using endovascular staples 36. The instructions may include a series of steps that can be followed to carry out this portico of the procedure. These steps may include, but are not limited to:

(i) placing an appropriate length and sized guide wire via the femoral access site into the aortic arch. The endovascular graft 12 includes distal end radiopaque markers 80 that outline the opening of the distal portion 66 of the endovascular graft 12. The guide wire is to be placed through this opening and its position verified using standard endovascular techniques;

(ii) using fluoroscopic guidance, advancing the second steerable endovascular guide 30B with the obturator 32 over the guide wire into a position within the proximal neck of the thoracic aneurism (FIG. 16D). The C-shaped radiopaque marker 172B located at the distal tip of the guide tube 164B will aid in fluoroscopic visualization. Position the steerable endovascular guide system 30 at the desired location for endovascular staple implantation within a desired location on the endovascular graft 12, (e.g., between the marker bands 78 on the proximal stent 70 and the bottom edge of the proximal stent 70.) In addition, the steerable endovascular guide system 30 may be used to contact and apply an apposition force to deflect a portion or portions of the proximal portion, or other portions of, the graft 12 and/or the stent 70 against the vessel wall to conform the shape of the endovascular graft 12 to the vessel wall at the desired location;

(iii) removing the guide wire and obturator 32 to open the lumen 168B of the second steerable endovascular guide 30B and inserting the guide tube 164A of the first steerable endovascular guide 30A into the lumen 168B. (Alternatively, the first steerable endovascular guide 30A and the second steerable endovascular guide 30B may be inserted at the same time with only one obturator in the lumen 168B of the second steerable endovascular guide 30B.)

(iv) deflecting the distal segments 167A and/or 167B of the two segment steerable endovascular guide system 30 toward the first intended staple implantation area by rotating the first and/or second deflector knobs 170A, 170B to achieve one or more bends or angles, while observing with fluoroscopic guidance. The instructions may note that the C-shaped fluoroscopic markers 172A and 172B will appear as a straight line when their respective catheters are oriented laterally, as a right curve "(" when oriented anteriorly, and as a left curve ")" when oriented posteriorly. Alternatively, the manipulation of the guide system (deflecting the distal segments) can be performed after the insertion of the endovascular staple applier;

(v) turning on the endovascular staple applier 38 by pressing one or more of the control buttons 194, 192 for a predetermined amount of time. This can initiate a self-checking sequence with audible end/or visual indicators. At the end of this sequence, the reverse indicator 202 will indicate that the endovascular staple applier 38 is ready to load the first endovascular staple 36. The instructions way note that, if at the end of the self check sequence, the error light 204 is illuminated, the endovascular staple applier 38 has encountered an error. The error can be cleared by pressing one or more of the control buttons 194,192 for a predetermined amount of time. After the error has been cleared, the self check sequence will initiate. If the error light 202 can not be cleared the endovascular staple applier 38 is not functional and should not be used;

(vi) load the staple by pressing the reverse command button 194 on the handle. While the motor 188 is running, insert the distal end of the endovascular staple applier catheter 182 into a port 210 having a precut "X" in the cover 212 of the cassette 34. The reverse indicator 202 will illuminate, and the endovascular staple will be drawn from the cassette into the distal end of the staple applier 38. When the endovascular staple 36 is loaded, an audible tone (e.g., two short beeps) will be heard, and the forward indicator 206 will illuminate. This indicates that the endovascular staple 36 is now preloaded in the staple applier 38, and the applier 38 can be removed from the cassette 34. The precut "X" in the cover 212 deforms with the insertion of the staple applier 38. The instructions may urge the physician to verify that the endovascular staple 36 is in place by visually inspecting the distal tip of the applier 38;

(vii) while stabilizing the control handle 160C or handles 166A and 166B of the endovascular guide system 30 relative to the patient, inserting the now-loaded endovascular staple applier 33 through the hemostatic seal at the proximal end of the first steerable endovascular guide control handle 166A. The instructions may direct the physician to observe the location of the visible contrast-color tubing 198 or other indicia on the proximal end of the applier catheter 182 and to halt further insertion of the staple applier 38 when the end of the contrast-color tubing 398 registers with the insertion port/hemostatic seal on the handle of the steerable endovascular guide (as shown in FIG. 14B). This indicates that the distal end of applier catheter 182 rests a desired distance from the distal end of the guide tube 164 (as shown in FIG. 14C);

(viii) under fluoroscopic guidance, advancing the endovascular staple applier 38 through the steerable endovascular guide system 30 until the endovascular staple applier 38 emerges from the distal end of the endovascular guide system 30 and contacts the endovascular graft 12. Continue to advance the endovascular staple applier 38 until resistance is felt and/or visual indication of apposition can be seen using fluoroscopy. This indicates that the endovascular staple applier 38 is in apposition against the endovascular graft 12 and against the vessel wall at the desired location for staple deployment, and that the nested first and second steerable endovascular guide tubes 164A and 164B are fully or partially resolving the generally opposite apposition force. This resolution of force can be applied with either the staple applier 38 or endovascular guide system 30 alone, or in combination to deflect a portion or portions of the proximal portion, or other portions of the graft 12 and/or stent 70 against the vessel wall to conform the shape of the endovascular graft 12 to the vessel wall at the desired location.

(ix) using the control handle 164 of the endovascular staple applier 38, pressing the forward control button 192 for achieving the first stage of endovascular staple deployment. The endovascular staple will partially deploy and pause. An audible tone may be heard (e.g., four beeps) and the forward and reverse indicator 202 and 206 will illuminate (e.g., alternatively blink), indicating that the operator may continue deployment or withdraw the endovascular staple 36 back into the applier 38. The instructions may note that, in the event of a power loss when the staple 36 is partially deployed, the staple may be removed manually, for example, by manually rotating the handle 184 and catheter 182 in a counter-clockwise direction until the staple 36 disengages from the graft and tissue. The staple applier 38 can be removed from the endovascular guide 30 in this condition;

(x) if the endovascular staple 36 is not in the desired location, pressing the reverse control button 194 re-houses the staple 36 inside the staple applier 38 for re-positioning;

(xi) if the endovascular staple 36 is in the desired position, completing the final stage of staple deployment by pressing the forward control button 192 to implant the endovascular staple 36 through the graft materials and into the vessel wall (FIG. 16E). When complete, an audible tone (e.g., three beeps) is heard and the reverse indicator 202 will illuminate; FIG. 16F shows an alternative configuration of the final stage of staple deployment, similar to FIG. 16E, except that an alternative deployment system 24 without stabilizing arms has been previously removed prior to the deployment of endovascular staples 36.

Figure 16G:
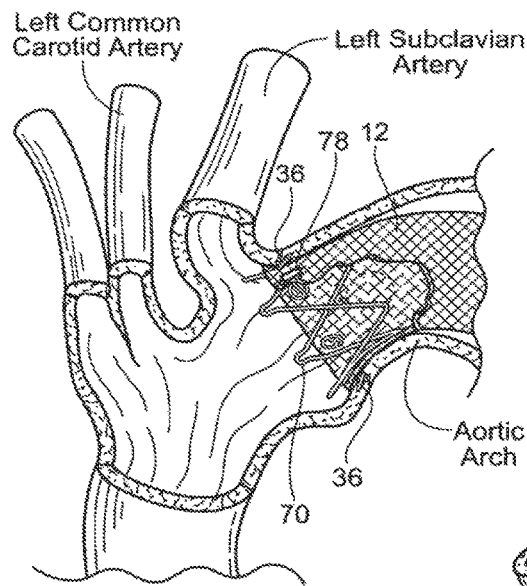
Figure 16H:
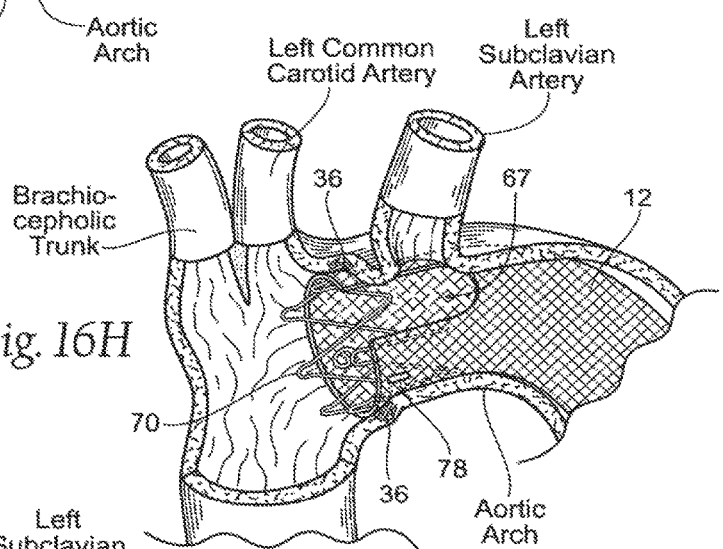
Figure 16I:
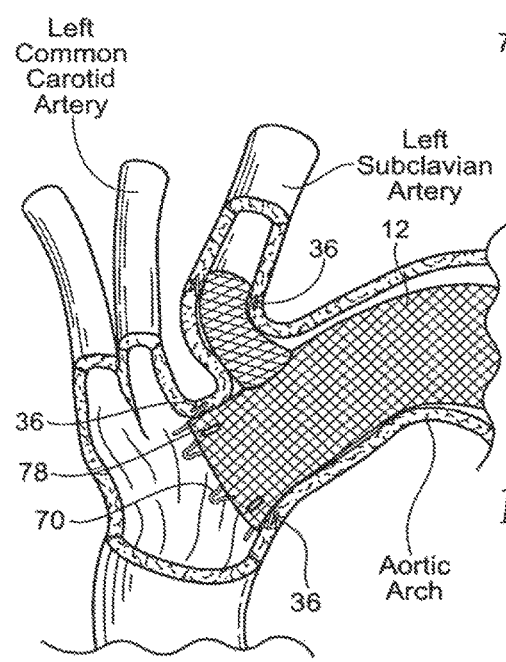

(xii) remove the endovascular staple applier 38, leaving the steerable endovascular guide system 30 in place;

(xiii) as needed, the steerable endovascular guide and/or the staple applier can be flushed with heparinized saline to prevent clotting in the lumens;

(xiv) identifying a port 210 having a precut "X" in the cover 212 to locate the next available endovascular staple port. Load the next endovascular staple in the manner described above;

(xv) repositioning the steerable endovascular guide system 30 to the next desired implantation site for an endovascular staple 36. Desirably, the physician straightens the first segment 167A and second segment 167B of the steerable endovascular guide system 30 between rotating in within the endovascular graft 12, to prevent accidental dislodgment or movement of the graft assembly 12;

(xvi) deploying the next endovascular staple 36 through the steerable endovascular guide 30 in the manner described above. Typically, 4 to 6 endovascular staples, evenly distributed about the circumference of the endovascular graft 12, will serve to secure the position of the graft 12 within the vessel (see FIG. 16G). FIG. 16H shows an alternative placement of the endovascular graft 12. As can be seen, the endovascular graft 12 incorporates an open graft portion 67 and is positioned more proximal within the aortic arch, proximal to the left subclavian artery. This position—proximal to the left subclavian artery—may be necessary in anatomies where the diseased tissue is so extensive that there is insufficient healthy tissue distal to the left subclavian artery to provide a sufficient landing zone for one or more staples 36. In prior systems where there was insufficient healthy tissue distal to the left subclavian artery necessary to provide a sufficient landing zone for barbs or hooks, the left subclavian artery was sacrificed, and then grafted to the left common carotid artery. The present systems and methods overcome this problem with the use of the open graft section 12 that maintains a fluid flow communication path to the left subclavian artery, and the ability to secure and seal the endovascular graft 12 in this tortuous location.

(xii) after deployment of the last endovascular staple, removing the endovascular stapler applier 38 from the steerable endovascular guide system 30;

(xiii) removing the steerable endovascular guide system 30 by first re-advancing the obturator 32 and guide wire (if appropriate) into the steerable endovascular guide system 30.

3. Complete the Endovascular Graft Deployment

The instructions for use 58 may next include the completion of the deployment of the endovascular graft 12, which may (or may not) remain in a secured but partially deployed condition during the deployment of the endovascular staples, as above described. The instructions may include a series of steps that can be followed to carry out this portion of the procedure. These steps may include, but are not limited to:

(i) moving to the femoral access site, where the delivery system 24 resides.

(ii) releasing the stabilizing arms 106 or other release wires from the graft by retracting the graft release slide 116 on the handle of the delivery system away from the patient. The endovascular graft 12 is now fully released (FIG. 16J);

(iii) rejacketing the delivery system 24 by holding the jacket retention slide 126 and slowly retract the delivery system 24, until the nosecone seals into the proximal end of the jacket 102;

(iv) remove the delivery system 24 from the patient, leaving the guide wire and femoral access introducer sheath in place if appropriate.

4. Completion of the Procedure

The instructions for use 58 may next include the completion of the procedure. The instructions may include a series of steps that can be followed to carry out this portion of the procedure. These steps may include, but are not limited to:

(i) performing post-implant aortic angiography to evaluate the implantation;

(ii) checking for endovascular leaks around the endovascular graft 12. If a leak is observed, standard endovascular techniques can be used to resolve. Additional staples may be placed, in the manner described above;

(iii) checking for proper location, blood flow, and patency of the endovascular graft 12;

(iv) removing the guide wires and femoral access sheaths and close the femoral arteriotomies according to standard practice to complete the procedure (FIG. 16K).

It is to be appreciated that the general steps just described do not necessarily need to follow the order in which they were described. It is also to be appreciated that fasteners may be applied to the distal region 66 of the endovascular graft 12 as well (as can be seen in FIG. 16K).

D. The Instructions for Use, Without Deploying an endovascular Craft

Figure 17A:
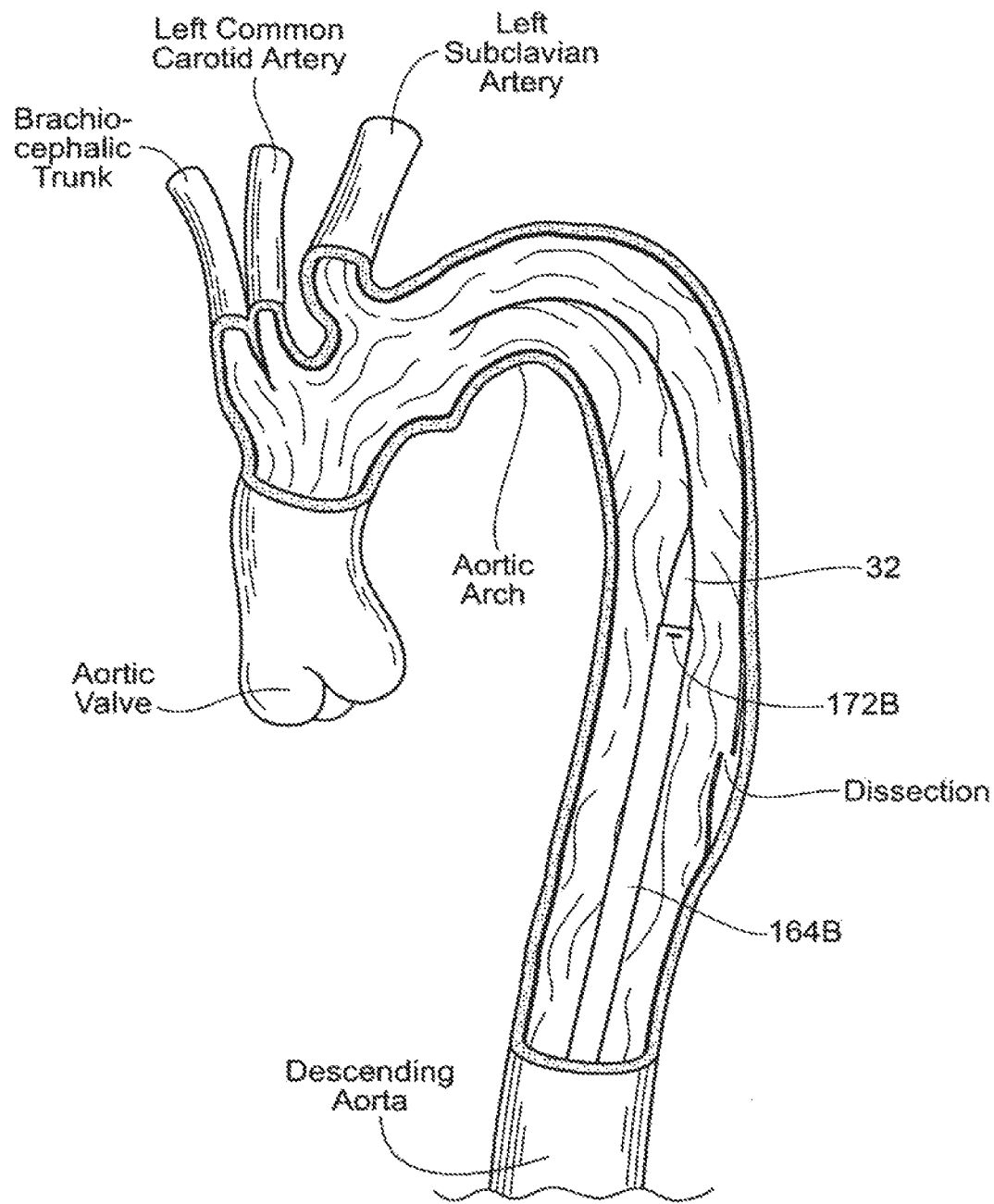
FIGS. 17A to 17C are anatomic views of manipulation of components or the system shown in FIG. 4 in repairing an aortic dissection in the descending thoracic aorta using staples and without a graft, which manipulations can be incorporated within an instruction for use associated with a kit of components like that shown in FIG. 5.
Figure 17B:
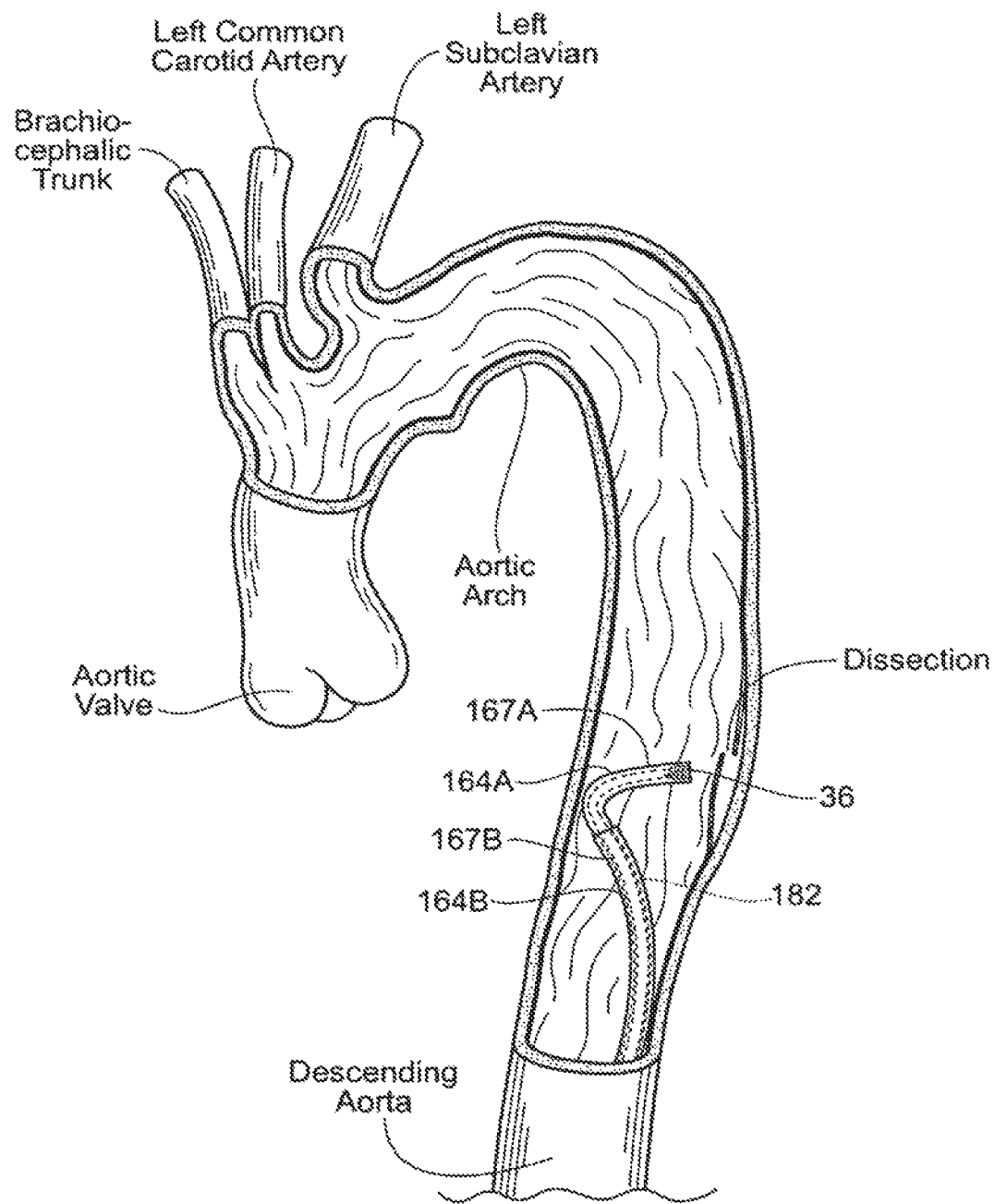
Figure 17C:
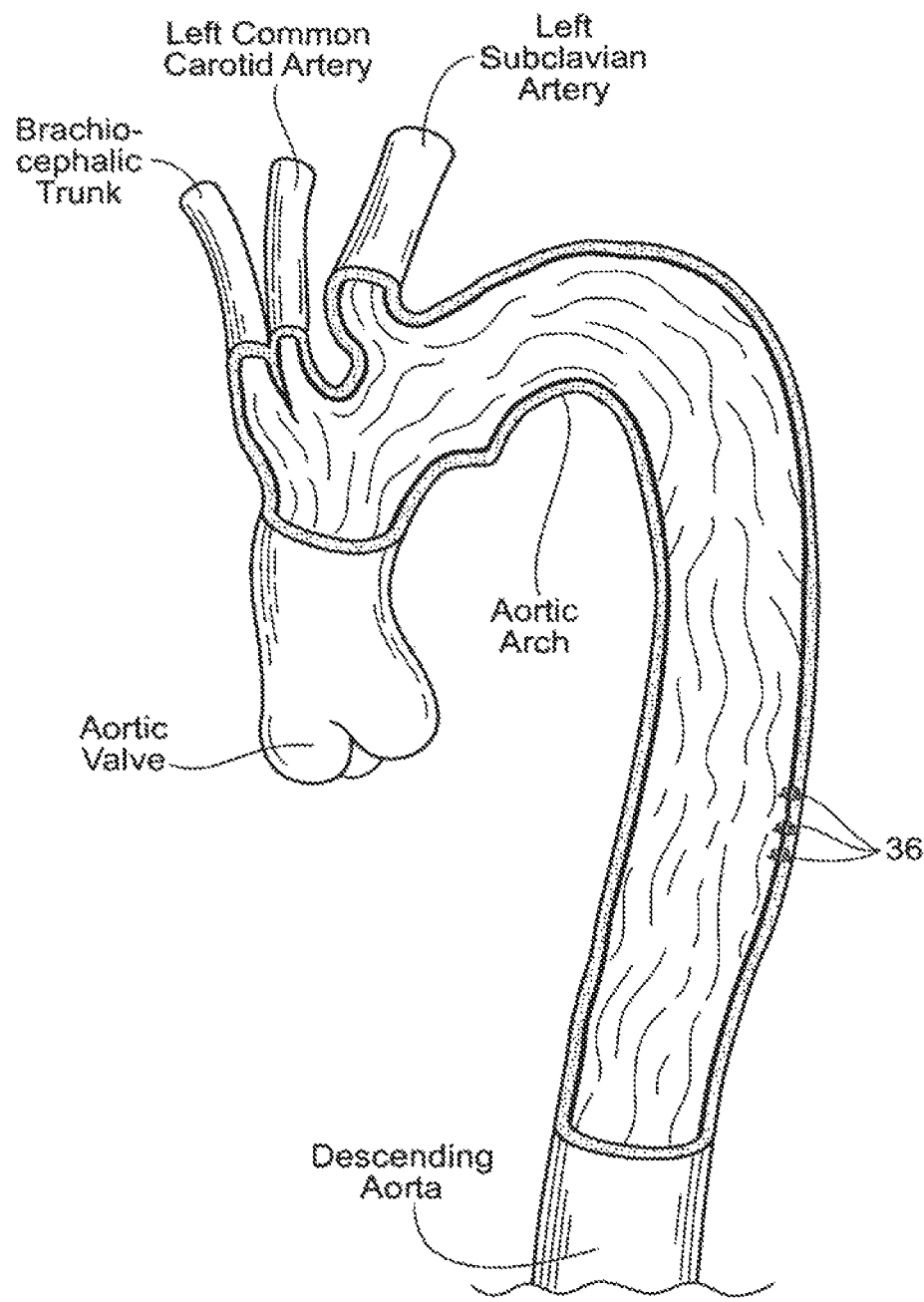

FIGS. 17A through 17C show a representative embodiment of the steps that a representative instructions for use 58 can incorporate or direct, without deploying an endovascular graft 12.

1. Deploy Endovascular Staples to Close an Aortic Dissection

In a representative embodiment, the instructions for use 58 may include the achievement of percutaneous vascular access by conventional methods into the femoral artery, for example. In this arrangement, the patient is placed on an imaging table, allowing fluoroscopic visualization from the aortic arch to the femoral artery bifurcations. Access may be secured to one or both contralateral and ipsilateral branches by standard techniques using introducer sheaths (which can be supplied as part of the kit 40). Using fluoroscopic guidance, access to the patient's aortic arch can be achieved with an appropriately sized guide wire through one or both femoral access sites.

These steps may include, but are not limited to:

(i) placing an appropriate length and sized guide wire via the femoral access site into the aortic arch.

(ii) using fluoroscopic guidance, advancing the second steerable endovascular guide 30B with the obturator 32 over the guide wire into a position at or near the tear in the aortic wall (FIG. 17A). The C-shaped radiopaque marker 172B located at the distal tip of the guide tube 164B will aid in fluoroscopic visualization. Position the steerable endovascular guide system 30 at the desired location for endovascular staple implantation within a desired stapling zone on the aortic dissection. In addition, the steerable endovascular guide system 30 may be used to contact the vessel wall and apply an apposition force desired for staple deployment. The instructions may note that the endovascular staples should be evenly distributed around the tear of the vessel wall in order to close the entrance of the dissection to blood flow;

(iii) removing the guide wire and obturator 32 to open the lumen 168B of the second steerable endovascular guide 30B and inserting the guide tube 164A of the first steerable endovascular guide 30A into the lumen 168B. (Alternatively, the first steerable endovascular guide 30A and the second steerable endovascular guide 30B may be inserted at the same time with only one obturator in the lumen 168B of the second steerable endovascular guide 30B.)

(iv) deflecting the distal segments 167A and/or 167B of the two segment steerable endovascular guide system 30 toward the first intended staple implantation area by rotating the first and/or second deflector knobs 170A, 170B to achieve one or more bends or angles, while observing with fluoroscopic guidance. The instructions may note that the C-shaped fluoroscopic markers 172A and 172B will appear as a straight line when their respective catheters are oriented laterally, as a right curve "(" when oriented anteriorly, and as a left curve ")" when oriented posteriorly. Alternatively, the manipulation of the guide system (deflecting the distal segments) can be performed after the insertion of the endovascular staple applier;

(v) turning on the endovascular staple applier 38 by pressing one or more of the control buttons 194, 192 for a predetermined amount of time. This can initiate a self-checking sequence with audible and/or visual indicators. At the end of this sequence, the reverse indicator 202 will indicate that the endovascular staple applier 38 is ready to load the first endovascular staple 36. The instructions may note that, if at the end of the self check sequence, the error light 204 is illuminated, the endovascular staple applier 38 has encountered an error. The error can be cleared by pressing one or more of the control buttons 194,192 for a predetermined amount of time. After the error has been cleared, the self check sequence will initiate. If the error light 202 can not be cleared the endovascular staple applier 38 is not functional and should not be used;

(vi) load the staple by pressing the reverse command button 194 on the handle. While the motor 188 is running, insert the distal end of the endovascular staple applier catheter 182 into a port 210 having a precut "X" in the cover 212 of the cassette 34. The reverse indicator 202 will illuminate, and the endovascular staple will be drawn from the cassette into the distal end of the staple applier 38. When the endovascular staple 36 is loaded, an audible tone (e.g., two short beeps) will be heard, and the forward indicator 206 will illuminate. This indicates that the endovascular staple 36 is now preloaded in the staple applier 38, and the applier 38 can be removed from the cassette 34. The precut "X" in the cover 212 deforms with the insertion of the staple applier 38. The instructions may urge the physician to verify that the endovascular staple 36 is in place by visually inspecting the distal tip of the applier 38;

(vii) while stabilizing the control handle 160C or handles 166A and 166B of the endovascular guide system 30 relative to the patient, inserting the now-loaded endovascular staple applier 38 through the hemostatic seal at the proximal end of the first steerable endovascular guide control handle 166A. The instructions may direct the physician to observe the location of the visible contrast-color tubing 198 or other indicia on the proximal end of the applier catheter 182 and to halt further Insertion of the staple applier 38 when the end of the contrast-color tubing 198 registers with the insertion port/hemostatic seal on the handle of the steerable endovascular guide (as shown in FIG. 14B). This indicates that the distal end of applier catheter 182 rests a desired distance from the distal end of the guide tube 164 (as shown in FIG. 14C);

(viii) under fluoroscopic guidance, advancing the endovascular staple applier 38 through the steerable endovascular guide system 30 until the endovascular staple applier 38 emerges from the distal end of the endovascular guide system 30 and contacts the torn vessel wall. Slowly, continue to advance the endovascular staple applier 38 until resistance is felt, and/or visual indication of apposition can be seen using fluoroscopy. This indicates that the endovascular staple applier 38 is firmly pushing against the vessel wall at the desired location for staple deployment, and that the nested first and second steerable endovascular guide tubes 164A and 164B are firmly pushing against the generally opposite vessel wall and applying the apposition force desired for staple deployment. This resolution of force can be applied with either the staple applier 38 or endovascular guide system 30 alone, or in combination to deflect a portion or portions of the vessel wall at the desired location.

(ix) using the control handle 184 of the endovascular staple applier 38, pressing the forward control button 192 for achieving the first stage of endovascular staple deployment. The endovascular staple will partially deploy and pause. An audible tone may be heard (e.g., four beeps) and the forward and reverse indicator 202 and 206 will illuminate (e.g., alternatively blink), indicating that the operator may continue deployment or withdraw the endovascular staple 36 back into the applier 38. The instructions may note that, in the event of a power loss when the staple 36 is partially deployed, the staple may be removed manually, for example, by manually rotating the handle 184 and catheter 182 in a counter-clockwise direction until the staple 36 disengages from the tissue. The staple applier 38 can be removed from the endovascular guide 30 in this condition;

(x) if the endovascular staple 36 is not in the desired location, pressing the reverse control button 194 re-houses the staple 36 inside the staple applier 38 for re-positioning;

(xi) if the endovascular staple 36 is in the desired position, completing the final stage of staple deployment by pressing the forward control button 192 to implant the endovascular staple 36 into the vessel wall (FIG. 17B). When complete, an audible tone (e.g., three beeps) is heard and the reverse indicator 202 will illuminate;

(xii) remove the endovascular staple applier 38, leaving the steerable endovascular guide system 30 in place;

(xiii) as needed, the steerable endovascular guide and/or the staple applier can be flushed with heparinized saline to prevent clotting in the lumens;

(xiv) identifying a port 210 having a precut "X" in the cover 212 to locate the next available endovascular staple port. Load the next endovascular staple in the manner described above;

(xv) repositioning the steerable endovascular guide system 30 to the next desired implantation site for an endovascular staple 36. Desirably, the physician straightens the first segment 167A and second segment 167B of the steerable endovascular guide system 30 between rotating in within the endovascular graft 12, to prevent accidental dislodgment of previously deployed staples or unnecessary contact with the vessel wall;

(xvi) deploying the next endovascular staple 36 through the steerable endovascular guide 30 in the manner described above;

(xvii) after deployment of the last endovascular staple, removing the endovascular stapler applier 38 from the steerable endovascular guide system 30;

(xviii) removing the steerable endovascular guide system 30 by first re-advancing the obturator 32 and guide wire (if appropriate) into the steerable endovascular guide system 30.

2. Completion of the Procedure

The instructions for use 38 may next include the completion of the procedure. The instructions may include a series of steps that can be followed to carry out this portion of the procedure. These steps may include, but are not limited to:

(i) performing post-implant aortic angiography to evaluate the staple(s) implantation;

(ii) checking for endovascular leaks around the tear in the vessel wall. If a leak is observed, standard endovascular techniques can be used to resolve. Additional staples may be placed, in the manner described above;

(iii) removing the guide wire and femoral access sheath and close the femoral arteriotomies according to standard practice to complete the procedure (FIG. 17C).

It is to be appreciated that the general steps just described do not necessarily need to follow the order in which they were described.

E. Alternative Graft Configurations

Figure 18A:
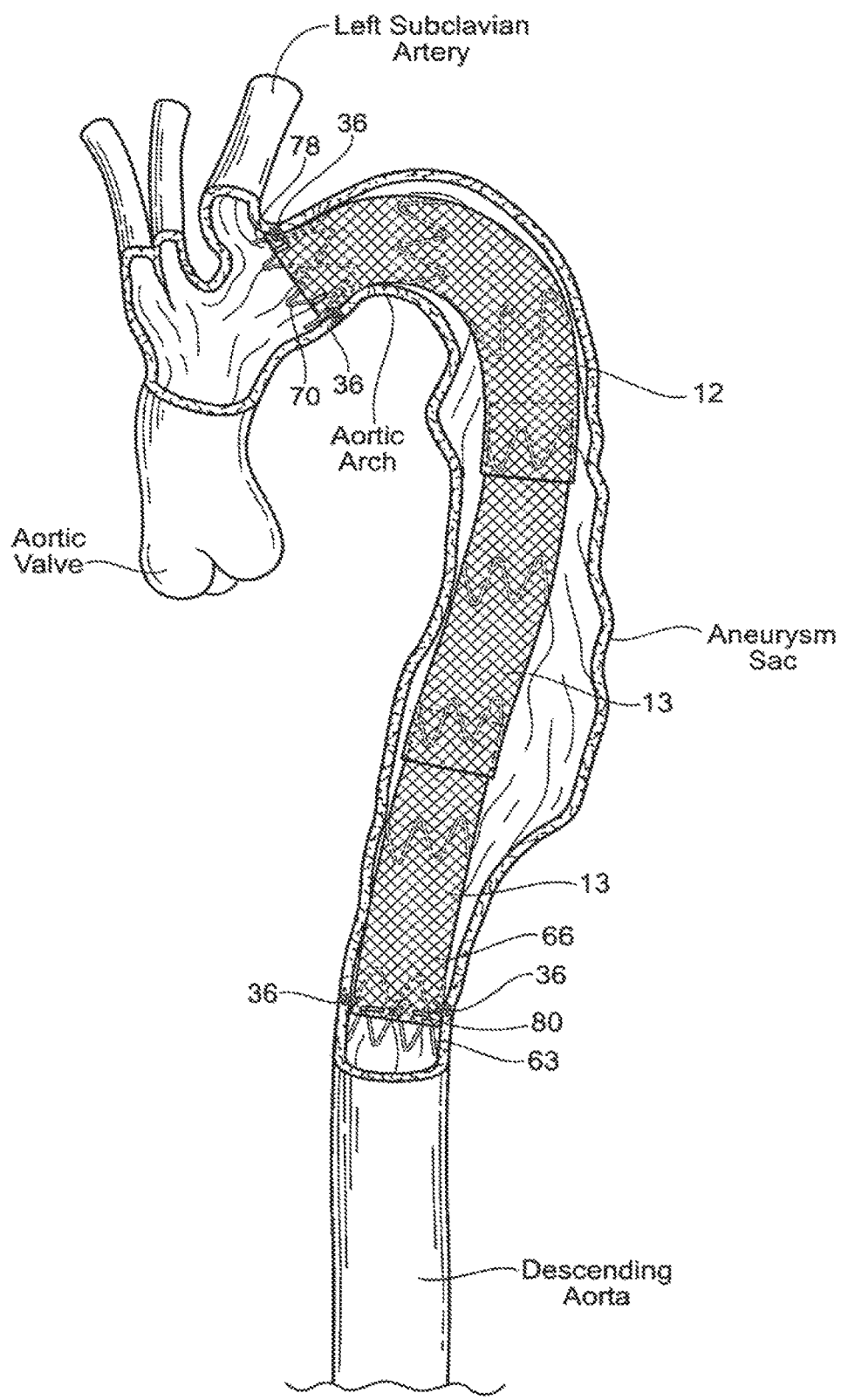
FIGS. 18A and 18B are anatomic views showing an alternative graft assembly comprising three graft assemblies nested together to extend the length of the implanted graft.
Figure 18B:
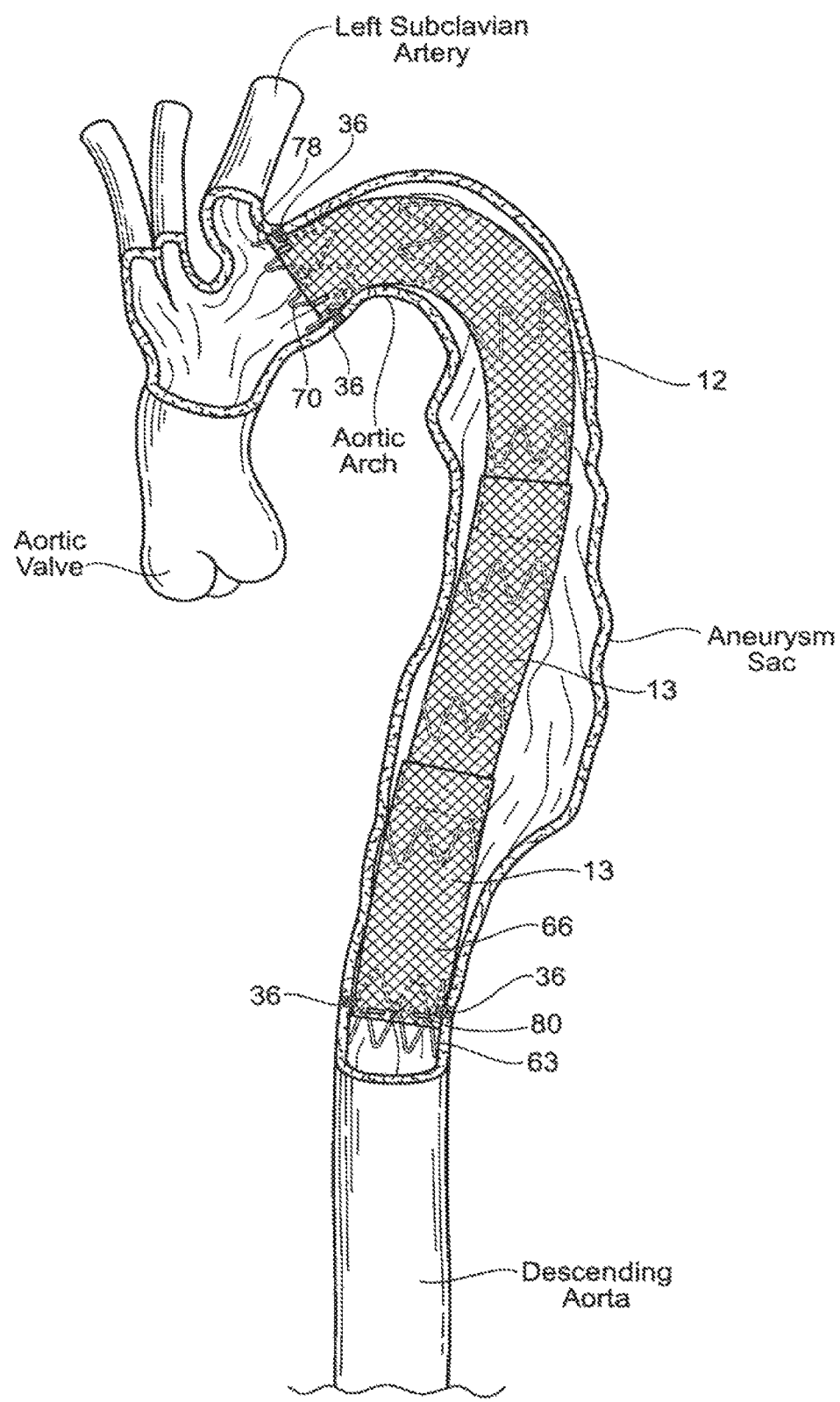

The systems and methods described herein may be used to implant an endovascular graft having one or more extensions 13, as can be seen in FIGS. 18A and 18B. Extensions 13 may be secured to the graft 12, or other extensions 13, using interlocking stents, for example. Or, the stapling system 16 may be used to apply a staple 36 at an overlap.

The staple 36 may pierce the overlapped graft segments of graft 12 and extension 13, and further may pierce into tissue, or, the tissue may not be pierced.

FIG. 18A shows one embodiment of a graft 12 including one or more extensions 13. In this embodiment, the graft 12 may be implanted first in the desired region of the vessel. Successive extensions may then be coupled to the graft 12 and/or a previously placed extension 13. This may be repeated until the aorta is covered from the desired proximal to distal landing zones. As can be seen, the proximal portion of the distal most two extensions 13 are shown as positioned inside of the graft/extension proximal to each extension.

FIG. 18B shows an alternative embodiment where the proximal portion of the distal most two extensions 13 are shown as positioned exterior to the outer diameter of the graft/extension proximal to each extension. In this embodiment, the first distal, extension 13 may be placed at or above the level of the celiac artery, for example. The column strength and/or radial expansion of the extension 13 may allow it to remain in position. One or more additional extensions 13 may be deployed further proximal to the first extension 13 with the distal portion of the second extension positioned inside of the proximal portion of the second extension 13 (or the graft 12) to extend the graft further proximal in the vessel. This may be repeated until the aorta is covered from the desired distal to proximal landing zones.

It will be appreciated that the components and/or features of the preferred embodiments described herein may be used together or separately, while the depicted methods and devices may be combined or modified in whole or in part. It is contemplated that the components of the guiding device, fastener device, and helical fastener may be alternately oriented relative to each other, for example, offset, bi-axial, etc. Further, it will be understood that the various embodiments may be used in additional procedures not described herein, such as vascular trauma, arterial dissections, artificial heart valve attachment and attachment of other prosthetic device victim the vascular system and generally within the body.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A steerable guide catheter comprising:
one and only one guide tube having a length and defining an open interior lumen, the lumen adapted for accommodating passage of an operative endovascular tool, the one guide tube comprising a first steerable segment and a second steerable segment at a distal end region of the one guide tube, and an integrated handle assembly comprising: a first rotational deflector knob coupled to the first steerable segment of the one guide tube to apply a deflecting force to bend the first steerable segment of the one guide tube, the first rotational deflector knob adapted to bend the first steerable segment in a first articulated position, and a second rotational deflector knob coupled to the second steerable segment of the guide tube to apply a deflecting force to bend the second steerable segment of the one guide tube, the second rotational deflector knob adapted to bend the second steerable segment in a second articulated position, the lumen extending through the first rotational deflector knob and the second rotational deflector knob.

2. A steerable guide catheter according to claim 1:
wherein the second articulated position is different than the first articulated position.

3. A steerable guide catheter according to claim 1:
further including an operative tool that applies one or more fasteners to tissue.

4. The steerable guide catheter of claim 1 wherein the first rotational deflector knob and the second rotational deflector knob are located at opposite ends of the integrated handle assembly.

5. The steerable guide catheter of claim 4 wherein the integrated handle assembly further comprises a control handle between the first rotational deflector knob and the second rotational deflector knob.

6. The steerable guide catheter of claim 1 further comprising:
 a first deflecting means directly coupling the first rotational deflector knob to the first steerable segment; and
 a second deflecting means directly coupling the second rotational deflector knob to the second steerable segment.

7. The steerable guide catheter of claim 6 wherein the first deflecting means and the second deflecting means are selected from the group consisting of steering wires and pull cords.

* * * * *